US011814428B2

(12) United States Patent
Kuhnert et al.

(10) Patent No.: US 11,814,428 B2
(45) Date of Patent: Nov. 14, 2023

(54) ANTI-PTCRA ANTIBODY-DRUG CONJUGATES AND USES THEREOF

(71) Applicant: REGENERON PHARMACEUTICALS, INC., Tarrytown, NY (US)

(72) Inventors: Frank Kuhnert, Cortlandt Manor, NY (US); Michael Van Meter, White Plains, NY (US); Thomas Nittoli, Pearl River, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 316 days.

(21) Appl. No.: 17/026,132

(22) Filed: Sep. 18, 2020

(65) Prior Publication Data

US 2021/0087272 A1    Mar. 25, 2021

Related U.S. Application Data

(60) Provisional application No. 62/902,674, filed on Sep. 19, 2019.

(51) Int. Cl.
| | |
|---|---|
| C07K 16/28 | (2006.01) |
| A61K 47/68 | (2017.01) |
| A61P 35/02 | (2006.01) |

(52) U.S. Cl.
CPC ...... *C07K 16/2809* (2013.01); *A61K 47/6803* (2017.08); *A61K 47/6849* (2017.08); *A61P 35/02* (2018.01)

(58) Field of Classification Search
None
See application file for complete search history.

(56) References Cited

U.S. PATENT DOCUMENTS

| | | | |
|---|---|---|---|
| 5,208,020 | A | 5/1993 | Chari |
| 5,500,362 | A | 3/1996 | Robinson |
| 5,714,586 | A | 2/1998 | Kunstmann |
| 5,821,337 | A | 10/1998 | Carter |
| 7,087,411 | B2 | 8/2006 | Daly |
| 7,750,116 | B1 | 7/2010 | Doronina |
| 7,754,681 | B2 | 7/2010 | Feng |
| 9,950,076 | B2 | 4/2018 | Nittoli |
| 10,570,151 | B2 | 2/2020 | Nittoli |
| 2007/0258987 | A1 | 11/2007 | Francisco |
| 2008/0305497 | A1 | 12/2008 | Kosmeder |
| 2009/0142354 | A1 | 6/2009 | Papadopoulos |
| 2010/0129314 | A1 | 5/2010 | Singh |
| 2011/0027286 | A1 | 2/2011 | Thurston et al. |
| 2013/0101546 | A1 | 4/2013 | Yurkovetskiy |
| 2016/0354482 | A1 | 12/2016 | Nittoli |
| 2016/0375147 | A1 | 12/2016 | Nittoli |
| 2017/0209591 | A1 | 7/2017 | Nittoli |
| 2018/0134794 | A1* | 5/2018 | Babb .................. A61K 47/6889 |
| 2018/0169261 | A1* | 6/2018 | Sutherland .............. A61P 35/00 |

FOREIGN PATENT DOCUMENTS

| | | |
|---|---|---|
| CN | 109045307 A | 12/2018 |
| WO | 2005/089808 | 9/2005 |
| WO | 2007/043200 | 4/2007 |
| WO | 2008/122039 | 10/2008 |
| WO | 2010/010324 | 1/2010 |
| WO | 2011/018611 | 2/2011 |
| WO | 2011/0130598 | 10/2011 |
| WO | 2012/005982 | 1/2012 |
| WO | 2012/058592 | 5/2012 |
| WO | 2012/166559 | 12/2012 |
| WO | 2013/053872 | 4/2013 |
| WO | 2013/053873 | 4/2013 |
| WO | 2013/055990 | 4/2013 |
| WO | 2013/055993 | 4/2013 |
| WO | 2013/068874 | 5/2013 |
| WO | 2013/085925 | 6/2013 |
| WO | 2014/065661 | 5/2014 |
| WO | 2014/145090 | 9/2014 |
| WO | 2015/026907 | 2/2015 |
| WO | 2015/031396 | 3/2015 |
| WO | 2016/037514 | 3/2016 |
| WO | 2016/160615 | 10/2016 |
| WO | 2018/058001 | 3/2018 |
| WO | 2018/058003 | 3/2018 |
| WO | 2018/067331 | 4/2018 |

OTHER PUBLICATIONS

Ivanyi et al., Cellular Oncology 32: 101-108 (Year: 2010).*
Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
PCT International Search Report and Written Opinion in International Application PCT/US2020/051688, dated Dec. 21, 2020, 22 pages.
Zuurbier, L. et al., "NOTCH1 and/or FBXW7 mutations predict for initial good prednisone response but not for improved outcome in pediatric T-cell acute lymphoblastic leukemia patients treated on DCOG or COALL protocols", Blood Cancer Journal, vol. 24, No. 12, Dec. 1, 2010, pp. 2014-2022.
Tremblay, M. et al., "Modeling T-cell acute lymphoblastic leukemia induced by the SCL and LMOI oncogenes", Genes & Development, vol. 24, No. 11, Jun. 1, 2010, pp. 1093-1105.
Kuhnert, F. et al., "Pre-T Cell Receptor Signaling Drives Leukemogenesis and is a Therapeutic Target Int Cell Acutelymphoblastic Leukemia", Hematological Oncology, vol. 37, Jun. 1, 2019, pp. 365-366.
Nittoli, Thomas et al., "Antibody drug conjugates of cleavable amino-alkyl and aryl maytansinoids", Bioorganic & Medicinal Chemistry, vol. 26, No. 9, May 1, 2018, pp. 2271-2279.

(Continued)

*Primary Examiner* — Phuong Huynh
(74) *Attorney, Agent, or Firm* — Merchant & Gould P.C.

(57) ABSTRACT

The present disclosure provides antibody-drug conjugates comprising anti-PTCRA antibodies and methods of using the same. The ADCs of the disclosure are useful for the treatment of T-ALL and other disorders related to elevated expression of PTCRA.

22 Claims, 21 Drawing Sheets

Specification includes a Sequence Listing.

(56) References Cited

OTHER PUBLICATIONS

Jie Gao et al., "Therapeutic targeting of Notch signaling and immune checkpoint blockade in a spontaneous, genetically heterogeneous mouse model of T-cell acute lymphoblastic leukemia", Disease Models & Mechanisms, vol. 12, No. 9, Sep. 1, 2019, 10 pgs.
Aarnoudse et al., "TCR Reconstitution in Jurkat Reporter Cells Facilitates the Identification of Novel Tumor Antigens by CDNA Expression Cloning", 2002 Int J Cancer 99:7-13.
Agarwal et al., "A Pictet-Spengler ligation for protein chemical modification", Proc. Natl. Acad. Sci., USA, Jan. 2, 2013, 110:46-51.
Altschul et al., "Gapped BLAST and PSI-BLAST: A New Generation of Protein Database Search Programs", (1997) Nucleic Acids Res. 25:3389-402.
Altschul et al., Basic Local Alignment Search Tool, (1990) J. Mol. Biol. 215:403-410.
Angal et al., "A Single Amino Acid Substitution Abolishes the Heterogeneity of Chimeric Mouse/Human (IgG4) Antibody", (1993) Molecular Immunology 30, No. 1, pp. 105-108.
Antibody-Drug Conjugates and Immunotoxins; Phillips, G. L., Ed .; Springer Verlag: New York, 2013, Chapter 1—"Antibody Directed Delivery for Treatment of Cancer: Antibody Drug Conjugates and Immunotoxins", Pamela A. Trail, pp. 3-22.
Antibody-Drug Conjugates and Immunotoxins; Phillips, G. L., Ed .; Springer Verlag: New York, 2013, Chapter 7—"Linker Technology and Impact of Linker Design on ADC Properties", Victor S. Goldmacher et al., pp. 117-135.
Antibody-Drug Conjugates; Ducry, L., Ed .; Humana Press, 2013, Chapter 6—"In Vivo Testing of Drug- Linker Stability", Pierre-Yves Abecassis et al., pp. 101-116.
Antibody-Drug Conjugates; Ducry, L., Ed .; Humana Press, 2013, Chapter 7—"Pharmacokinetics and ADME Characterizations of Antibody-Drug Conjugates", Kedan Lin et al., pp. 117-131.
Antibody-Drug Conjugates; Ducry, L., Ed .; Humana Press, 2013, Chapter 5—"Linker Technologies for Antibody-Drug Conjugates", Birte Nolting, pp. 71-100.
Antibody-Drug Conjugates; Wang, J., Shen, W.-C., and Zaro, J. L., Eds .; Springer International Publishing, 2015, Chapter 4—"Linker Design for Antibody-Drug Conjugates", E. Erica Hong et al., pp. 49-76.
Ashworth, et al., "Deletion-based mechanisms of Notch1 activation in T-ALL: Key roles for RAG recombinase and a conserved internal translational start site in Notch1", Dec. 16, 2010, Blood vol. 116, No. 25, pp. 5455-5464.
Barretina et al., "The Cancer Cell Line Encyclopedia enables predictive modelling of anticancer drug sensitivity", Mar. 29, 2012, Nature 483:603-607.
BD Biosciences, catalog item No. 552407, Purified Mouse Anti-Mouse Pre-T Cell Receptor a Chain", located online on Dec. 14, 20 at: https://www.bdbiosciences.com/US/reagetns/research/antibodies-buffers/immunology-rea . . . ", 5 pages.
Bellavia, et al., "Combined expression of a pTx and Notch3 in T cell leukemia identifies the requirement of a preTCR for leukemogenesis", Mar. 19, 2002, PNAS 99:3788-3793.
Bellavia, et al., "Constitutive activation of NF-KB and T-cell leukemia/lymphoma in Notch3 transgenic mice", 2000 EMBO Journal, vol. 19, No. 13, pp. 3337-3348.
Belver & Ferrando, "The genetics and mechanisms of T cell acute lymphoblastic leukaemia", Aug. 2016, Nat Rev Cancer 16:494-507. Cancer Cell Line Encyclopedia (CCLE) (Fig. 10A and data not shown).
Cancer Cell Line Encyclopedia, "Pharmacogenomic agreement between two cancer cell line data sets", 2015 Nature 528:84-87.
Carrico et al., "Introducing genetically encoded aldehydes into proteins", Nat. Chem. Biol., 2007, 3:321- 322.
Clynes et al., "Fc receptors are required in passive and active immunity to melanoma", (Jan. 1998) Proc. Natl. Acad. Sci. (USA) 95:652-656.
Doronina et al., "Development of potent monoclonal antibody auristatin conjugates for cancer therapy", Nature Biotechnology, 2003, 21, 7, 778-783.

Dos Santos et al., "Pre-TCR expression cooperates with TEL-JAK2 to transform immature thymocytes and induce T-cell leukemia", May 1, 2007 Blood 109:3972-3981.
Ducry et al., "Antibody—Drug Conjugates: Linking Cytotoxic Payloads to Monoclonal Antibodies", Bioconjugate Chem., 2010, 21:5-13.
Ehring, "Hydrogen Exchange/Electrospray Ionization Mass Spectrometry Studies of Structural Features of Proteins and Protein/Protein Interactions", (1999) Analytical Biochemistry 267(2):252-259.
Engen et al., "Investigating Protein Structure and Dynamics by Hydrogen Exchange MS", (May 1, 2001) Analytical Chemistry 73 (9), 256-265A.
Fehling et al., "Crucial role of the pre-T-cell receptor a gene in development of $\alpha\beta$ but not to $\gamma\delta$T cells", Jun. 29, 1995 Nature 375:795-798.
Gao et al., "Therapeutic targeting of Notch signaling and immune checkpoint blockade in a spontaneous, genetically heterogeneous mouse model of T-cell acute lymphoblastic leukemia", Jun. 10, 2019, Disease Models and Mechanisms 12: 1-10.
Gonnet et al., "Exhaustive Matching of the Entire Protein Sequence Database", (Jun. 5, 1992) Science 256: 1443-1445.
Goodson, Max J., 1984, in Medical Applications of Controlled Release, supra, vol. 2, pp. 115-138.
Grabher et al., "Notch 1 activation in the molecular pathogenesis of T-cell acute lymphoblastic leukaemia", May 2006 Nat Rev Cancer 6:347-359.
Haferlach et al., "Clinical utility of microarray-based gene expression profiling in the diagnosis and subclassification of leukemia: Report from the international microarray innovations in leukemia study group", 2010 J Clin Oncol 28:2529-2537.
Hochleitner et al., "Characterization of a discontinuous epitope of the human immunodeficiency virus (HIV) core protein p24 by epitope excision and differential chemical modification followed by mass spectrometric peptide mapping analysis", 2000, Protein Science 9:487-496.
Hofer et al., "An engineered selenocysteine defines a unique class of antibody derivatives", Proc. Natl. Acad. Sci., USA, Aug. 26, 2008, 105:12451-12456.
Hollander et al., "Selection of Reaction Additives Used in the Preparation of Monomeric Antibody—Calicheamicin Conjugates", Bioconjugate Chem., 2008, 19:358-361.
Jeger et al., "Site-specific and stoichiometric modification of antibodies by bacterial transglutaminase", Angew Chemie Inter Ed. 2010, 49, 9995-9997.
Junghans et al., "Anti-Tac-H, a humanized antibody to the interleukin 2 receptor with new features for immunotherapy in malignant and immune disorders", Cancer Res. Mar. 1, 1990:50:1495-1502.
Langer, "New Methods of Drug Delivery", Sep. 28, 1990, Science 249:1527-1533.
Liao et al., "No requirement for V(D)J recombination in p53-deficient thymic lymphoma", 1998 Mol. Cell Biol 18:3495-3901.
Lin et al., "Lck domains differentially contribute to Pre-T cell receptor (TCR)—and TCR-a/B-regulated developmental Transitions", Feb. 21, 2000 J Exp Med 191 :703-716.
Litzow & Ferrando, "How I Treat T-cell Acute Lymphoblastic Leukemia in Adults", Aug. 13, 2015 Blood 126: 833-841.
Liu et al., "The genomic landscape of pediatric and young adult T-lineage acute lymphoblastic leukemia", 2017 Nat Genet 49:1211-1218.
Mancini et al., "TCR x-Chain repertoire in pTx-deficient mice is diverse and developmentally regulated: implications for pre-TCR functions and TCRA gene rearrangement", 1999 J Immunol 163:6053-6059.
Marks & Rowntree, "Management of adults with T-cell lymphoblastic leukemia", Mar. 2, 2017 Blood 129:1134-1142.
Martin et al., "Infectious complications associated with alemtuzumab use for lymphoproliferative disorders", Jul. 1, 2006 Clin Infect Dis 43:16-24.
Martins et al., "Cell composition is a tumour suppressor mechanism in the thymus", May 22, 2014 Nature 509:465-470.

(56) References Cited

OTHER PUBLICATIONS

Molteni et al., "PTPN11 mutations in childhood acute lymphoblastic leukemia occur as a secondary event associated with high hyperdiploidy", 2010 Leukemia 24:232-235.
Mordenti et al., "Interspecies scaling of clearance and volume of distribution data for five therapeutic proteins", 1991, Pharmaceut. Res. 8:1351-1359.
PCT Application PCT/US2014/029757 filed Mar. 14, 2014, Client Ref.: 1550A-WO, 97 pages.
Pearson, "Using the FASTA program to search protein and DNA sequence databases", (1994) Methods Mol. Biol. 24: 307-331.
Petiniot et al. "Recombinase-activating gene (RAG) 2-mediated V(D)J recombination is not essential for tumorigenesis in Atm-deficient mice", Jun. 6, 2000 PNAS USA, vol. 97, No. 12, pp. 6664-6669.
Powell et al., "Compendium of excipients for parenteral formulations", PDA (1998) J Pharm Sci Technol 52:238-311.
Pui et al., "Acute lymphoblastic leukaemia", Mar. 22, 2008 Lancet 371:1030-1043.
Rabuka et al., "Site-specific chemical protein conjugation using genetically encoded aldehyde tags", Nat. Protocols, 2012, 10:1052-1067.
Reddy et al., "Elimination of Fc receptor-dependent effector functions of a modified IgG4 monoclonal antibody to human CD4", 2000, J. Immunol. 164:1925-1933.
Reineke, "Antibody epitope mapping using arrays of synthetic peptides", 2004, Methods Mol. Biol 248:443-463.
Ryan et al., "Polyclonal Antibody Production Against Chito-Oligosaccharides", Food & Agriculture Immunol., 2001, 13:127-130.
Sapra et al., "Monoclonal antibody-based therapies in cancer: Advances and challenges", Pharmacol. & Therapeutics, 2013, 138:452-469.
Schumacher et al., "Current Status: Site-Specific Antibody Drug Conjugates", J Clin Immunol (2016) 36 (Suppl 1): 100-107.
Sefton, Michael, "Implantable Pumps", Langer, supra; 1987, CRC Crit. Rev Biomed. Eng. vol. 14, No. 3, pp. 201-240.
Shaunak et al., "Site-specific PEGylation of native disulfide bonds in therapeutic proteins", Nat. Chem. Biol., 2006, 2:312-313.
Shields et al., "Lack of fucose on human IgG1 N-linked Oligosaccharide improves binding to human FcγRIII and antibody-dependent cellular toxicity", 2002 JBC 277:26733-26740.
Takebe et al., "Targeting notch signaling pathway in cancer: Clinical development advances and challenges", 2014 Pharmacol Ther 141:140-149.
Taylor et al., "A transgenic mouse that expresses a diversity of human sequence heavy and light chain immunoglobins", (1992) Nucl. Acids Res. 20:6287-6295.
Vadillo et al., "T cell acute lymphoblastic leukemia (T-ALL): New insights into the cellular origins and infiltration mechanisms common and unique among hematologic malignancies", 2018 Blood Rev 32:36-51.
Von Boehmer, "Unique features of the pre-T-cell receptor x-chain: not just a surrogate", 2005 Nat Rev Immunol 5:571-577.
Wei et al., "Evaluation of selective γ-secretase inhibitor PF-03084014 for its antitumor efficacy and gastrointestinal safety to guide optimal clinical trial design", 2010 Mol Cancer Ther 9:1618-1628.
Winandy et al., "Pre-T cell receptors (TCR) and TCR-controlled checkpoints in T Cell differentiation are set by Ikaros", 1999 J Exp Med 190:1039-1048.
Wu et al., "Receptor-mediated in Vitro gene transformation by a soluble DNA carrier system", 1987, J. Biol. Chem. 262:4429-4432.
Zhang et al., "The genetics basis of early T-cell precursor acute lymphoblastic leukaemia", 2012 Nature 481:157-163.
Zhou, Xin et al., "Exploring genomic alteration in pediatric cancer using ProteinPaint", Nature Genetics, vol. 48, No. 1, Jan. 2016, pp. 4-6.

* cited by examiner

| Gene ID | Fold-change compared to peripheral blood monocytes |
|---|---|
| Rpl34 | 3994.62 |
| Rag1 | 773.02 |
| Hmga1 | 456.69 |
| Syt13 | 238.04 |
| Ptcra | 182.94 |
| Dynlt1c | 181.10 |
| Arpp21 | 183.49 |
| Rag2 | 110.75 |
| Endou | 192.66 |
| Nutf2 | 133.63 |
| Gfra1 | 79.37 |
| H2-T3 | 59.87 |
| Hba-a1 | 105.42 |
| Oaz1 | 49.27 |
| Arsi | 75.22 |
| Dynlt1c | 76.05 |
| Onlt | 94.21 |
| Pdgfrb | 48.38 |
| Uaca | 53.58 |
| Aqp11 | 65.70 |
| H2-Q2 | 58.25 |
| Cym | 35.04 |
| Hba-a1 | 61.46 |
| Slc4a1 | 31.49 |
| a_2 | 29.10 |
| Gypa | 29.85 |
| Mpz2 | 32.35 |
| Wscd1 | 27.38 |
| Tmem121 | 33.60 |
| Nt5dc2 | 42.88 |
| F2_2 | 24.24 |
| Notch3 | 36.74 |
| Cxcl18 | 40.36 |
| Rorc | 40.02 |
| Sertad4 | 19.23 |
| Smo | 34.75 |
| Fbp1 | 19.32 |
| Ybx2 | 17.86 |
| H2-Q1 | 17.85 |
| Ppp1r1b | 17.93 |
| Hey1 | 19.47 |
| Haor1 | 25.53 |
| Pbk | 31.69 |
| Cldn13 | 17.77 |
| Slc5a9 | 16.38 |
| Rhag | 17.81 |
| Vasn1 | 20.18 |
| Tdrd5 | 18.43 |
| Foxb1 | 16.40 |
| Zfp704 | 23.04 |

| Gene ID | Fold-change compared to peripheral blood monocytes |
|---|---|
| Il6b | 15.18 |
| Rnaset2a | 29.29 |
| Rhd | 17.95 |
| Gzma | 29.90 |
| H1fx | 16.00 |
| Tmem151b | 20.46 |
| Plk? | 19.41 |
| Cxcl153 | 14.18 |
| H2-Ea-ps | 15.24 |
| Cps4 | 14.71 |
| Fbln2 | 15.90 |
| Hbb-b1 | 28.42 |
| P2rx1 | 22.98 |
| Gpr25 | 21.33 |
| Hemgn | 21.85 |
| Hbb-bs | 25.80 |
| Cpeb1 | 14.95 |
| P3h4 | 17.36 |
| Rapgef3 | 20.54 |
| Mpp4 | 16.15 |
| Prss57 | 14.50 |
| Iqch | 11.96 |
| Nwd1 | 12.77 |
| Vwce | 13.21 |
| Bex4 | 13.59 |
| Hist1h3h | 16.49 |
| Camsv | 11.69 |
| Kel | 11.67 |
| Cnlg | 22.72 |
| Reep1 | 15.00 |
| Spats2 | 20.34 |
| Chrna9 | 13.37 |
| Col27a1 | 18.88 |

FIG. 2

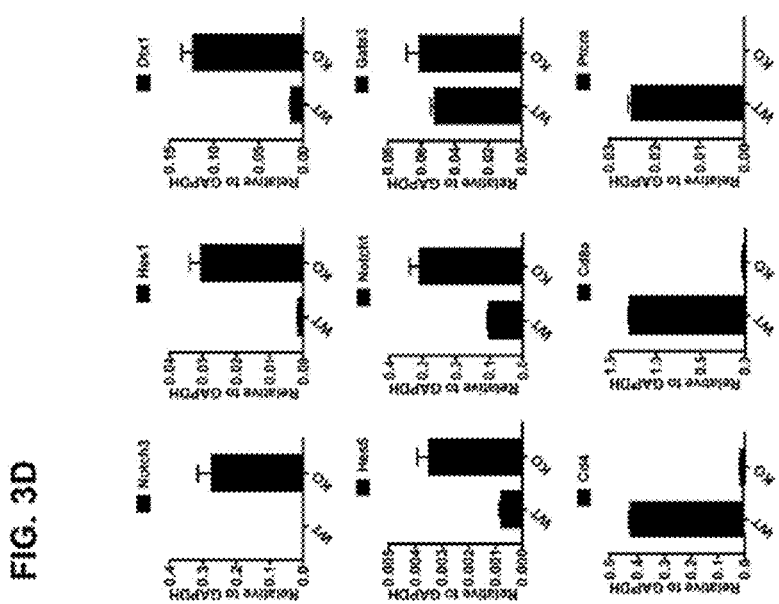
FIG. 3D
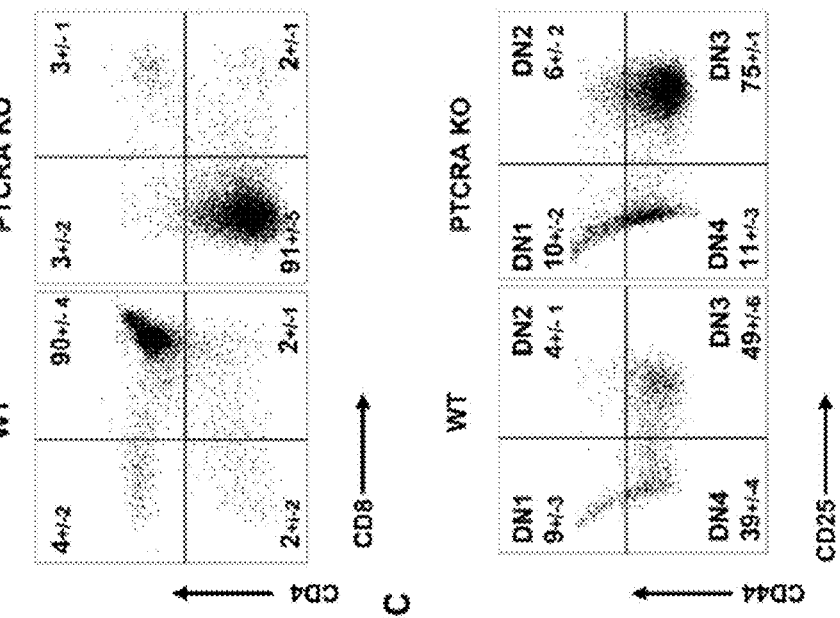
FIG. 3B
FIG. 3C
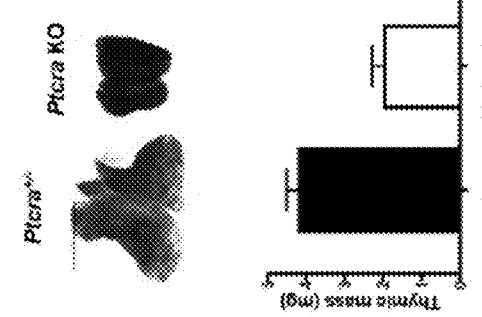
FIG. 3A

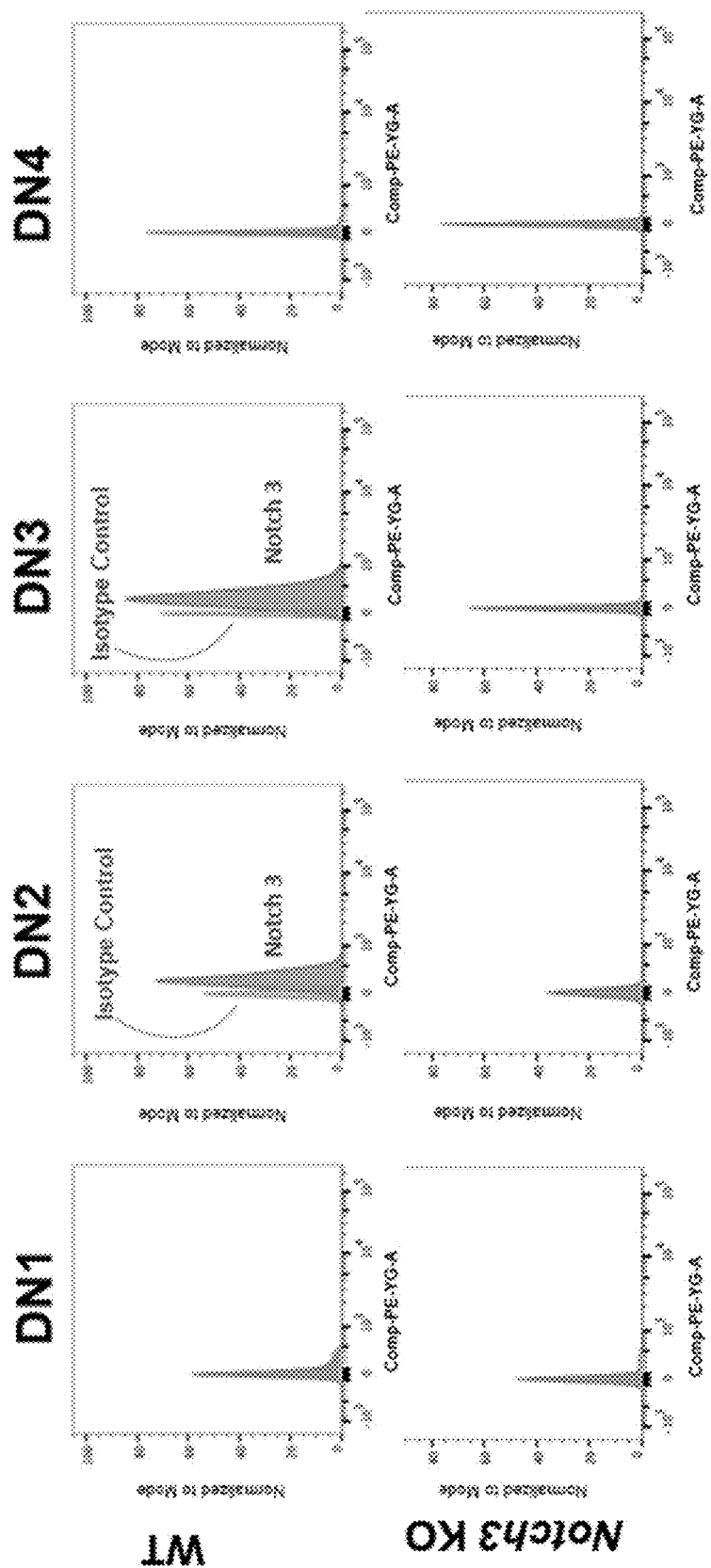
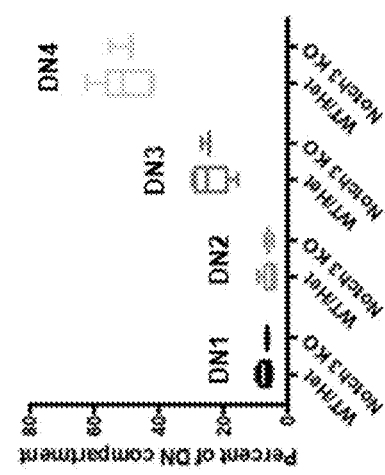
FIGURE 5A
FIGURE 5B

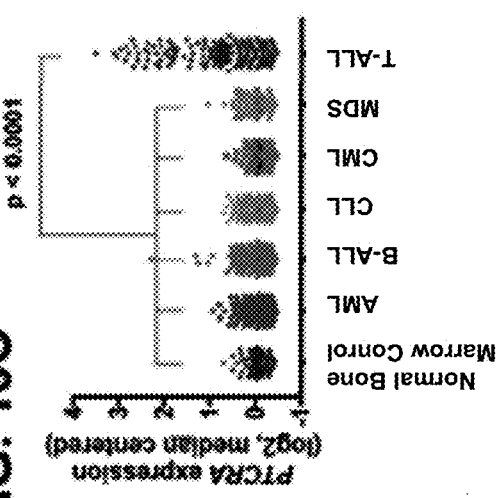
FIG. 10A
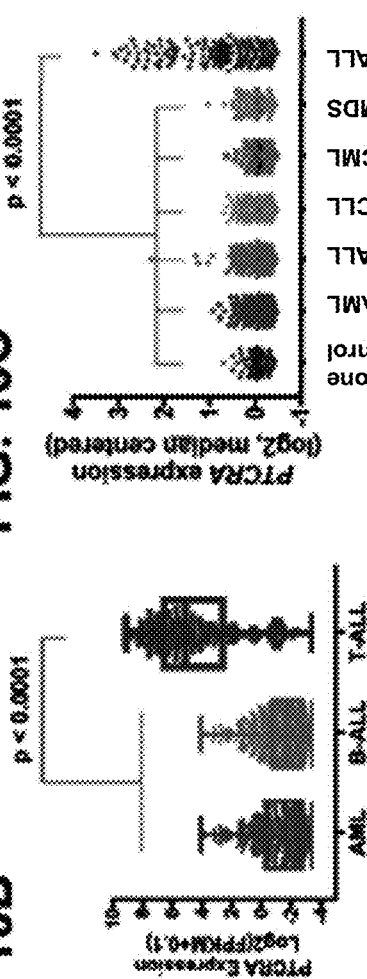
FIG. 10B
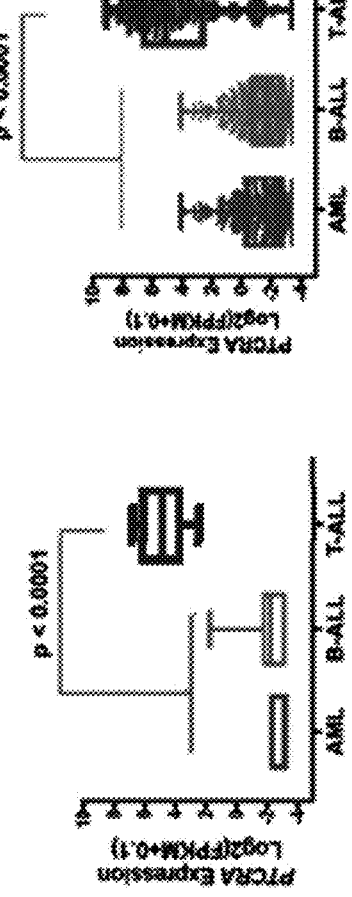
FIG. 10C
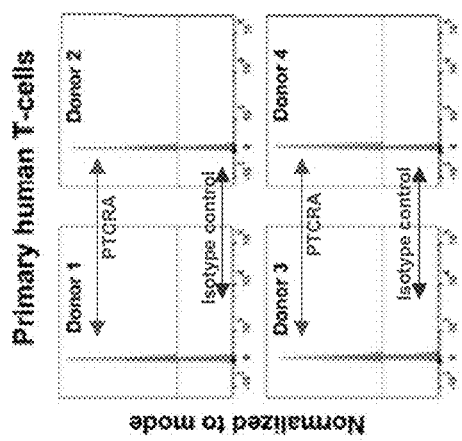
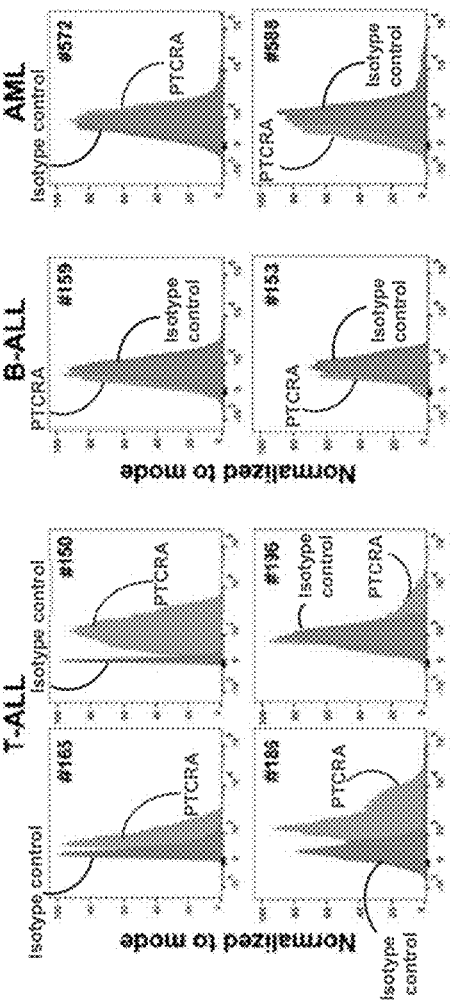
FIG. 10D
FIG. 10E

| Sample ID | Sex | Age | Ethnicity | Clinical diagnosis | Disease status | Organs involved |
|---|---|---|---|---|---|---|
| 150 | M | 20 | Caucasian | T-ALL | resistant to therapy | bone marrow |
| 152 | M | 19 | Caucasian | B-ALL | at diagnosis | bone marrow, spleen, liver |
| 158 | M | 30 | Caucasian | Pre-B-ALL | at diagnosis | bone marrow |
| 165 | M | 50 | Caucasian | T-ALL | at diagnosis | bone marrow |
| 188 | M | 40 | Caucasian | pre-T-ALL (transformed from T-cell lymphoma (NOS)) | at diagnosis | bone marrow, liver, spleen |
| 196 | M | 44 | Caucasian | Pre-T-ALL (T:1 variant) | at diagnosis | bone marrow |
| 572 | F | 72 | Caucasian | AML | at diagnosis | bone marrow |
| 588 | F | 69 | Caucasian | AML | at diagnosis | bone marrow |

FIG. 13

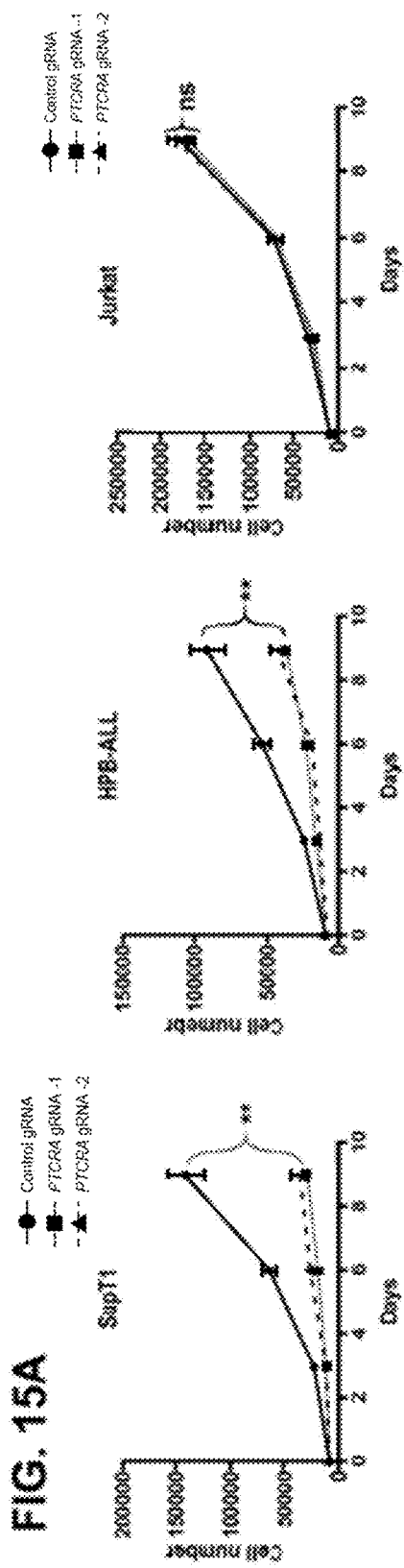
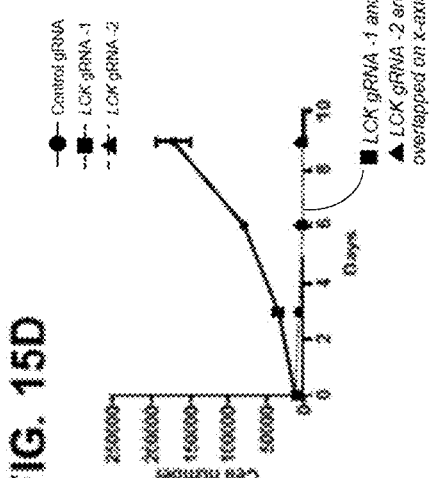
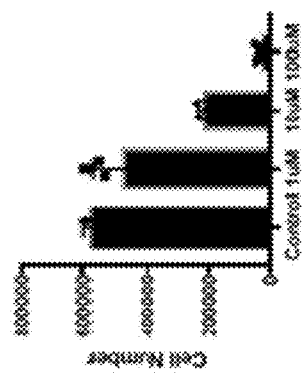
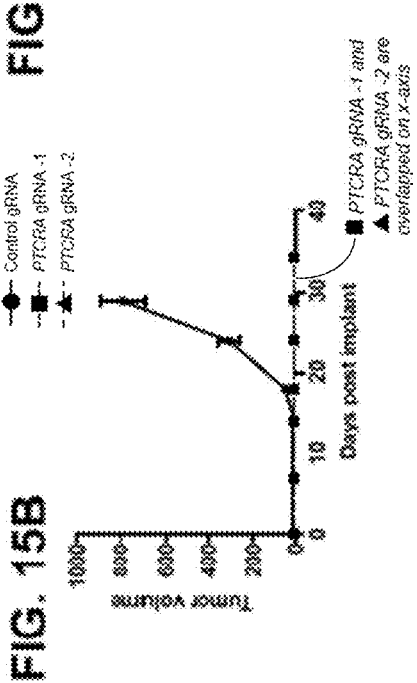
FIG. 15A
FIG. 15B
FIG. 15C
FIG. 15D

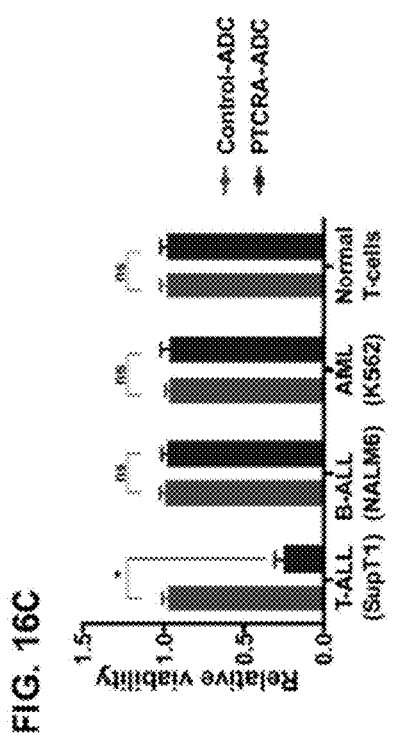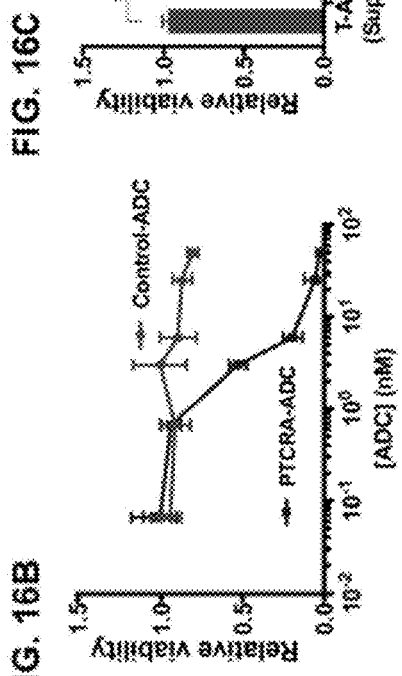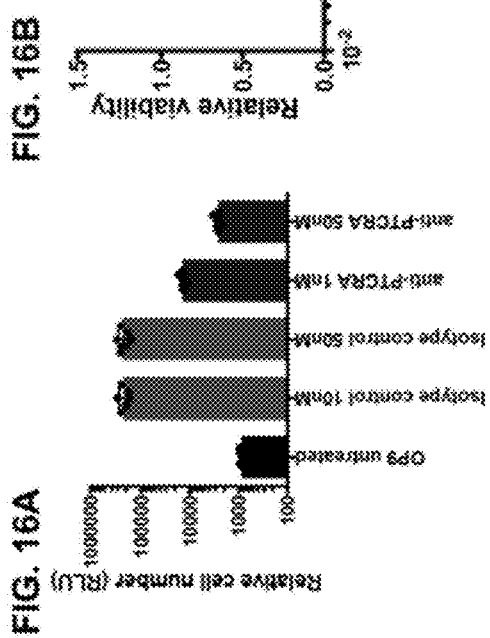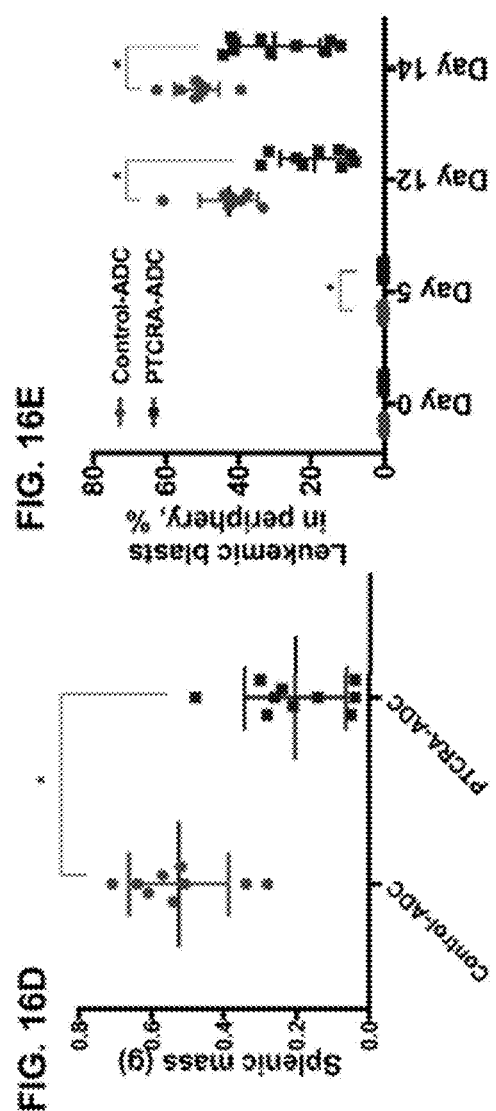
FIG. 16A FIG. 16B FIG. 16C FIG. 16D FIG. 16E

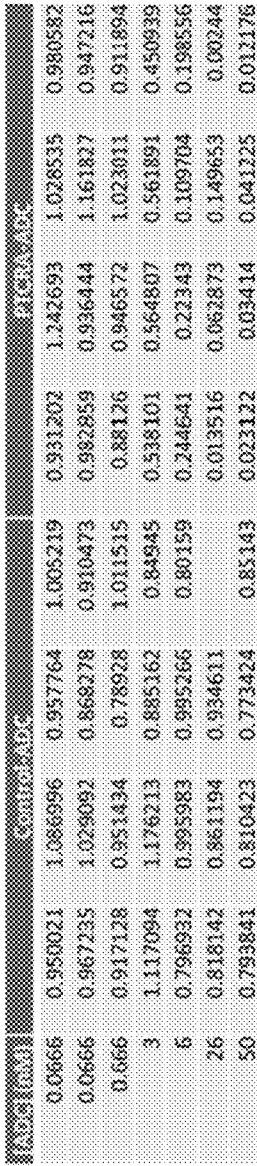

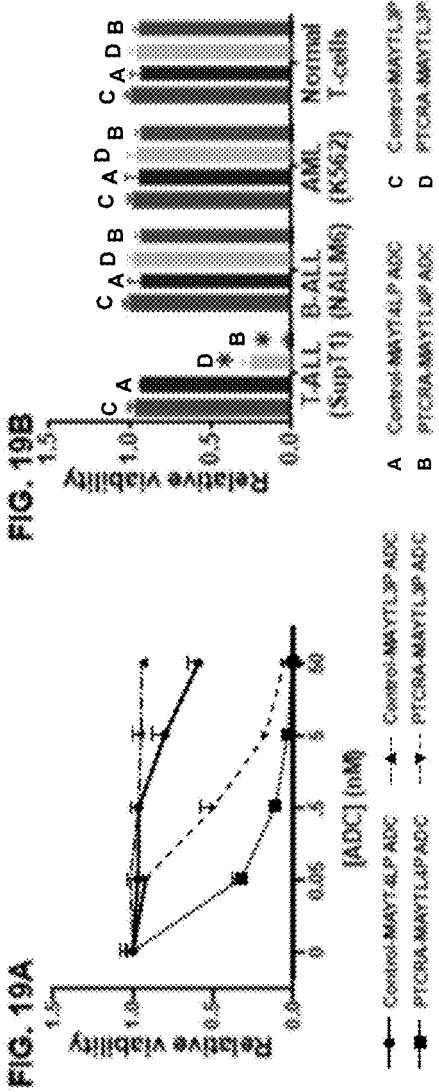
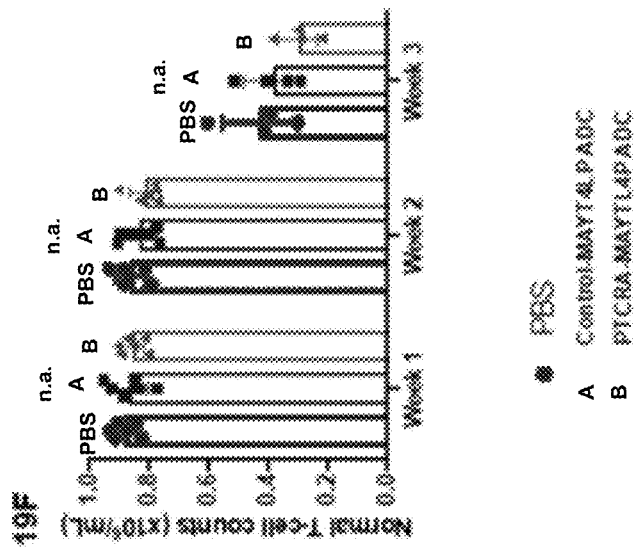
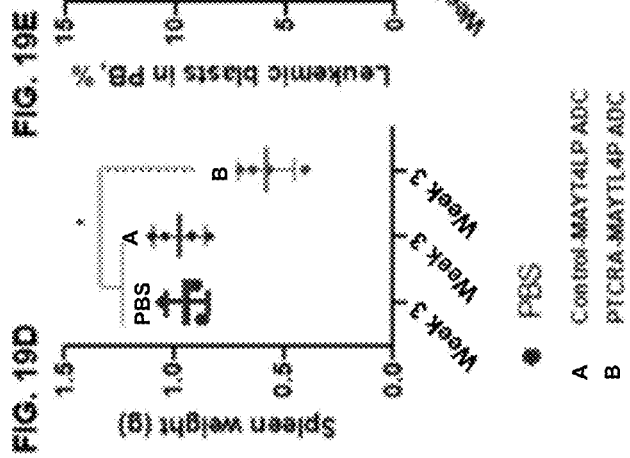

FIG. 19G

| Dose ADC (nM) | Control-M2921 ADC | | | | | PTCRA-M2921 ADC | | | | | Control-M1114 ADC | | | | | PTCRA-M1114 ADC | | | | |
|---|---|---|---|---|---|---|---|---|---|---|---|---|---|---|---|---|---|---|---|---|
| 0 | 1.03 | 0.94 | 0.99 | 1.06 | 0.99 | 1.03 | 1.02 | 0.98 | 1.04 | 0.98 | 1.01 | 0.96 | 0.98 | 0.98 | 1.1 |
| 0.05 | 0.89 | 1.03 | 1.02 | 0.96 | 0.93 | 0.29 | 0.4 | 0.81 | 1.03 | 0.67 | 1.02 | 1.04 | 0.87 | 0.96 |
| 0.5 | 1.01 | 0.9 | 0.97 | 0.99 | 0.14 | 0.1 | 0.12 | 0.96 | 1.03 | 0.91 | 1 | 0.49 | 0.55 | 0.59 |
| 5 | 0.71 | 0.79 | 0.87 | 0.85 | 0.04 | 0.02 | 0.01 | 0.01 | 0.95 | 1.03 | 0.94 | 0.12 | 0.29 | 0.39 | 0.18 |
| 50 | 0.56 | 0.52 | 0.63 | 0.66 | 0.01 | 0 | 0.03 | 0.03 | 0.91 | 0.96 | 0.93 | 0.05 | 0.08 | 0.04 | 0.03 |

FIG. 19H

| | T-ALL (SupT1) | | B-ALL (NALM6) | | AML (K562) | | Normal T-cells | |
|---|---|---|---|---|---|---|---|---|
| Control-M/T3LP ADC | 0.98 | 0.91 | 1.00 | 0.98 | 0.95 | 1.01 | 0.95 | 1.02 |
| Control-M/T4LP ADC | 0.93 | 0.92 | 0.89 | 0.91 | 0.91 | 0.88 | 0.87 | 0.96 |
| PTCRA-M/T3LP ADC | 0.31 | 0.21 | 1.01 | 0.96 | 0.91 | 0.94 | 0.99 | 0.93 |
| PTCRA-M/T4LP ADC | 0.05 | 0.02 | 0.93 | 0.97 | 0.89 | 0.95 | 0.97 | 0.93 |

US 11,814,428 B2

ANTI-PTCRA ANTIBODY-DRUG CONJUGATES AND USES THEREOF

CROSS-REFERENCE TO RELATED APPLICATIONS

This application claims priority to U.S. Provisional Patent Application No. 62/902,674 filed Sep. 19, 2019, the contents of which are incorporated by reference herein.

SEQUENCE STATEMENT

The instant application contains a Sequence Listing, which has been submitted electronically in ASCII format and is hereby incorporated by reference in its entirety. Said ASCII copy, created on Sep. 18, 2020, is named 40848-0096USU1-SEQLIST.TXT and is 5,000 kilobytes in size.

FIELD OF THE DISCLOSURE

The present disclosure relates to antibody-drug conjugates that specifically bind Pre T-Cell Antigen Receptor Alpha (PTCRA).

BACKGROUND

T-cell acute lymphoblastic leukemia (T-ALL) is an aggressive hematologic tumor that arises from the malignant transformation of T-cell progenitors (Belver & Ferrando 2016 Nat Rev Cancer 16:494-507; Vadillo, et al. 2018 *Blood Rev* 32:36-51). The disease accounts for 15-25% of acute lymphoblastic leukemia cases and affects both children and adults. The implementation of intensive, multi-agent chemotherapy regimens has dramatically improved disease outcomes, particularly in the pediatric setting (Pui, et al. 2008 *Lancet* 371:1030-1043). However, there are no targeted therapies for T-ALL, and patients whose disease is chemorefractory or has relapsed remain a major unmet medical need (Ferrando 2015 *Blood* 126: 833-841; Marks & Rowntree 2017 *Blood* 129:1134-1142). The lack of targeted therapies necessitates the discovery of additional therapeutic targets in T-ALL and a better understanding of the disease biology.

The Pre T-Cell Antigen Receptor Alpha (PTCRA) protein is a single-pass type I membrane protein found in immature (not mature) T-cells. Along with T cell receptor beta (TCRB) and cluster or differentiation 3 (CD3) complex, it forms the pre-T cell receptor complex, which regulates early T-cell development.

BRIEF SUMMARY

Provided herein are antibodies and antigen-binding fragments thereof that bind Pre T-Cell Antigen Receptor Alpha (PTCRA), wherein the antibodies and antigen-binding fragments are conjugated to a therapeutic moiety. The antibody-drug conjugates (ADCs) disclosed herein are useful, inter alia, for targeting tumor cells that express PTCRA.

In another aspect, the disclosure provides a pharmaceutical composition comprising antibody-drug conjugates that specifically bind PTCRA and a pharmaceutically acceptable carrier. In a related aspect, the disclosure provides a composition that is a combination of an anti-PTCRA antibody-drug-conjugate and a second therapeutic agent. In one embodiment, the second therapeutic agent is any agent that is advantageously combined with an anti-PTCRA antibody-drug conjugate. Exemplary combination therapies, co-formulations, and antibody-drug conjugates are disclosed elsewhere herein.

In yet another aspect, the disclosure provides therapeutic methods for killing tumor cells or for inhibiting or attenuating tumor cell growth using an antibody-drug conjugate comprising an anti-PTCRA antibody or antigen-binding portion thereof and a therapeutic moiety. The therapeutic methods according to this aspect of the disclosure comprise administering a therapeutically effective amount of a pharmaceutical composition comprising an antibody-drug conjugate disclosed herein to a subject in need thereof. The disorder treated is any disease or condition that is improved, ameliorated, inhibited, or prevented by targeting PTCRA and/or by inhibiting cell signaling through PTCRA.

Other embodiments will become apparent from a review of the ensuing detailed description.

DETAILED DESCRIPTION

It is to be understood that this disclosure is not limited to particular methods and experimental conditions described, as such methods and conditions may vary. It is also to be understood that the terminology used herein is for the purpose of describing particular embodiments only, and is not intended to be limiting, since the scope of the disclosure will be limited only by the appended claims.

Unless defined otherwise, all technical and scientific terms used herein have the same meaning as commonly understood by one of ordinary skill in the art to which this disclosure belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). The terms "Figure" and "FIG." are used interchangeably throughout the specification.

Although any methods and materials similar or equivalent to those described herein can be used in the practice or testing of the antibody-drug conjugates and compositions and methods and uses, the preferred methods and materials are now described. All patents, applications and non-patent publications mentioned in this specification are incorporated herein by reference in their entireties.

BRIEF DESCRIPTION OF THE FIGURES

FIG. 1A shows a heat map of select β-selection factors in T-ALL tumors vs. control spleens. Cxcr4, Myc, Notch1, Notch3, Ptcra, Rag1, Rag2, and Dntt are all strongly upregulated in T-ALL samples, relative to control spleens; Robust Center Scale normalized. FIGS. 1B-1D show expression of Ptcra (1B), Notch3 (1C), and Notch1 (1D) across various control tissues and in primary T-ALL tumors. FIGS. 1E-1G show cell surface expression of Ptcra (1E), Notch3 (1F), and Notch1 (1G) in a representative T-ALL case.

FIG. 2 shows a table listing the top differentially expressed genes in a thymic transplantation model of T-ALL (the top genes differentially expressed in T-ALL tumors as compared to peripheral T-cells from C57B15 mice).

FIGS. 3A-3D demonstrate that Ptcra KO results in thymic hypoplasia and arrest of thymocytes at the DN3 checkpoint. FIG. 3A shows that thymi derived from Ptcra KO animals are markedly reduced in size (top), mass (middle, bar graph), and cellularity (bottom, bar graph). n=4, error bars indicate s.d. FIGS. 3B and 3C show immunoprofiling revealing that Ptcra KO thymi are largely devoid of DP cells (3B), and that most thymocytes are arrested at the DN3 stage (3C). n=5+/− s.d. FIG. 3D shows, in bar graph form, that, consistent with their immunophenotype, gene expression analysis reveals strong upregulation of DN3-associated genes and downregulation of DP markers in Ptcra KO thymus. n=5, error bars indicate s.d.

FIG. 4A shows representative immunophenotypes of thymi derived from young (~1 week old) and adult (~6 months old) wild type (WT) and Ptcra KO mice. FIG. 4B provides quantitation of the immunophenotyping analysis of young (upper bar graph) and old (lower bar graph) WT and Ptcra KO thymi. The developmental arrest of Ptcra KO thymocytes at DN3 is less pronounced by adulthood; the inability to complete the DN to DP transition is almost completely reversed.

FIGS. 5A and 5B demonstrate that genetic ablation of Notch3 does not impair thymocyte development. FIG. 5A shows expression of Notch3 at DN stages of thymocyte development in wild type (WT) and Notch3 KO thymi. Among the plots shown in 5A that show two distinct peaks, the Notch3 peak is the righthand peak. Among the plots shown in 5A that do not show two distinct peaks, the Notch3 and isotype control peaks overlap. FIG. 5B shows quantification of thymocytes in DN1-DN4 stages of development in WT and Notch3 KO thymi; no statistically significant differences were observed.

FIG. 7A shows survival curves of animals in thymic transplantation studies. Animals engrafted with wild type (WT) thymic lobes developed T-ALL with a median time to disease of approximately 25 weeks (blue line). Animals engrafted with either two Ptcra KO thymic lobes (red line) or between 4 to 8 Ptcra KO thymic lobes (green line) displayed a strong delay in leukemogenesis. n=25 for WT thymic transplants, n=35 for PTCRA KO transplants. P-value calculated by log-rank (Mantel-Cox) test. FIG. 7B shows monitoring of peripheral blasts in the periphery of representative WT thymus engrafted and Ptcra KO engrafted mice. FIG. 7C shows gene expression profiling of Ptcra KO vs WT tumors. Downregulated genes are enriched for Ptcra-target genes and genes involved in the DN to DP transition; upregulated genes are enriched for genes associated with ETP-ALL.

FIG. 8A shows that NOTCH3 is upregulated, relative to control samples, in human T-ALL patient samples. FIG. 8B shows that the TALL-1 human T-ALL cell line harbors a gain of function mutation in NOTCH3 (Notch3 HDD) and expresses wild type NOTCH1. Treating this cell line with gamma-secretase inhibitor (GSI) markedly inhibits cell proliferation.

FIGS. 10A-10E demonstrate that PTCRA is selectively upregulated in human T-ALL. FIG. 10A shows that PTCRA is expressed in the majority of human T-ALL cell lines, but not in AML or B-ALL cell lines analyzed in the Cancer Cell Line Encyclopedia. PTCRA RNA gene expression is plotted for the B-ALL, AML, and T-ALL cell lines in this dataset. FIG. 10B shows that PTCRA is highly expressed in the majority of T-ALL patients in the St. Jude Children's Research Hospital hematopoietic malignancies cohort, but not in AML and B-ALL samples. PTCRA RNA expression is plotted by tumor type. FIG. 10C shows that PTCRA is upregulated in T-ALL tumors relative to normal bone marrow control and non-T-ALL hematologic tumor types contained within the Haferlach patient cohort. In FIG. 10D, PTCRA cell surface expression, relative to isotype control, was assessed by flow cytometry in primary and chemotherapy refractory (#150) human T-ALL patient samples, human B-ALL patient samples and human AML patient samples. Surface staining was only observed in T-ALL samples. In FIG. 10E, PTCRA cell surface expression, relative to isotype control, was assessed by flow cytometry in primary human T-cells derived from PBMCs. Normal T-cells are sorted on viable CD45+CD3+ cells from donor PBMCs.

FIG. 11A: molecular subtyping of T-ALL tumors within the St. Jude Children's Research Hospital hematological cancer cohort according to genomic rearrangements and gene expression analysis highlights that PTCRA is broadly expressed across most T-ALL subtypes, with the exception of the most developmentally primitive, ETP-like subtypes. PTCRA expression in T-ALL was positively associated with NOTCH1 gain-of-function (GoF) mutations. In FIG. 11B, PTCRA expression is stratified based on NOTCH1 mutational status across the St. Jude's Pediatric Cancer Patient cohort. P-values calculated by one-way analysis of variance.

FIG. 13 shows a table listing characteristics of primary human malignancy samples described in FIGS. 10A-10E.

FIGS. 15A-15D demonstrate that deletion of PTCRA in human T-ALL cell lines significantly impaired cell proliferation. For FIG. 15A, SupT1 (left), HPB-ALL (middle), and Jurkat (right) cell lines were stably transduced with Cas9 and then transduced with the indicated gRNA. Proliferation was quantified following transduction with the gRNA. n=3, error bars indicate s.d. In FIG. 15B, subcutaneously implanted wild type SupT1 cells developed tumors in NSG mice, whereas SupT1 cells with PTCRA KO cells did not. n=3, error bars indicate s.d. In FIG. 15C, treatment of SupT1 cells with the SRC-family kinase inhibitor, PP1, induced a dose-dependent anti-proliferative response. n=5, error bars+/−s.d. In FIG. 15D, CRISPR/Cas9-mediated deletion of LCK in SupT1 cells strongly inhibited proliferation in vitro. n=3, error bars indicate +/−s.d.

FIGS. 16A-16I demonstrate that PTCRA-targeting antibody-drug conjugate drives specific killing of T-ALL cells in vivo and in vitro. For FIG. 16A, mTALL cells were plated on an OP9-DLL1 feeder layer and treated with either a PTCRA mAb or isotype control mAb at the indicated concentrations followed by treatment with 20 nM anti-mouse IgG Fc MMAE. Cell viability was quantified by CellTiterGlo Assay 96 h post treatment. n=4. In FIG. 16B, PTCRA mAB and an isotype control mAb were directly conjugated to a potent microtubule inhibitor. mTALL cells were plated on an OP9-DLL1 feeder layer and treated with the indicated dose of either Control-ADC or PTCRA-ADC. n=4. For FIG. 16C, various malignant and normal human cells were treated with either 10 nM PTCRA-ADC or 10 nM Control-ADC. Cell viability was quantified with CellTiter-Glo. n=3. The left-hand bar of each pair of bars (1 pair each for T-ALL (SupT1), B-ALL (NALM6), AML (K562), and normal T-cells) corresponds to Control-ADC, and the righthand bar corresponds to PTCRA-ADC. In FIG. 16D, 100,000 primary mTALL cells were injected i.v. into NSG mice. On day 2, mice were randomized by tumor burden (FACS, peripheral blood) and treated with either PTCRA-ADC or an Isotype Control-ADC. Treatment was on day 2, day 6, and day 12. Tumor burden was assessed at 14-day endpoint by splenic mass. For FIG. 16E, during treatment, tumor burden in peripheral blood was monitored by flow cytometry. The left-hand "column" of dots of each pair of "columns" of dots (1 pair each for day 0, day 5, day 12, and day 14) corresponds to Control-ADC, and the righthand "column" of dots corresponds to PTCRA-ADC. FIG. 16F provides the results of FIG. 16B in tabular form with numerical values. FIG. 16G provides the results of FIG. 16C in tabular form with numerical values. FIG. 16H provides the results of FIG. 16D in tabular form with numerical values. FIG. 16I provides the results of FIG. 16E in tabular form with numerical values.

In FIG. 18A, SupT1 cells, which endogenously express PTCRA, were stained with anti-PTCRA antibody (red) at 4° C. for thirty minutes whereupon the cells were temperature shifted to 37° C. and stained with a secondary antibody (green) at the indicated time post-temperature shift. The cells were then fixed and immuno-fluorescent confocal microscopy was used to visualize PTCRA localization. PTCRA was detected at the cell surface of SupT1 cells at 0 minutes, but rapidly and robustly internalizes over the time course being examined. In FIG. 18B, SupT1 cells were treated with the translation inhibitor, cycloheximide, for the indicated time period, at which time they were harvested, lysed, and the extracts were used for immunoblotting. PTCRA is rapidly degraded over the 8 h time course of the experiment.

FIGS. 19A-19H show that targeting PTCRA with cytotoxic antibody-drug conjugates promotes specific killing of T-ALL cells in vitro and in vivo. FIG. 19A shows, in line graph form, relative viability for increasing ADC concentration. FIG. 19B shows, in bar graph form, relative viability for varying linker-payloads in T-ALL (SupT1), B-ALL (NALM6), AML (K562), and normal T-cells. FIG. 19C shows, in line graph form, tumor volume over up to about 35 days post-implantation for control-MAYTL4PADC vs. PTCRA-MAYTL4PADC. FIG. 19D shows, in plot form, spleen weight at week 3 for PBS vs. control-MAYTL4PADC vs. PTCRA-MAYTL4PADC. FIG. 19E shows, in plot form, leukemic blasts in PB (%) at weeks 1, 2, and 3 for PBS vs. control-MAYTL4PADC vs. PTCRA-MAYTL4PADC. FIG. 19F shows, in bar graph form, normal T-cell counts at weeks 1, 2, and 3 for PBS vs. control-MAYTL4PADC vs. PTCRA-MAYTL4PADC. FIG. 19G provides, in tabular form, the values of FIG. 19A. FIG. 19H shows, in tabular form, the values of FIG. 19B.

DEFINITIONS

Figure 1B:
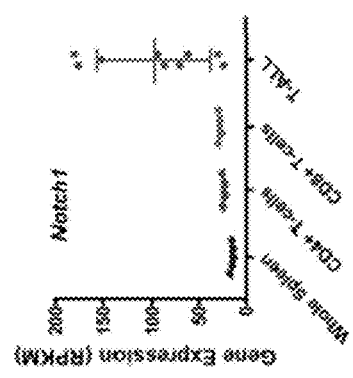
FIGS. 1A-1G demonstrate that genes associated with beta-selection and the DN to DP transition are upregulated in the thymic transplant model of T-ALL.
Figure 1C:
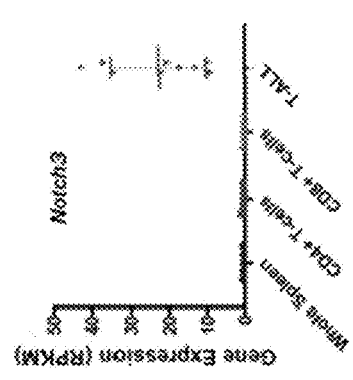
Figure 1D:
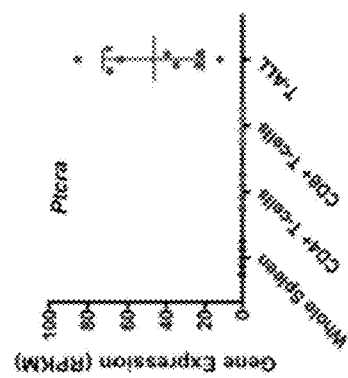

The expression Pre T-Cell Antigen Receptor Alpha (PTCRA) and the like, as used herein, refers to human Pre T-Cell Antigen Receptor Alpha, comprising the amino acid sequence, for example, as set forth in SEQ ID NOs:1 and 2. The expression "PTCRA" includes both monomeric and multimeric PTCRA molecules. As used herein, the expression "monomeric human PTCRA" means a PTCRA protein or portion thereof that does not contain or possess any multimerizing domains and that exists under normal conditions as a single PTCRA molecule without a direct physical connection to another PTCRA molecule. As used herein, the expression "dimeric human PTCRA" means a construct comprising two PTCRA molecules connected to one another through a linker, covalent bond, non-covalent bond, or through a multimerizing domain such as an antibody Fc domain.

The amino acid sequence of human PCTRA isoform X1 (NCBI XP_024302110.1) is the following:

```
                                          (SEQ ID NO: 1)
  1    mllvdgkqqm vvvclvldva ppgldspiwf sagngsalda ftygpspatd gtwtnlahls 61    lpseelaswe plvchtgpga eghsrstqpm hlsgeastar tcpqeplrgt pggalwlgvl 121    rlllfklllf dllltcsclc dpagplpspa tttrlralgs hrlhpatetg greatssprp 181    qprdrrwgdt ppgrkpgspv wgegsylssy ptcpaqawcs rsalrapsss lgaffagdlp 241    pplqagaa.
```

The amino acid sequence of human PCTRA isoform 2 precursor (NCBI NP_612153.2) is as follows:

```
                                          (SEQ ID NO: 2)
  1    magtwllll1 algcpalptg vggtpfpsla ppimllvdgk qqmvvvclvl dvappgldsp 61    iwfsagngsa ldaftygpsp atdgtwtnla hlslpseela sweplvchtg pgaeghsrst 121    qpmhlsgeas tartcpqepl rgtpggalwl gvlrlllfkl llfdllltcs clcdpagplp 181    spatttrlra lgshrlhpat etggreatss prpqprdrrw gdtppgrkpg spvwgegsyl 241    ssyptcpaqa wcsrsalrap ssslgaffag dlppplqaga a.
```

The shorter isoform lacks most of the extracellular domain.

All references to proteins, polypeptides and protein fragments herein are intended to refer to the human version of the respective protein, polypeptide or protein fragment unless explicitly specified as being from a non-human species. Thus, the expression "PTCRA" means human PTCRA, unless specified as being from a non-human species, e.g., "mouse PTCRA," "monkey PTCRA," etc.

As used herein, the expression "cell surface-expressed PTCRA" means one or more PTCRA protein(s), or the extracellular domain thereof, that is/are expressed on the surface of a cell in vitro or in vivo, such that at least a portion of a PTCRA protein is exposed to the extracellular side of the cell membrane and is accessible to an antigen-binding portion of an antibody. A "cell surface-expressed PTCRA" can comprise or consist of a PTCRA protein expressed on the surface of a cell that normally expresses PTCRA protein. Alternatively, "cell surface-expressed PTCRA" can comprise or consist of PTCRA protein expressed on the surface of a cell that normally does not express human PTCRA on its surface but has been artificially engineered to express PTCRA on its surface.

As used herein, the expression "anti-PTCRA antibody" includes both monovalent antibodies with a single specificity, as well as bispecific antibodies comprising a first arm that binds PTCRA and a second arm that binds a second (target) antigen. The expression "anti-PTCRA antibody" includes antibody-drug conjugates (ADCs) comprising an anti-PTCRA antibody or antigen-binding portion thereof conjugated to a therapeutic agent (for example, a drug or toxin, i.e., a cytotoxic agent). The expression "anti-PTCRA antibody" also includes antibody-radionuclide conjugates (ARCs) comprising an anti-PTCRA antibody or antigen-binding portion thereof conjugated to a radionuclide.

The term "antibody", as used herein, means any antigen-binding molecule or molecular complex comprising at least one complementarity determining region (CDR) that specifically binds to or interacts with a particular antigen (e.g., PTCRA). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-PTCRA antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody described in the present disclosure include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody described in the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the bispecific antibody formats described herein, may be adapted for use in the context of an antigen-binding fragment of an antibody in the present disclosure using routine techniques available in the art.

The antibodies mentioned herein may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) *Proc. Natl. Acad. Sci.* (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the anti-PTCRA antibodies of the ADCs are human antibodies. The term "human antibody", as used herein, is intended to include antibodies having variable and constant regions derived from human germline immunoglobulin sequences. The human antibodies of the ADCs of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the ADCs of the disclosure may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four-chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) *Molecular Immunology* 30:105) to levels typically observed using a human IgG1 hinge. The instant disclosure encompasses antibodies having one or more mutations in the hinge, $C_H2$ or $C_H3$ region that may be desirable, for example, in production, to improve the yield of the desired antibody form.

The antibodies of the ADCs disclosed herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-PTCRA antibodies of the ADCs disclosed herein may comprise one or more amino acid substitutions, insertions, and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The ADCs of the present disclosure include antibodies, and antigen-binding fragments thereof, which are derived from any of the amino acid sequences of antibodies described herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences of antibodies employed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the ADCs of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are employed within the present disclosure.

The present disclosure also includes ADCs comprising anti-PTCRA antibodies comprising variants of any of the full, HCVR, LCVR, and/or CDR amino acid sequences of the antibodies mentioned herein having one or more conservative substitutions. For example, the present disclosure includes ADCs comprising anti-PTCRA antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences of the antibodies mentioned herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) *Methods Mol. Biol.* 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) *Science* 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) *J. Mol. Biol.* 215:403-410 and Altschul et al. (1997) *Nucleic Acids Res.* 25:3389-402, each herein incorporated by reference.

Anti-PTCRA Antibody-Drug Conjugates

Provided herein are antibody-drug conjugates (ADCs) comprising an antibody or antigen-binding fragment thereof that specifically binds pre-T-cell antigen receptor alpha (PTCRA), wherein the antibody or antigen binding fragment thereof is conjugated to a therapeutic moiety, such as, without limitation, a cytotoxic agent, a chemotherapeutic drug, an immunomodulatory drug, or a radioisotope.

In some embodiments, the antibody-drug-conjugates have the following structure:

Ab-[L-Pay]$_n$ wherein:
Ab is an anti-PTCRA antibody or antigen-binding fragment thereof;
L is a linker;
Pay (or, payload) is a therapeutic moiety; and
n is an integer from 1-10.

Antibodies

The antibody-drug conjugates provided herein comprise an anti-PTCRA antibody or antigen-binding fragment thereof.

The anti-PTCRA antibodies can, in some embodiments, be fully human antibodies. Methods for generating monoclonal antibodies, including fully human monoclonal antibodies are known in the art. Any such known methods can be used in the context of the present disclosure to make human antibodies that specifically bind to human PTCRA.

The antibodies comprised in the ADCs disclosed herein can be full-length (for example, an IgG1 or IgG4 antibody) or may comprise only an antigen-binding portion (for example, a Fab, F(ab')2 or scFv fragment), and may be modified to affect functionality, e.g., to eliminate residual effector functions (Reddy, et al. 200, *J. Immunol.* 164:1925-1933).

Antibodies employed in the ADCs disclosed herein target PTCRA.

In some embodiments, the anti-PTCRA antibody included in the ADCs disclosed herein is 2F5 (*BD Biosciences*, catalog item no. 552407).

Public databases are also available for identifying CDR sequences within an antibody.

The present disclosure includes antibody-drug conjugates comprising anti-PTCRA antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield, et al. 2002 *JBC* 277:26733). In other applications, modification of galactosylation can be made in order to modify complement dependent cytotoxicity (CDC).

pH-Dependent Binding

The antibody-drug conjugates disclosed herein may employ anti-PTCRA antibodies with pH-dependent binding characteristics. Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen binding at acidic pH relative to neutral pH may be obtained.

Anti-PTCRA Antibodies Comprising Fc Variants

According to certain embodiments, the anti-PTCRA antibodies included in the ADCs disclosed herein comprise an Fc domain comprising one or more mutations that enhance or diminish antibody binding to the FcRn receptor, e.g., at acidic pH as compared to neutral pH. For example, the present disclosure includes anti-PTCRA antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present disclosure includes anti-PTCRA antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Antibodies

The present disclosure includes antibody-drug conjugates (ADCs) comprising antibodies and antigen-binding fragments thereof that specifically bind human PTCRA. Binding can be measured by surface plasmon resonance or a substantially similar assay.

The present disclosure includes antibody-drug conjugates (ADCs) comprising antibodies and antigen-binding fragments thereof that bind monomeric human PTCRA with high affinity. The present disclosure also includes antibody-drug conjugates (ADCs) comprising antibodies and antigen-binding fragments thereof that bind dimeric/multimeric human PTCRA with high affinity.

The present disclosure further includes antibody-drug conjugates (ADCs) comprising antibodies and antigen-binding fragments thereof that bind PTCRA and block Notch signaling in cells expressing human PTCRA. For example, the present disclosure includes antibody-drug conjugates (ADCs) comprising anti-PTCRA antibodies that block Notch signaling in cells that express human PTCRA, as measured using a Notch signaling blocking assay. Thus, the present disclosure includes antibody-drug conjugates (ADCs) that block Notch signaling in cells that express human PTCRA.

The present disclosure includes antibody-drug conjugates (ADCs) comprising antibodies and antigen-binding fragments thereof that bind PTCRA but do not block Notch signaling in cells expressing human PTCRA. As used herein, an antibody or antigen-binding fragment thereof "does not block" Notch signaling if, when tested in a Notch signaling blocking assay or a substantially similar assay, the antibody exhibits no or only negligible blocking activity. According to certain embodiments, an antibody or antigen-binding fragment "does not block" Notch signaling, if the antibody exhibits an 1050 value of greater than about 10 nM, or greater than about 100 nM, when tested in a Notch signaling blocking assay. Thus, in some embodiments, the present disclosure includes antibody-drug conjugates (ADCs) do not block Notch signaling in cells expressing human PTCRA.

The present disclosure includes antibody-drug conjugates (ADCs) comprising antibodies and antigen-binding fragments thereof that bind PTCRA and block pre-TCR signaling in cells expressing human PTCRA. For example, the present disclosure includes antibody-drug conjugates (ADCs) comprising anti-PTCRA antibodies that block pre-TCR signaling in cells that express human PTCRA, as measured using a pre-TCR signaling blocking assay. Thus, the present disclosure includes antibody-drug conjugates (ADCs) that block pre-TCR signaling in cells that express human PTCRA.

The present disclosure also includes antibody-drug conjugates (ADCs) comprising antibodies and antigen-binding fragments thereof that bind PTCRA but do not block pre-TCR signaling in cells expressing human PTCRA. As used herein, an antibody or antigen-binding fragment thereof "does not block" pre-TCR signaling if, when tested in a pre-TCR signaling blocking assay or a substantially similar assay, the antibody exhibits no or only negligible blocking activity. According to certain embodiments, an antibody or antigen-binding fragment "does not block" pre-TCR signaling, if the antibody exhibits an IC50 value of greater than about 10 nM, or greater than about 100 nM, when tested in a pre-TCR signaling blocking assay. Thus, in some embodiments, the present disclosure includes antibody-drug conjugates (ADCs) do not block pre-TCR signaling in cells expressing human PTCRA.

The antibodies comprised in the ADCs disclosed herein may possess one or more of the aforementioned biological characteristics, or any combination thereof. Thus, the ADCs disclosed herein may possess one or more of the aforementioned biological characteristics, or any combination thereof. The foregoing list of biological characteristics of the antibodies is not intended to be exhaustive. Other biological characteristics of the antibodies will be evident to a person of ordinary skill in the art from a review of the present disclosure including the working Examples herein.

Epitope Mapping and Related Technologies

The epitope to which the antibodies of the ADCs of the present disclosure bind may consist of a single contiguous sequence of 3 or more (e.g., 3, 4, 5, 6, 7, 8, 9, 10, 11, 12, 13, 14, 15, 16, 17, 18, 19, 20 or more) amino acids of a PTCRA protein. Alternatively, the epitope may consist of a plurality of non-contiguous amino acids (or amino acid sequences) of PTCRA.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, *Methods Mol Biol* 248:443-463), and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues, which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present disclosure further includes ADCs comprising anti-PTCRA antibodies that bind to the same epitope as any of the specific exemplary antibodies described herein. Likewise, the present disclosure also includes ADCs comprising anti-PTCRA antibodies that compete for binding to PTCRA with any of the specific exemplary antibodies described herein.

One can easily determine whether an antibody binds to the same epitope as, or competes for binding with, a reference anti-PTCRA antibody by using routine methods known in the art and exemplified herein. For example, to determine if a test antibody binds to the same epitope as a reference anti-PTCRA antibody described herein, the reference antibody is allowed to bind to a PTCRA protein. Next, the ability of the test antibody to bind to the PTCRA molecule is assessed. If the test antibody is able to bind to PTCRA following saturation binding with the reference anti-PTCRA antibody, it can be concluded that the test antibody binds to a different epitope than the reference anti-PTCRA antibody. On the other hand, if a test antibody is not able to bind to a PTCRA molecule following saturation binding with a reference anti-PTCRA antibody, then the test antibody may bind to the same epitope as the epitope bound by the reference anti-PTCRA antibody described herein. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans, et al., *Cancer Res.* 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-PTCRA antibody, the above-described binding methodology is performed in two orientations: In a first orientation, a reference antibody is allowed to bind to a PTCRA protein under saturating conditions followed by assessment of binding of a test antibody to the PTCRA molecule. In a second orientation, a test antibody is allowed to bind to a PTCRA molecule under saturating conditions followed by assessment of binding of a reference antibody to the PTCRA molecule. If, in both orientations, only the first (saturating) antibody is capable of binding to the PTCRA molecule, then it is concluded that the test antibody and the reference antibody compete for binding to PTCRA. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Bioequivalents

The antibody-drug conjugates comprise anti-PTCRA antibodies and antibody fragments that encompass proteins having amino acid sequences that vary from those of the described antibodies but that retain the ability to bind human PTCRA. Such variant antibodies and antibody fragments comprise one or more additions, deletions, or substitutions of amino acids when compared to parent sequence, but exhibit biological activity that is essentially equivalent to that of the described antibodies. Likewise, the anti-PTCRA antibody-encoding DNA sequences described herein encompass sequences that comprise one or more additions, deletions, or substitutions of nucleotides when compared to the disclosed sequence, but that encode an anti-PTCRA antibody or antibody fragment that is essentially bioequivalent to an anti-PTCRA antibody or antibody fragment included in an ADC disclosed herein. Such variant amino acid and DNA sequences are discussed above.

Bioequivalent variants of anti-PTCRA antibodies included in ADCs according to the disclosure may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-PTCRA antibody variants comprising amino acid changes that modify the glycosylation characteristics of the antibodies, e.g., mutations that eliminate or remove glycosylation.

Species Selectivity and Species Cross-Reactivity

The present disclosure, according to certain embodiments, provides antibody-drug conjugates comprising anti-PTCRA antibodies that bind to human PTCRA, but not to PTCRA from other species. The present disclosure also includes antibody-drug conjugates comprising anti-PTCRA antibodies that bind to human PTCRA and to PTCRA from one or more non-human species. For example, the ADCs disclosed herein may comprise anti-PTCRA antibodies that bind to human PTCRA and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee PTCRA. According to certain exemplary embodiments, the ADCs disclosed herein may comprise anti-PTCRA antibodies that specifically bind human PTCRA and cynomolgus monkey (e.g., *Macaca fascicularis*) PTCRA. Other ADCs disclosed herein may comprise anti-PTCRA antibodies that bind human PTCRA but do not bind, or bind only weakly, to cynomolgus monkey PTCRA.

Therapeutic Moieties

The antibody-drug conjugates (ADCs) provided herein comprise an anti-PTCRA antibody or antigen-binding fragment thereof conjugated to a therapeutic moiety. In some embodiments, the therapeutic moiety is a cytotoxic agent, a chemotherapeutic drug, an immunomodulatory drug, or a radioisotope.

Cytotoxic agents include any agent that is detrimental to the growth, viability or propagation of cells, including, but not limited to, tubulin-interacting agents and DNA-damaging agents. Examples of suitable cytotoxic agents and chemotherapeutic agents that can be conjugated to anti-PTCRA antibodies in accordance with this aspect of the disclosure include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins (e.g., calicheamicin γ1), camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin (e.g., dolastatin 10), doxorubicin, duocarmycin, echinomycins, eleutherobins, emetine, epothilones, esperamicin, estramustines, ethidium bromide, etoposide, fluorouracils, geldanamycins, gramicidin D, glucocorticoids, irinotecans, kinesin spindle protein (KSP) inhibitors, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PBDs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-PTCRA antibody is a maytansinoid. According to further embodiments, the maytansinoid is DM1 or DM4, a tomaymycin derivative, or a dolastatin derivative. According to still further embodiments, the maytansinoid is DM1. According to certain embodiments, the cytotoxic agent that is conjugated to an anti-PTCRA antibody is an auristatin. According to further embodiments, the auristatin is MMAE, MMAF, or derivatives thereof. According to still further embodiments, the auristatin is MMAE. Other cytotoxic agents known in the art are contemplated within the scope of the present disclosure, including, e.g., protein toxins such ricin, *C. difficile* toxin, pseudomonas exotoxin, ricin, diphtheria toxin, botulinum toxin, bryodin, saporin, pokeweed toxins (i.e., phytolaccatoxin and phytolaccigenin), and others such as those set forth in Sapra, et al., *Pharmacol. & Therapeutics,* 2013, 138:452-469. In another embodiment, the cytotoxic agent is a tubulysin. In another embodiment, the cytotoxic agent is a PBD.

In some embodiments, the cytotoxic agent is an auristatin.
In some embodiments, the cytotoxic agent is monomethyl auristatin E (MMAE).

In some embodiments, the cytotoxic agent is monomethyl auristatin F (MMAF).

In some embodiments, the cytotoxic agent is:

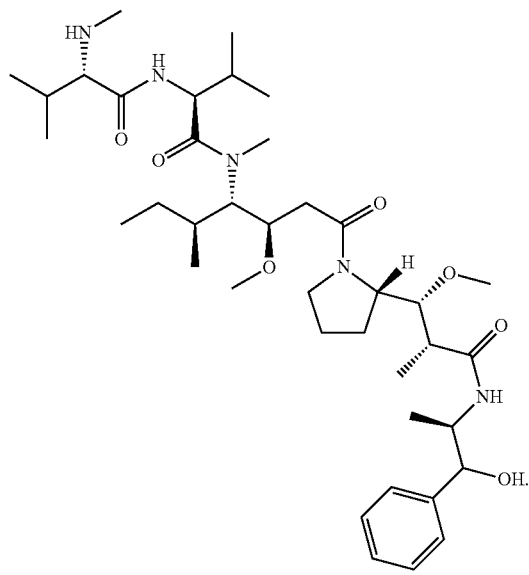 [SMILES: CC[C@H](C)[C@@H]([C@@H](CC(=O)N1CCC[C@H]1[C@H](OC)[C@@H](C)C(=O)N[C@H](C)C(O)c1ccccc1)OC)N(C)C(=O)[C@@H](NC(=O)[C@@H](NC)C(C)C)C(C)C]

In certain embodiments, the cytotoxic agent is a maytansinoid, e.g., derivative of maytansine. Suitable maytansinoids include DM1, DM4, or derivatives, stereoisomers, or isotopologues thereof. Suitable maytansinoids also include, but are not limited to, those disclosed in WO 2014/145090A1, WO 2015/031396A1, US 2016/0375147A1, and US 2017/0209591A1, incorporated herein by reference in their entireties.

In some embodiments, the maytansinoid has the following structure:

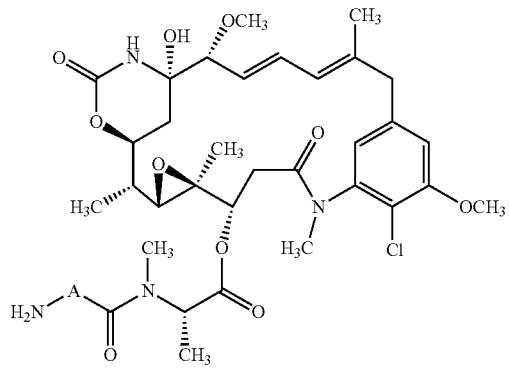

wherein A is an optionally substituted arylene or heteroarylene.

In some embodiments, the maytansinoid has the following structure:

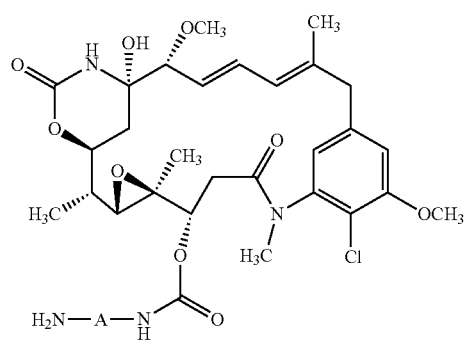

wherein A is an optionally substituted arylene or heteroarylene.

In some embodiments, the maytansinoid has the following structure:

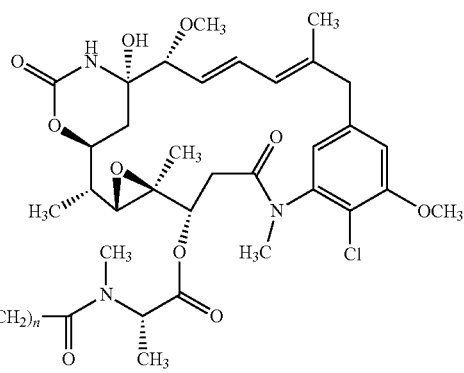

wherein n is an integer from 1-12 and $R^1$ is alkyl.

In some embodiments, the maytansinoid is:

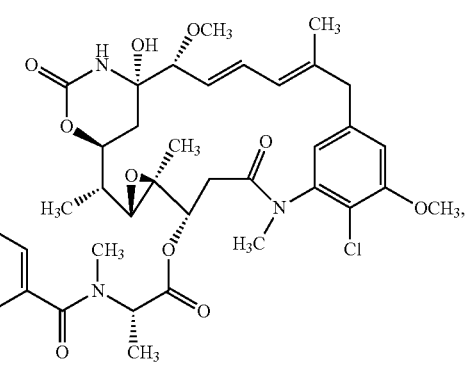

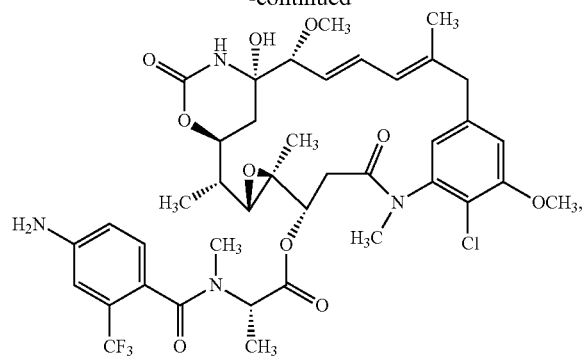
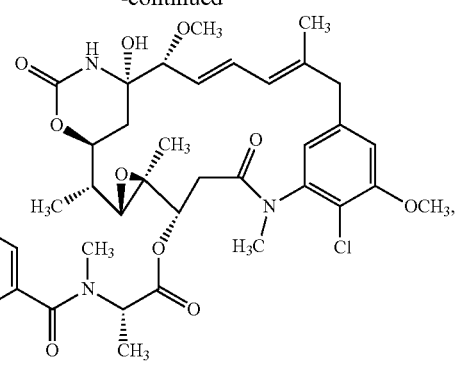
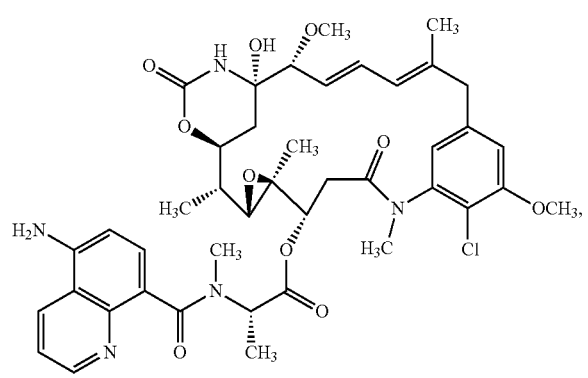
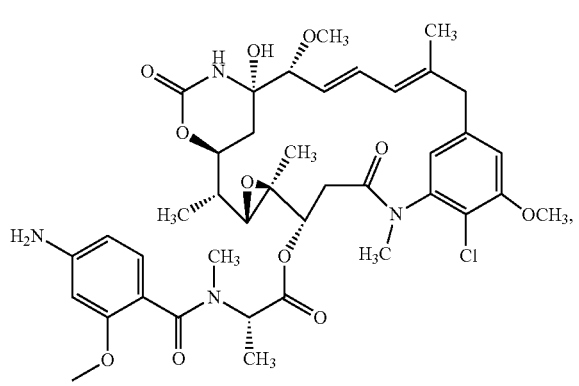
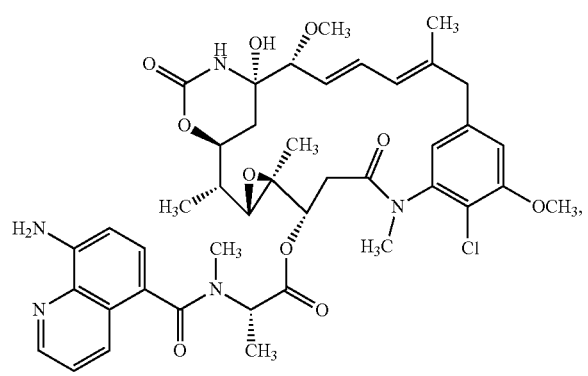
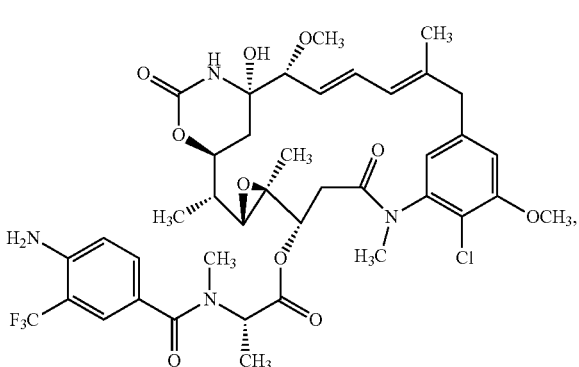
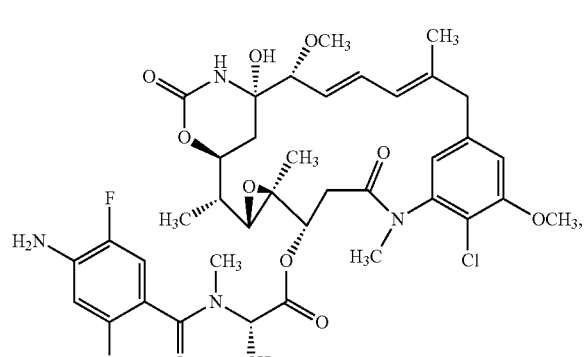
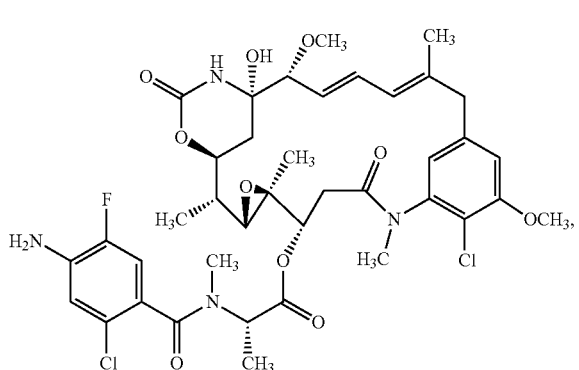

23
-continued
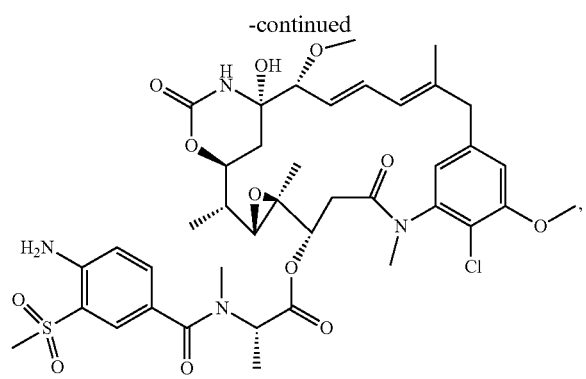
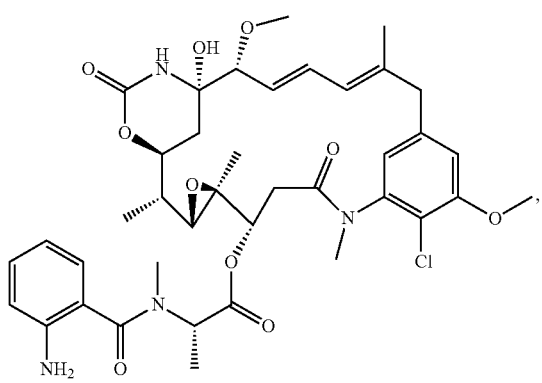
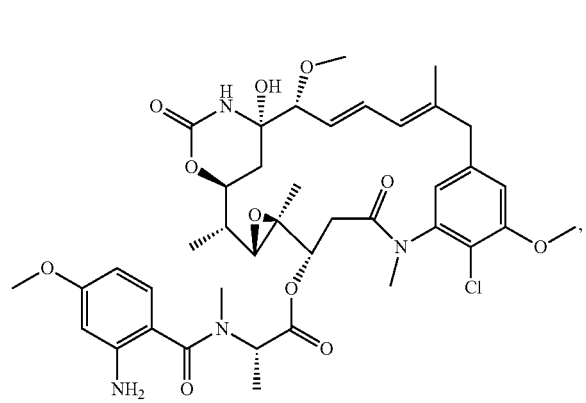
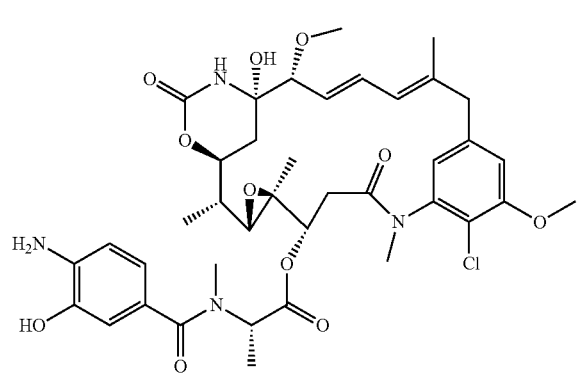
24
-continued
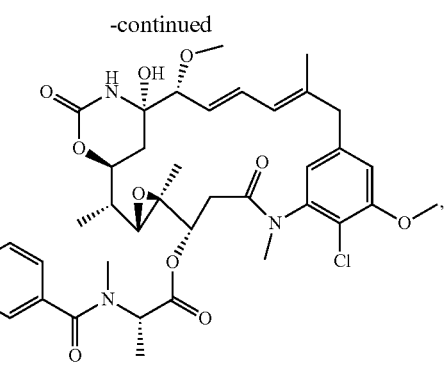
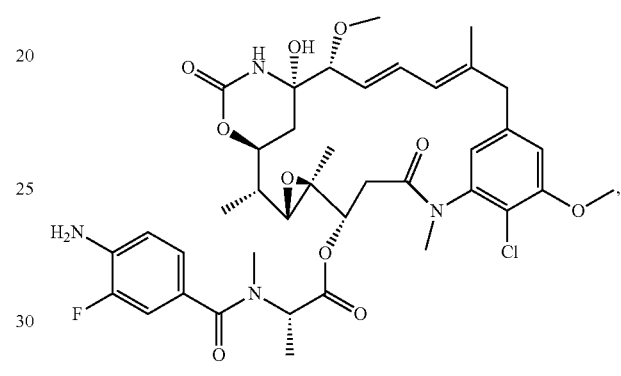
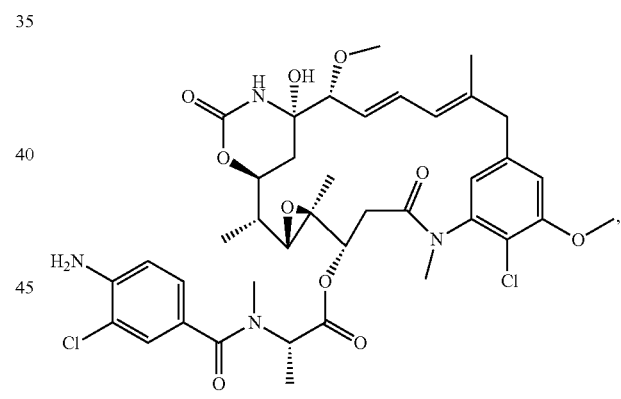
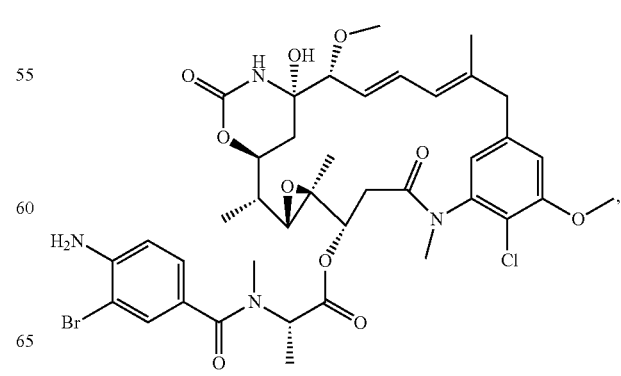

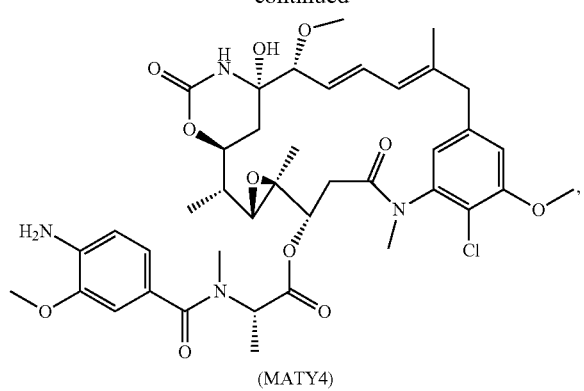
(MATY4)
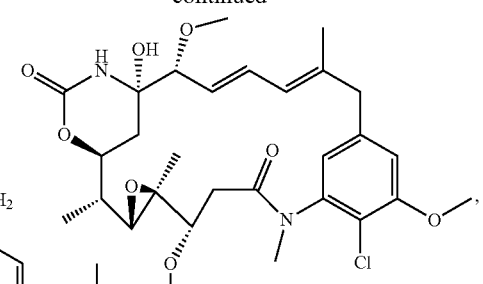
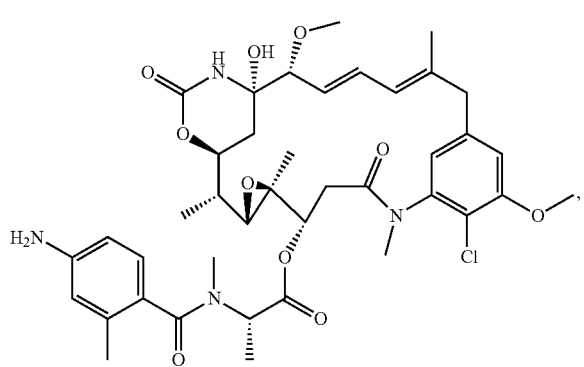
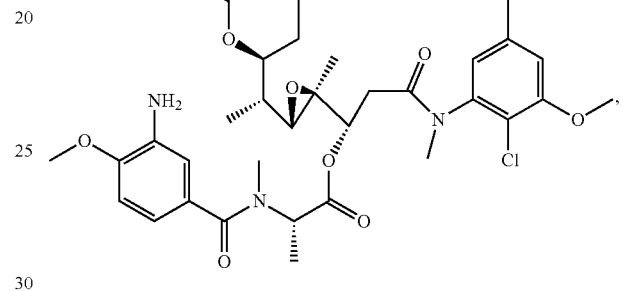
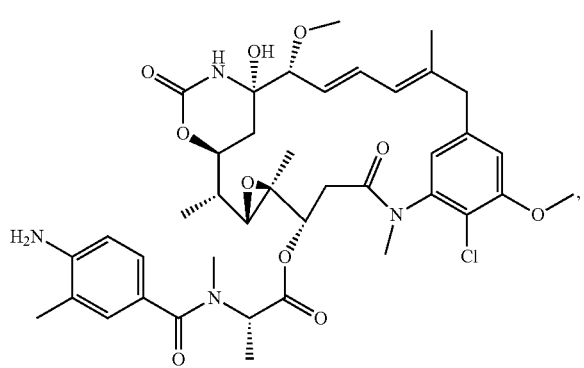
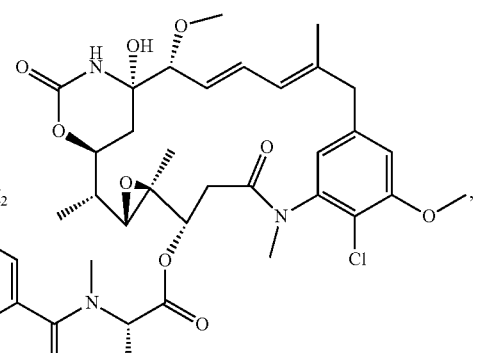
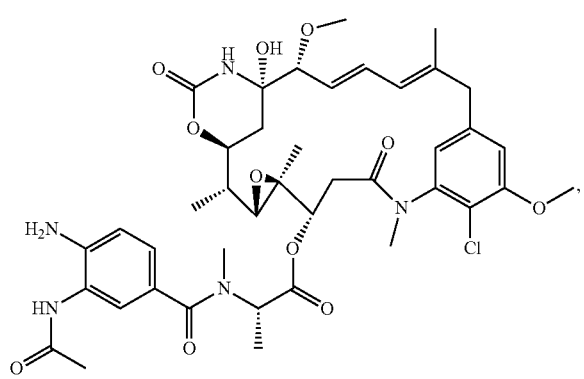
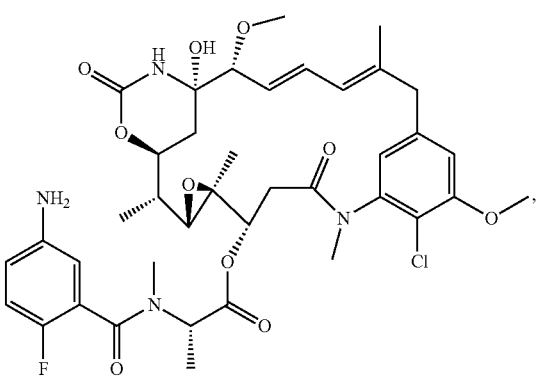

27
-continued
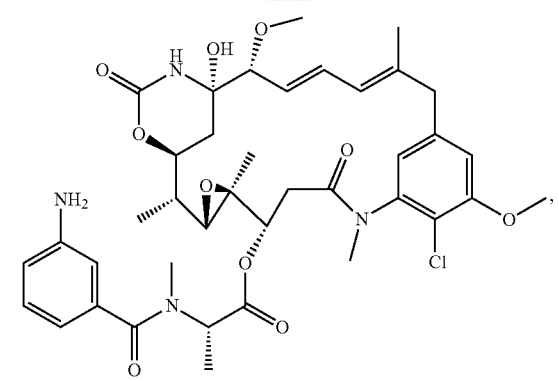
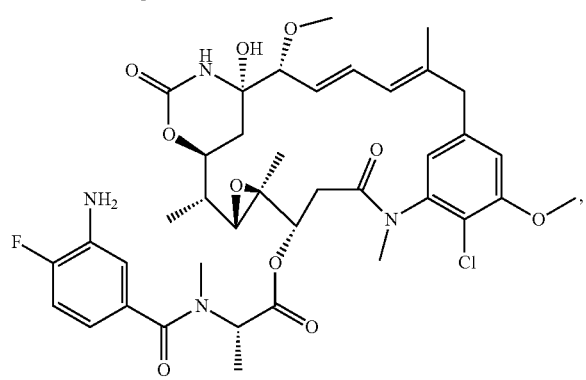
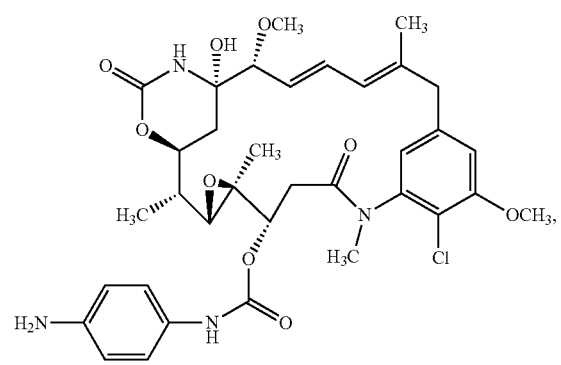
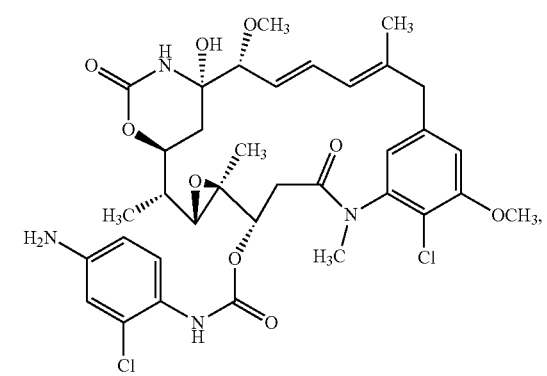
28
-continued
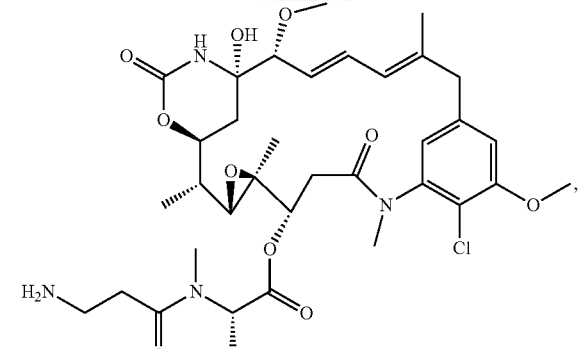
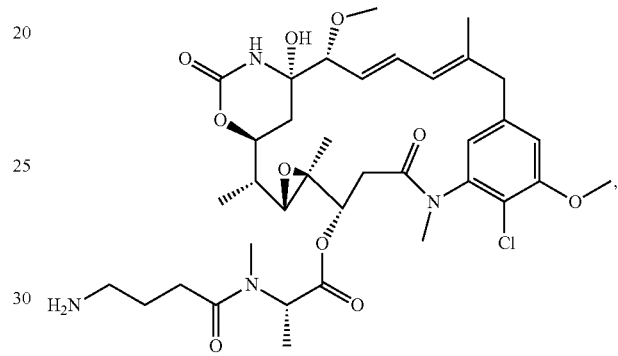
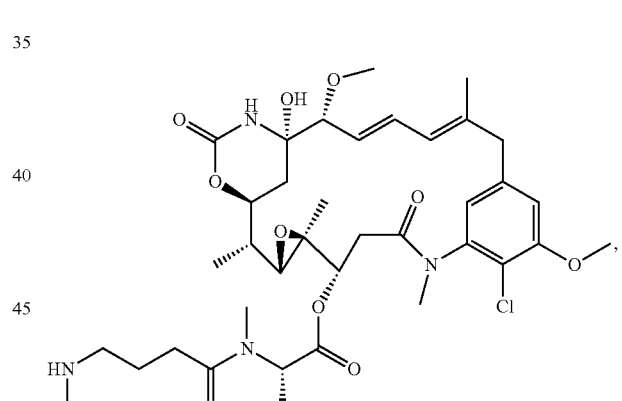
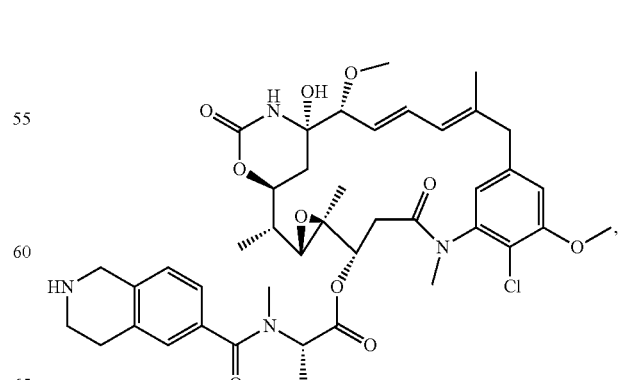
or -continued

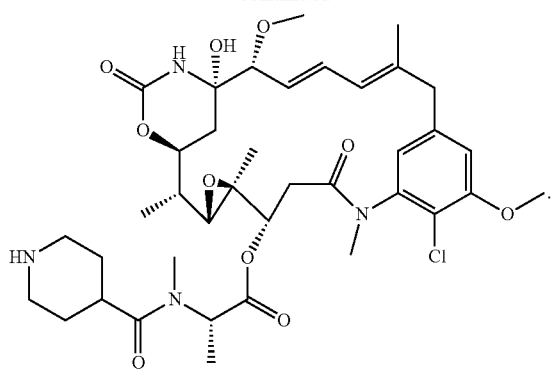

In some embodiments, the maytansinoid is

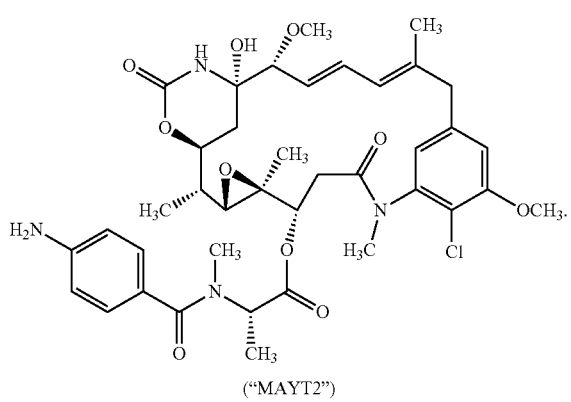 [SMILES: COc1cc2cc(c1Cl)N(C)C(=O)C[C@H](OC(=O)[C@H](C)N(C)C(=O)c1ccc(N)cc1)[C@]1(C)O[C@H]1[C@H](C)[C@@H]1C[C@@](O)(NC(=O)O1)[C@H](OC)/C=C/C=C(\C)C2]

("MAYT2")

In some embodiments, the maytansinoid is:

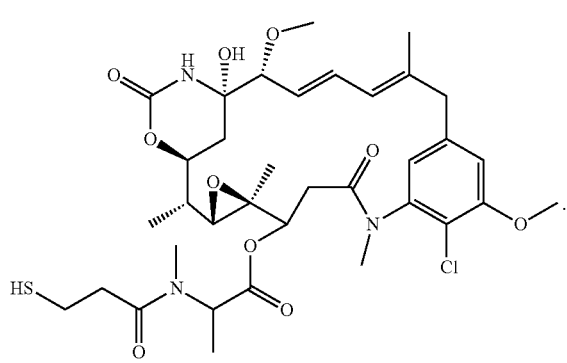 [SMILES: COc1cc2cc(c1Cl)N(C)C(=O)CC(OC(=O)C(C)N(C)C(=O)CCS)[C@]1(C)O[C@H]1[C@H](C)[C@@H]1C[C@@](O)(NC(=O)O1)[C@H](OC)/C=C/C=C(\C)C2]

In some embodiments, the maytansinoid is:

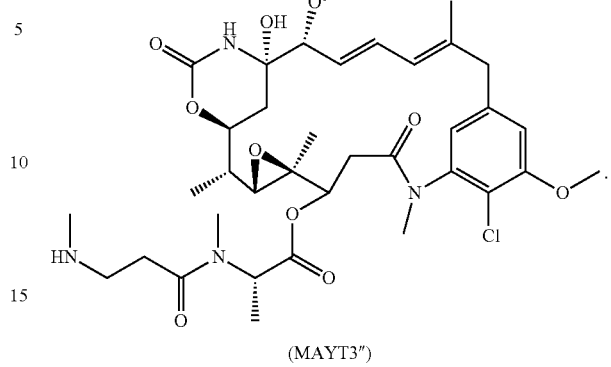

(MAYT3″)

Methods of preparing MAYT3 include those described in U.S. Pat. No. 10,570,151 B2.

In some embodiments, the maytansinoid is:

(MATY4)

The present disclosure also includes antibody-radionuclide conjugates (ARCs) comprising anti-PTCRA antibodies conjugated to one or more radionuclides. Exemplary radionuclides that can be used in the context of this aspect of the disclosure include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In some embodiments, the therapeutic moiety is <3000, <2000, <1000, or <900 daltons.

In certain embodiments, ADCs are provided herein comprising an anti-PTCRA antibody conjugated to a therapeutic moiety (e.g., any of the cytotoxic agents disclosed above) via a linker. Linkers are any group or moiety that links, connects, or bonds the antibody or antigen-binding proteins described herein with a therapeutic moiety, e.g. cytotoxic agent. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Linkers

Any linker or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, *Bioconjugate Chem.,* 2010, 21:5-13, and the references cited therein, the contents of which are incorporated by reference herein in their entireties. In certain embodiments, the linker is MC.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. Useful derivatives include p-aminobenzyloxycarbonyl (PABC). Those of skill will recognize that a self-immolative group is capable of carrying out a chemical reaction that releases the remaining atoms of a linker from a payload.

The present disclosure comprises ADCs in which a linker connects an anti-PTCRA antibody to a drug or cytotoxin through an attachment at a particular amino acid within the antibody or antigen-binding molecule. Exemplary amino acid attachments that can be used in the context of this aspect, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer, et al., *Proc. Natl. Acad. Sci.,* USA, 2008, 105:12451-12456), formyl glycine (see, e.g., Carrico, et al., *Nat. Chem. Biol.,* 2007, 3:321-322; Agarwal, et al., *Proc. Natl. Acad. Sci., USA,* 2013, 110:46-51, and Rabuka, et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan, et al., *Food & Agriculture Immunol.,* 2001, 13:127-130) and disulfide linkers (see, e.g., WO 2013/085925, WO 2010/010324, WO 2011/018611, and Shaunak, et al., *Nat. Chem. Biol.,* 2006, 2:312-313). Site-specific conjugation techniques can also be employed to direct conjugation to particular residues of the antibody or antigen binding protein (see, e.g., Schumacher, et al. *J Clin Immunol* (2016) 36(Suppl 1): 100). Site-specific conjugation techniques, include, but are not limited to, glutamine conjugation via transglutaminase (see, e.g., Schibli, *Angew Chemie Inter Ed.* 2010, 49, 9995).

According to certain embodiments, the present disclosure provides ADCs, wherein an anti-PTCRA antibody as described herein is conjugated to a linker-drug composition as set forth in International Patent Publication WO2014/145090, (e.g., the compound depicted below), the disclosure of which is hereby incorporated by reference herein in its entirety:

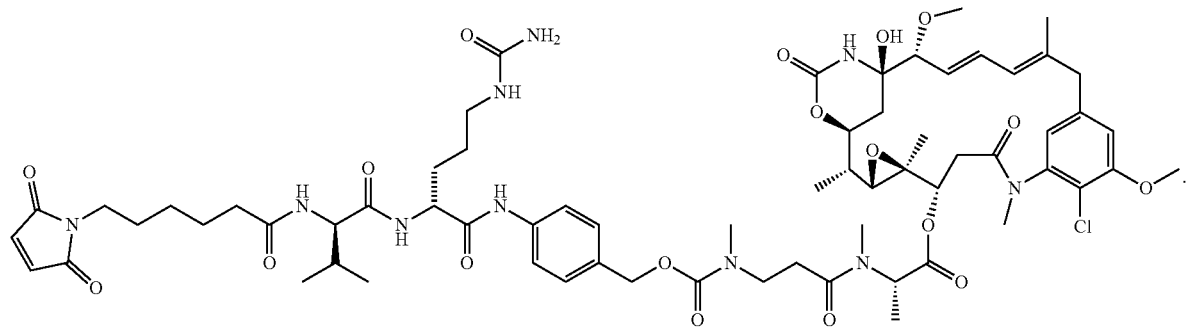

Thus, in some embodiments, the antibody-drug-conjugates have the following structure:

Ab-[L-Pay]$_n$ wherein:
Ab is an anti-PTCRA antibody;
L is a linker;
Pay is a therapeutic moiety; and
n is an integer from 1-10.
In certain embodiments, L is a non-cleavable linker.
In certain embodiments, Pay is a maytansinoid. In certain embodiments, Pay is DM1 or derivative thereof. In certain embodiments, Pay is:

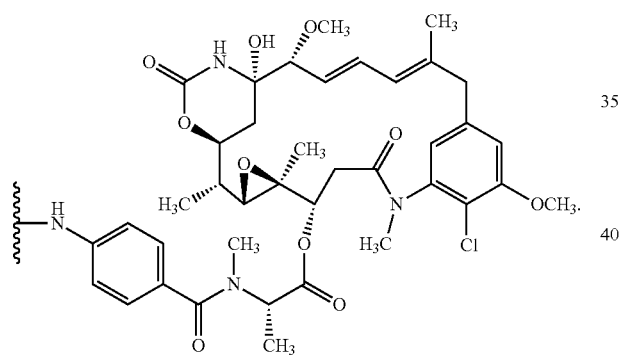

In certain embodiments, Pay is an auristatin. In certain embodiments, Pay is MMAE. In certain embodiments, Pay is MMAF.
In certain embodiments, the linker-payload (L-Pay) is:

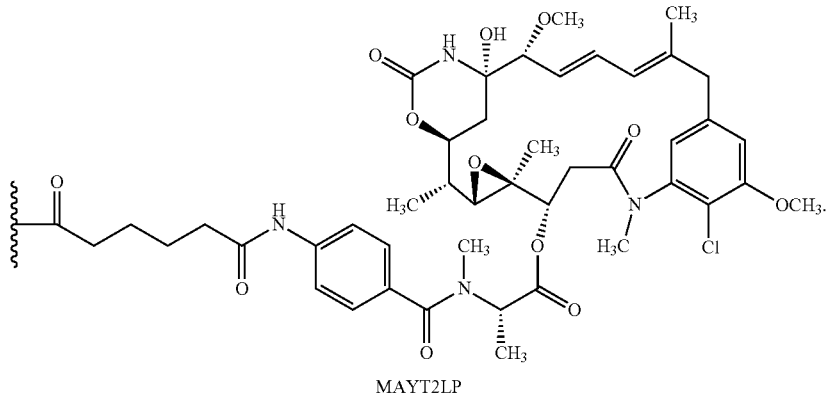 [SMILES: *C(=O)CCCCC(=O)Nc1ccc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)cc1]

MAYT2LP

In some embodiment, the linker-payload (L-Pay) is:

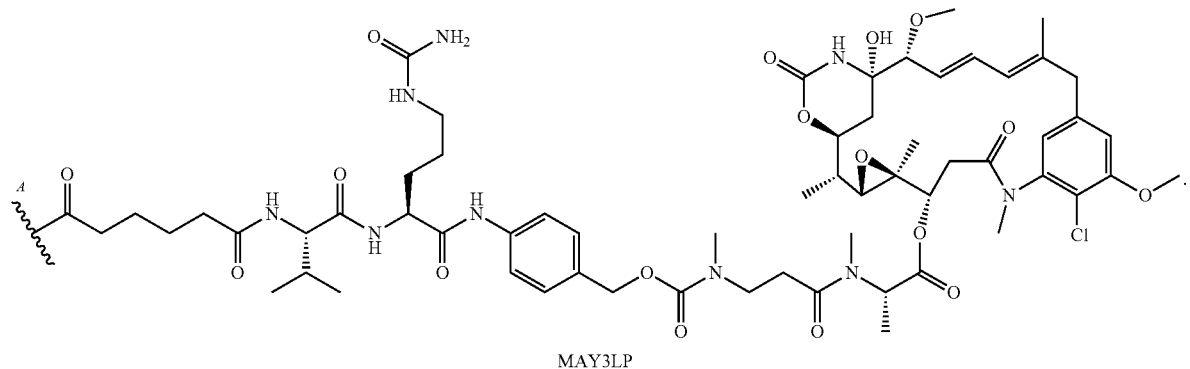

MAY3LP

In some embodiments, the linker-payload (LPay) is:

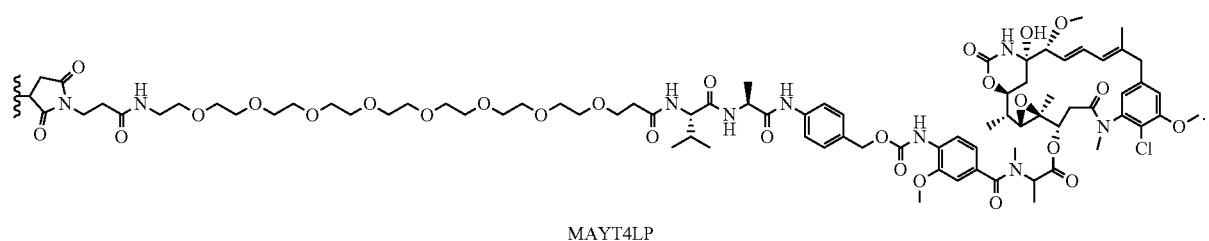 [SMILES: *C1CC(=O)N(CCC(=O)NCCOCCOCCOCCOCCOCCOCCOCCOCCC(=O)N[C@H](C(=O)N[C@@H](C)C(=O)Nc2ccc(COC(=O)Nc3ccc(C(=O)N(C)C(C)C(=O)O[C@H]4CC(=O)N(C)c5cc(cc(OC)c5Cl)C/C(C)=C/C=C/[C@@H](OC)[C@@]5(O)C[C@H](OC(=O)N5)[C@@H](C)[C@@H]5O[C@@]45C)cc3OC)cc2)C(C)C)C1=O]

MAYT4LP

In some embodiments, n is 1-6. In some embodiments, n is 1-5. In some embodiments, n is 1. In some embodiments, n is 2. In some embodiments, n is 3. In some embodiments, n is 4. In some embodiments, n is 5.

In some embodiments, the antibody-drug conjugate comprising MAYT2LP is prepared by contacting an anti-PTCRA antibody or antigen binding fragment thereof to a compound having the following structure:

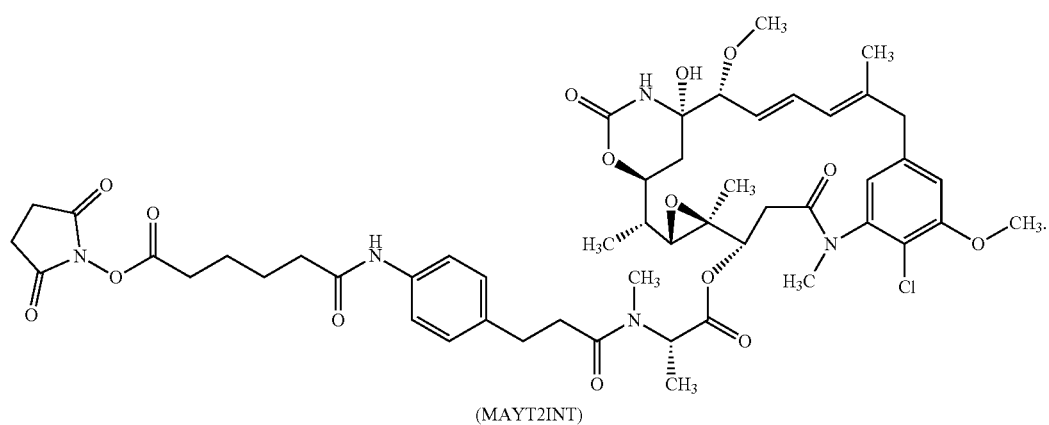

(MAYT2INT)

In some embodiments, the antibody-drug conjugate comprising MAYT3LP is prepared by contacting an anti-PTCRA antibody or antigen binding fragment thereof to a compound having the following structure:

forth in Example 7 herein. Variations on this exemplary method will be appreciated by persons of ordinary skill in the art and are contemplated within the scope of the present disclosure.

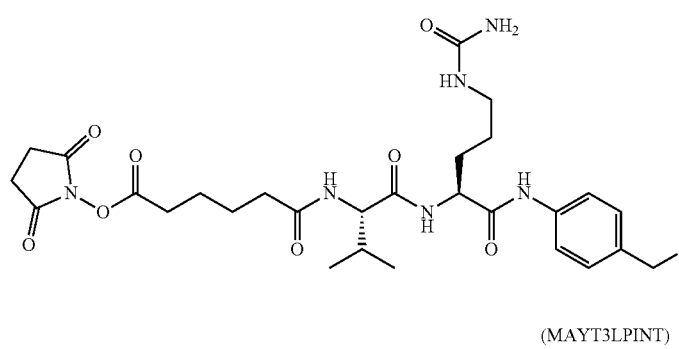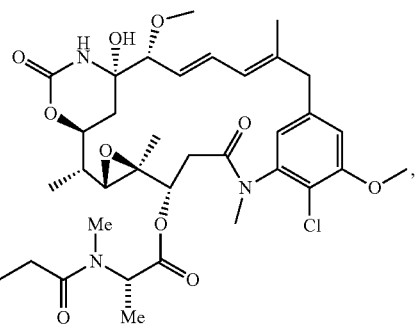

(MAYT3LPINT)

including, e.g., methods described in US Publication No. 2018/0134794 A1, which is incorporated herein by reference in its entirety.

In some embodiments, the antibody-drug conjugate comprising MAYT4LP is prepared by contacting an anti-PTCRA antibody or antigen binding fragment thereof to a compound having the following structure:

Characterization of Conjugates by Liquid Chromatography-Mass Spectrometry

Parameters that characterize an antibody-drug-conjugate (ADC) and determine its efficacy include, without limitation, its structure, stability, drug to antibody ratio (DAR), and payload distribution. DAR is a significant quality

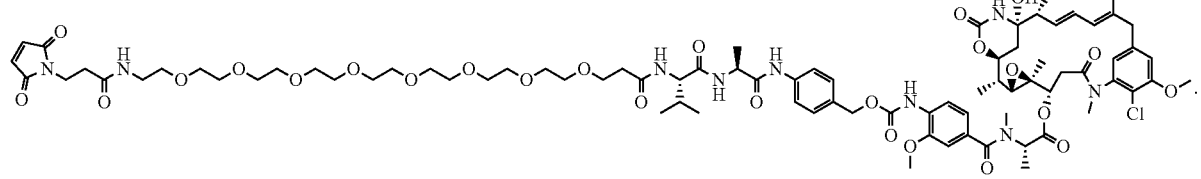

The antibody-drug conjugates described herein can be prepared using conjugation conditions known to those of ordinary skill in the art, (see, e.g., Doronina, et al., *Nature Biotechnology*, 2003, 21, 7, 778, which is incorporated herein by reference in its entirety). In some embodiments, an ADC comprising an anti-PTCRA antibody is prepared by contacting an anti-PTCRA antibody with a compound comprising the desired linker and cytotoxic agent, wherein said linker possesses a moiety that is reactive with the antibody or antigen-binding protein, e.g., at the desired residue of the antibody or antigen-binding protein.

According to certain embodiments, the present disclosure provides ADCs, wherein an anti-PTCRA antibody as described herein is conjugated to a linker-drug composition as set forth in International Patent Application No. PCT/US14/29757, filed on Mar. 14, 2014 (e.g., compound "7,"), the disclosure of which is hereby incorporated by reference herein in its entirety.

Any method known in the art for conjugating a chemical moiety to a peptide, polypeptide, or other macromolecule can be used in the context of the present disclosure to make an anti-PTCRA ADC as described herein. An exemplary method for antibody-drug conjugation via a linker is set parameter of an ADC and is presented as the average number of drug molecules conjugated to an antibody. The DAR value affects the efficacy of the drug, as low drug loading reduces the potency, while high drug loading can negatively affect pharmacokinetics (PK)1 and toxicity. DAR can be determined, for example, using Ultraviolet-Visible (UV/Vis) spectroscopy, Hydrophobic interaction chromatography (HIC), Reversed phase high-performance liquid chromatography (RP-HPLC), Liquid chromatography coupled with electrospray ionization mass spectrometry (LC-ESI-MS), and LC-MS.

In certain embodiments, to determine the loading of the linker-payloads on the antibody, the conjugates are deglycosylated and analyzed by LC-MS.

For the assay, 50 μg of the conjugate is diluted with milli-Q water to a final concentration of 1 mg/mL. Ten μL of PNGase F solution [PNGase F solution is prepared by adding 150 μL of PNGase F stock (New England Biolabs, Cat #P0704L) and 850 μL of milli-Q water and mixed well] is added to the diluted conjugate solution and then incubated at 37° C. overnight. Injections of 5 μL of each sample are made onto LC-MS (Waters Synat G2-Si) and eluted with 0.1 mL/minute of a gradient mobile phase 20-40% over 25 minutes (Mobile Phase A: 0.1% v/v FA in H2O; Mobile Phase B: 0.1% v/v FA in Acetonitrile). The LC separation is achieved on a Waters Acquity BEH C4 column (1.0×50 mM, 1.7 μM) at 80° C.

The mass spectrometry spectra are deconvoluted using Masslynx software, and the drug to antibody ratio (DAR) is calculated using the following equations:

1. Relative percentage (%) of drug (Dn) by distribution peak intensity (PI):

$$Dn\% = PIn/\Sigma(PI0+PI1+PI2 \ldots +PIi) \times 100$$

(n=0, 1, 2, 3, ..., i)

2. Average DAR calculation:

$$DAR = \Sigma(1 \times D1\% + 2 \times D2\% + 3 \times D3\% + \ldots + i \times Di\%)$$

In certain embodiments, the drug-antibody ratio (DAR) of the ADCs of the disclosure is between about 1 and about 30. In another embodiment, the DAR of the ADCs of the disclosure is between about 1 and about 8. In another embodiment, the DAR of the ADCs of the disclosure is between about 1 and about 6. In another embodiment, the DAR of the ADCs of the disclosure is between about 1 and about 5. In another embodiment, the DAR of the ADCs of the disclosure is between about 1 and about 4. In another embodiment, the DAR of the ADCs of the disclosure is between about 2 and about 4. In another embodiment, the DAR of the ADCs of the disclosure is about 1 or about 2 or about 3 or about 4 or about 5 or about 6 or about 7 or about 8 or about 9 or about 10 or about 11 or about 12 or about 13 or about 14 or about 15 or about 16 or about 17 or about 18 or about 19 or about 20 or about 21 or about 22 or about 23 or about 24 or about 25 or about 26 or about 27 or about 28 or about 29 or about 30.

Targeting ADCs to Cells Expressing PTCRA

In some embodiments, ADCs comprising an anti-PTCRA antibody conjugated to a cytotoxic agent described herein are able to specifically target and kill cells that express PTCRA. Specifically, ADCs comprising an anti-PTCRA antibody conjugated to a cytotoxic agent are able to specifically target and kill T-ALL cells. In some embodiments, the ADC kills T-ALL cells with an IC50 of about 1 pM to about 10 nM. In additional embodiments, the ADC kills T-ALL cells with an 1050 of about 1 nM to about 10 nM.

In some embodiments, PTCRA expression is detectable via flow cytometry on leukemic T cells. In additional embodiments, PTCRA expression is not detectable on normal, mature T-cells.

In Example 7, herein, it is shown that treatment of primary PTCRA+ murine T-ALL (mTALL) cells with i) a PTCRA-targeting mouse mAb, followed by treatment with anti-mouse IgG-Fc linked to the microtubule inhibitor monomethyl auristatin E (MMAE) via a non-cleavable linker, resulted in robust killing of mTALL cells, but no killing in control-treated cells (FIG. 16A); or ii) a PTCRA-targeting mAb directly conjugated to the microtubule inhibitor (MAYT2) via a non-cleavable linker (PTCRA-ADC, but not control-ADC) promoted dose-dependent killing of leukemic cells with an IC50 in the low nanomolar range (FIG. 16B). Of note, the PTCRA-ADC selectively induced killing of human SupT1 T-ALL cells, but did not impact viability of B-ALL (NALM6) and AML (K562) cell lines (FIG. 16C). Furthermore, PTCRA-ADC treatment had no effect on the viability of normal, peripheral T cells, consistent with its selective expression pattern.

In a highly-aggressive, disseminated T-ALL in vivo model, T-ALL-bearing mice treated with the PTCRA-ADC exhibited statistically significantly reduced tumor burden, both in peripheral blood and spleen relative to control-ADC controls (FIGS. 16D and 16E). Thus, inventors surprisingly found that targeting the T-ALL cells with a cytotoxic ADC comprising an anti-PTCRA antibody could specifically eradicate tumor cells while sparing normal T cells.

A relatively low dose (about 1 nM to about 10 nM) of ADCs comprising an anti-PTCRA antibody conjugated to a cytotoxic agent was shown herein to be sufficient to specifically target and kill T-ALL cells (FIG. 16B).

Accordingly, the present disclosure provides antibody-drug conjugates (ADCs) comprising an antibody or antigen-binding fragment thereof that specifically binds human PTCRA conjugated to a cytotoxic agent, wherein the ADCs effectively kill T-ALL cells. The methods according to this aspect of the disclosure comprise contacting the cells with an antibody-drug conjugate (ADC) comprising an anti-PTCRA antibody conjugated to a cytotoxic agent. "Contacting the cells" can be carried out in vitro, or in vivo, e.g., by administering an anti-PTCRA ADC to a subject in need thereof, wherein the administration causes the ADC to come into contact with cells expressing PTCRA, specifically, T-ALL cells.

As used herein, "effective killing" means that the ADC exhibits an IC50 of less than about 20 nM, or less than or equal to about 10 nM (e.g., less than or equal to about 9 nM, less than or equal to about 8 nM, less than or equal to about 7 nM, less than or equal to about 6 nM, less than or equal to about 5 nM, or less than or equal to about 4 nM) in a tumor cell killing assay, such as the assay defined in Example 7 herein, or a substantially similar assay. According to this aspect of the disclosure, the anti-PTCRA antibody component of the ADC can be any anti-PTCRA antibody, including those described herein. Additionally, the cytotoxic agent component of the ADC can be any cytotoxic agent, such as DM1, or any other cytotoxic agent mentioned herein.

ADCs of the present disclosure are able to inhibit tumor growth and/or reduce tumor size in PTCRA+ tumor-bearing animals. For example, as shown in Example 7 herein, anti-PTCRA ADCs were shown to significantly reduce tumors in mice bearing T-ALL tumors. Thus, the present disclosure includes ADCs comprising such anti-PTCRA antibodies, wherein the ADCs, when administered to a PTCRA+ tumor-bearing animal, inhibit tumor growth and/or reduce tumor size (e.g., tumor growth inhibition of 100% or greater) by Day 12 post-administration or sooner.

Therapeutic Formulation and Administration

The disclosure provides pharmaceutical compositions comprising antibody-drug conjugates (ADCs) comprising anti-PTCRA antibodies or antigen-binding fragments thereof, as disclosed herein. The pharmaceutical compositions of the disclosure are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell, et al. "Compendium of excipients for parenteral formulations" PDA (1998) *J Pharm Sci Technol* 52:238-311.

The dose of ADC administered to a patient may vary depending upon the age and the size of the patient, target disease, conditions, route of administration, and the like. The preferred dose is typically calculated according to body weight or body surface area. In an adult patient, it may be advantageous to intravenously administer the ADC of the present disclosure normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering ADCs may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu, et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

An antibody-drug conjugate comprising an antibody of an antigen-binding fragment thereof or a pharmaceutical composition of the present disclosure may be contained in a container selected from the group consisting of, but not limited to, a syringe, a vial, a pen delivery device, an autoinjector, or a microinfusor. In certain embodiments, the syringe or the pen delivery device may be pre-filled. In other embodiments, the vial may be a glass vial. An ADC comprising an antibody of an antigen-binding fragment thereof or a pharmaceutical composition of the present disclosure can be delivered subcutaneously or intravenously with a standard needle and syringe. In addition, with respect to subcutaneous delivery, a pen delivery device readily has applications in delivering an ADC comprising an antibody of an antigen-binding fragment thereof or a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present disclosure include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, an ADC comprising an antibody of an antigen-binding fragment thereof or a pharmaceutical composition of the present disclosure can be delivered in a controlled release system. In one embodiment, a pump may be used (see Langer, supra; Sefton, 1987, *CRC Crit. Ref. Biomed. Eng.* 14:201). In another embodiment, polymeric materials can be used; see, *Medical Applications of Controlled Release*, Langer and Wse (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

In some embodiments, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid ADC contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses

The present disclosure includes methods comprising administering to a subject in need thereof a therapeutic composition comprising an antibody-drug conjugate comprising an anti-PTCRA antibody or antigen-binding fragment thereof. The therapeutic composition can comprise any of the ADCs disclosed herein and a pharmaceutically acceptable carrier or diluent.

The ADCs of the disclosure are useful, inter alia, for the treatment, prevention and/or amelioration of any disease or disorder associated with or mediated by PTCRA expression or activity, or treatable by blocking the interaction between PTCRA and another molecule or otherwise inhibiting PTCRA activity and/or signaling, and/or promoting receptor internalization and/or decreasing cell surface receptor number. In one embodiment, the ADCs of the disclosure are useful, inter alia, for the treatment, prevention and/or amelioration of T-ALL. For example, the ADCs of the present disclosure are useful for the treatment of tumors that express PTCRA and/or that respond to Notch- or pre-TCR-mediated signaling, e.g., T-ALL tumors. The ADCs of the present disclosure may also be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the ADCs of the disclosure are used to treat one or more of the following cancers: renal cell carcinoma, pancreatic carcinoma, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, breast cancer, or melanoma.

In the context of the methods of treatment described herein, the ADC comprising an anti-PTCRA antibody or antigen-binding fragment thereof may be administered as a monotherapy (i.e., as the only therapeutic agent) or in combination with one or more additional therapeutic agents (examples of which are described elsewhere herein).

The present disclosure includes methods for identifying patients who are treatable with an ADC disclosed herein by assaying for high levels of PTCRA expression in one or more tissues of the patient, such as a tumor tissue. In a related embodiment, the present disclosure includes methods for treating cancers characterized by high-level expression of PTCRA, e.g. T-ALL. For example, the present disclosure includes methods of treatment comprising administering an ADC comprising an anti-PTCRA antibody or antigen-binding fragment thereof, to a subject with a tumor, wherein the tumor has been identified as expressing PTCRA. In certain embodiments, the tumor is identified as expressing PTCRA by immunohistochemistry of a biopsy sample or other imaging techniques such as, e.g., immuno-PET imaging, etc. In certain embodiments, a combination of FACS (positive or negative) and RNA sequencing is used to determine whether or not PTCRA is expressed. In further embodiments, cells positive for expression show >5 RPKM.

Combination Therapies and Formulations

The present disclosure includes compositions and therapeutic formulations comprising any of the ADCs described herein in combination with one or more additional therapeutically active components, and methods of treatment comprising administering such combinations to subjects in need thereof.

The ADCs of the present disclosure may be co-formulated with and/or administered in combination with one or more additional therapeutically active component(s) selected from the group consisting of: an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a PTCRA antagonist (e.g., another anti-PTCRA antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, —B, —C, or -D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), etc. Other agents that may be beneficially administered in combination with ADCs of the disclosure include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present disclosure includes compositions and therapeutic formulations comprising any of the ADCs described herein in combination with one or more chemotherapeutic agents. Examples of chemotherapeutic agents include alkylating agents such as thiotepa and cyclophosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The ADCs of the disclosure may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an ADC of the present disclosure; (for purposes of the present disclosure, such administration regimens are considered the administration of an ADC comprising an anti-PTCRA antibody or antigen-binding fragment thereof "in combination with" an additional therapeutically active component). The present disclosure includes pharmaceutical compositions in which an ADC of the disclosure is co-formulated with one or more of the additional therapeutically active component(s) as described elsewhere herein.

Administration Regimens

According to certain embodiments of the present disclosure, multiple doses of an antibody-drug conjugate (ADC) comprising an anti-PTCRA antibody or antigen-binding fragment thereof (or a pharmaceutical composition comprising such an ADC) may be administered to a subject over a defined time course. The methods according to this aspect of the disclosure comprise sequentially administering to a subject multiple doses of an ADC or composition of the disclosure. As used herein, "sequentially administering" means that each dose of ADC or composition is administered to the subject at a different point in time, e.g., on different days separated by a predetermined interval (e.g., hours, days, weeks or months). The present disclosure includes methods that comprise sequentially administering to the patient a single initial dose of an ADC or composition, followed by one or more secondary doses of the ADC or composition, and optionally followed by one or more tertiary doses of the ADC or composition.

The terms "initial dose," "secondary doses," and "tertiary doses," refer to the temporal sequence of administration of the ADC or composition of the disclosure. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of ADC or composition, but generally may differ from one another in terms of frequency of administration. In certain embodiments, however, the amount of ADC or composition contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of ADC or composition that is administered to a patient prior to the administration of the very next dose in the sequence with no intervening doses.

The methods according to this aspect of the disclosure may comprise administering to a patient any number of secondary and/or tertiary doses of an ADC comprising an anti-PTCRA antibody or antigen-binding fragment thereof or a composition comprising such an ADC. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

EXAMPLES

The following examples are put forth so as to provide those of ordinary skill in the art with a complete disclosure and description of how to make and use the methods and compositions of the disclosure, and are not intended to limit the scope of what the inventors regard as their disclosure. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Materials and Methods Employed in the Examples are the Following:

Thymus Transplantation Surgeries and Recipient Analysis

Single thymic lobes from newborn donor mice were surgically engrafted at the poles of the left kidney of host mice as previously described. Briefly, a small incision was made in the peritoneal cavity of the anesthetized host animal, exposing the left kidney. Using microdissection forceps and a stereo microscope, a single thymic lobe from the donor animal was positioned under the kidney capsule. The wound was then closed using surgical sutures and staples; the mice were routinely monitored for health status. All mouse experiments were performed with the approval of the Institutional Animal Care and Research Advisory Committee at Regeneron Pharmaceuticals.

Mice

Six- to eight-week-old Rag2$^{-/-}$ BALB/c (BRG) mice were purchased from Taconic and used as recipient hosts in thymic transplant experiments. Donor thymic lobes were isolated from C57BL6/6NTac mice purchased from Taconic or from Ptcra$^{-/-}$ or Notch3$^{-/-}$ mice generated at Regeneron using Velocigene® Technology.

Flow Cytometry Analysis

Tissues were harvested, and single cell suspensions were prepared in PBS with 3% fetal bovine serum. Antibody staining and FACS analysis was performed following standard protocols. The following monoclonal antibodies (mAbs) from Biolegend or BD Biosciences were used: anti-mCD45 (30-F11), anti-mCD4 (RM4-5), anti-mCD8a (53-6.7), anti-mCD44 (IM7), anti-mCD25 (PC61), anti-mPTCRA (2F5), anti-mNOTCH1 (mN1A and HMN1-12) and anti-mNOTCH3 (HMN3-133). Antibodies were directly coupled to FITC, PE, PerCPCy5.5, PECy7, APC, APC-Alexa Fluor 700, and Pacific blue. Data were acquired on BD Fortessa and analyzed by FlowJo.

Exome-Sequencing and Data Analysis

Whole exome capture was performed by using the Agilent Sure-Select Mouse All Exon 50 Mb kit, followed by 100 bp paired-end sequencing on the Illumina HiSeq 2000 platform. Read alignment and processing were performed using OSA aligner embedded in ArrayStudio. On average, around 80 million reads were generated for each sample, and over 65% are mapped on targets, which gives 80% of targets with more 20× read coverage depth. Mutation (including small insertion and deletion) calling cutoffs used were: at least 10% variant allele frequency and at least 5 variant reads from both strands. Complete details of the pipeline can be found online at www.arrayserver.com/wiki/. Somatic copy number variation patterns were estimated at the arm-level with whole exome sequencing (WES) data. Given DNA reads alignment input (BAM files) for a tumor sample and matched normal, the VarScan2 function embedded in Array-Studio (www.omicsoft.com; www.arrayserver.com) was utilized to calculate read coverage depth ratio (log 2Ratio) and summarize the copy number status. The average log 2Ratio values for every 100 kb sliding window per chromosome were displayed with Segment Chromosome View in Array-Studio. One normal sample from DKO spleen served as control for all tumors generated on DKO strain background.

Cell lines and Growth Conditions

SupT1, HPB-ALL, and Jurkat are human T-ALL cell lines obtained from ATCC and DSMZ. Cells were cultured in a base RPMI-1640 media, formulated per the recommendations of the supplier. Cells were seeded at a density of 3×105 cells/mL and passaged regularly to maintain a density of less than 2×106 cells/mL. For CRISPR experiments, the cell lines were stably transduced with Cas9 using Cas9-expressing lentivirus (Sigma-Aldrich). The cells were then transduced with either control or PTCRA-targeting gRNAs (Sigma-Aldrich). Transduction was performed following the manufacturer's suggested protocol. Knockout was confirmed by Western blot.

RNA-Sequencing and Data Analysis

Total RNA was converted to mRNA libraries using KAPA Stranded mRNA-Seq kits from KAPA Biosystems following the manufacturer's protocols. Libraries were sequenced by 100 bp paired-end reads on the Illumina HiSeq 2000. Read mapping, gene expression quantitation, and identification of fusion transcripts are calculated in ArrayStudio software. 75 million reads were generated for each sample with a unique mapping rate of 85% on average.

Analysis of Public Datasets

Expression of PTCRA in human T-ALL was examined in two independent datasets, for which RNA expression data is publicly available. The first dataset, the St. Jude Pediatric Cancer hematopoietic malignancies dataset, is a genomic database comprised of RNA-sequencing of tumor cells and other molecular phenotypes from 2,224 pediatric and young adult patient samples from B-ALL, AML, T-ALL and MLL indications. The samples are derived from the St. Jude—WashU Pediatric Cancer Genome Project, the Therapeutically Applicable Research to Generate Effective Treatments (TARGET) project and the Shanghai Children's Medical Center pediatric ALL project. It is part of an effort to apply a comprehensive genomic approach to determine molecular changes that drive childhood cancers. The data is accessed at: www.stjude.cloud/data.html. RNA-seq data from this dataset was processed through Omicsoft Array Studio Land data analysis pipeline, aligned with OSA (Omicsoft Aligner) to Human Genome Build B38 with Ensembl gene model, and then derived counts based with EM algorithm based on RSEM. Counts were converted to RPKM (Reads per Kilobase of transcript per Million mapped reads). Both gene-level and exon junction quantification were generated. Classification of T-ALL samples by subtype is per the hierarchal clustering of RNA-seq gene expression data, genomic alterations and expression of transcription factors described by Liu, et al. (2017 *Nat Genet* 49:1211-1218).

The second publicly available dataset used to examine the specificity of PTCRA expression in human T-ALL was an exploratory, retrospective stage I study which examined the whole-genome expression profiles of 2,096 patients pediatric and adult patients with leukemias and lymphomas by microarray analysis (Haferlach, et al. 2010 *J Clin Oncol* 28:2529-2537). Expression was quantified on a Human Genome U133 Plus 2.0 Array, measuring the expression of 19,574 genes across 54,675 reporters. Expression data for PTCRA (Reporter IS: 211252_x_at) was downloaded from Oncomine and processed and analyzed in Prism 7.

Expression of PTCRA in human cell lines was obtained from the Cancer Cell Line Encyclopedia, accessed at: portals.broadinstitute.org/ccle. The dataset is comprised of RNA-sequencing data for 1,457 cell lines across multiple tumor types. The sequencing was performed by the Broad Institute for the Cancer Cell Line Encyclopedia. Expression data for PTCRA across all cell liens in the data set was downloaded from CCLE and processed and analyzed in Prism 7.

Analysis of Patient Samples

Bone marrow and peripheral blood samples were prospectively collected from patients with acute leukemias through a contract research organization. All samples were obtained with the written, informed consent of each patient in accordance with the regulatory requirements set forth in the Good Clinical Practice guidelines of the International Council for Harmonization.

Figure 1E:
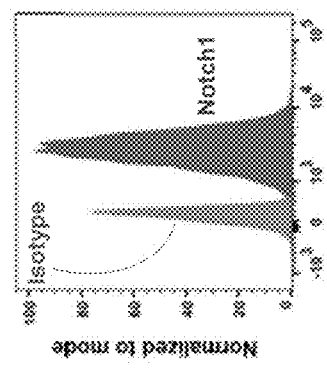
Figure 1F:
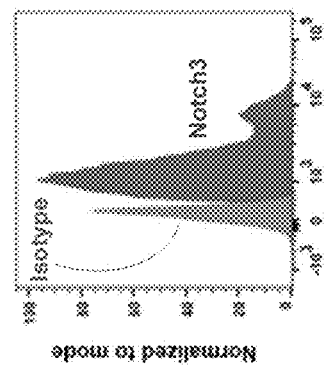
Figure 1G:
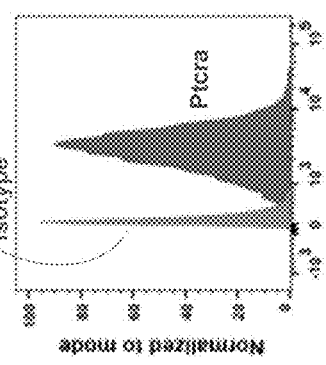
Figure 1A:
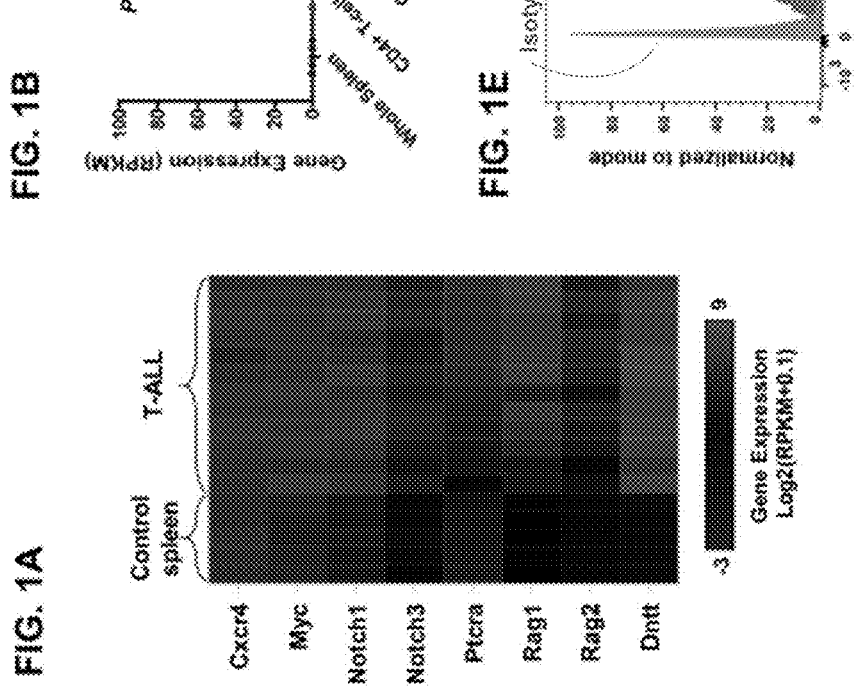

Example 1. Upregulation of β-Selection Checkpoint Factors in a Spontaneous T-ALL Model Murine T-ALL was generated by transplanting single thymic lobes derived from newborn wild type mice under the kidney capsule of immunodeficient, adult $Rag2^{-/-}$ $IL2Ryc^{-/-}$ hosts. Mice developed tumors with high penetrance and a median time to neoplastic disease of approximately 25 weeks, consistent with published results (Martins, et al. 2014 *Nature* 509:465-470). Leukemic disease generated with this model broadly recapitulated key features of human T-ALL, including splenomegaly, infiltration of blast cells into the bone marrow and a high frequency of gain-of-function Notch1 mutations ("Therapeutic targeting of Notch signaling and immune checkpoint blockade in a spontaneous, genetically-heterogeneous mouse model of T-cell acute lymphoblastic leukemia," Gao, et al., 2019 *Disease Models and Mechanisms*). Transcriptomes of these spontaneous tumors were analyzed by RNA-sequencing, comparing T-ALL tumors-infiltrated spleen to spleens of non-tumor bearing mice. Strong differential expression of multiple markers of thymocyte development was observed, including Dntt, Rag1 and Rag2 in T-ALL cases compared to control splenic tissue or purified peripheral CD4+ and CD8+ T cells (FIG. 1A; FIG. 2). Strong upregulation of genes associated with the β-selection checkpoint was also observed, including: Ptcra (369-fold), Notch3 (46-fold) and Notch1 (3.3-fold) (FIG. 1A-1D). Cell surface expression of these three genes in T-ALL blasts was confirmed by flow cytometry (FIG. 1E-1G). Because the β-selection checkpoint is a key step in thymocyte development, the upregulation of factors required for crossing the checkpoint may contribute to leukemogenesis in the instant animal T-ALL model.

Example 2. Arrested Thymocyte Development in Ptcra KO Mice

Figure 4B:
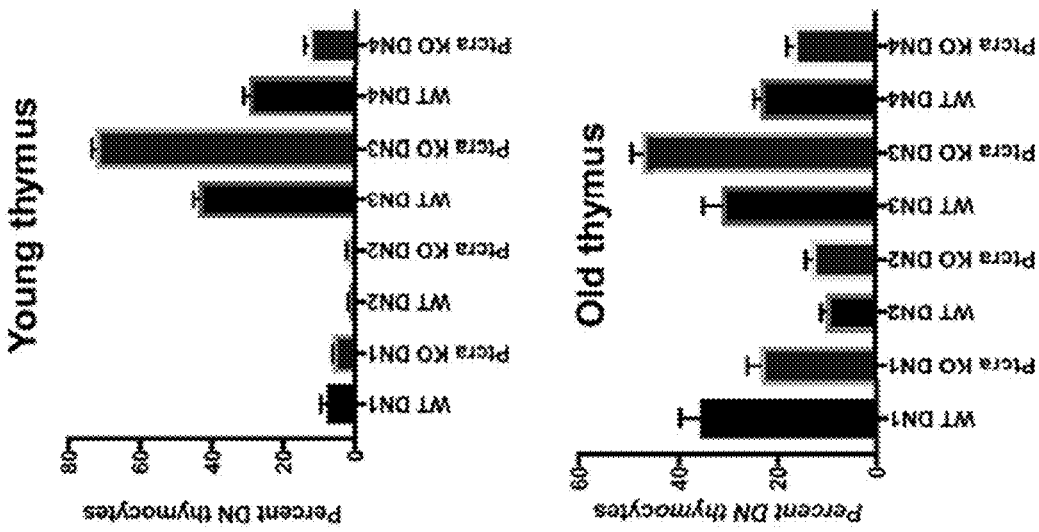
FIGS. 4A and 4B demonstrate that thymic hypoplasia in Ptcra KO mice is ameliorated with age.
Figure 4A:
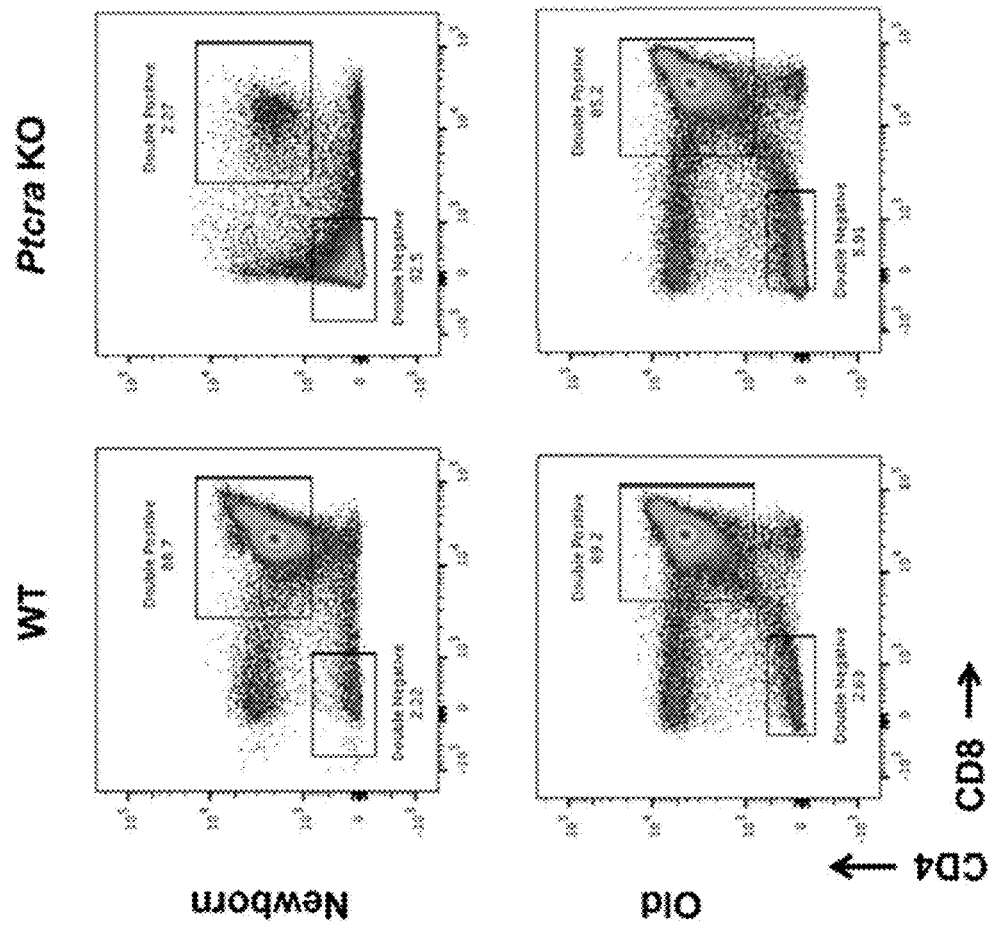

Notch1 is a canonical T-ALL oncogene (Grabher, et al. 2006 *Nat Rev Cancer* 6:347-359); transgenic mouse models have also suggested a role for Ptcra and Notch3 in T-ALL (Bellavia, et al. 2002 *PNAS* 99:3788-3793; Bellavia, et al. 2000 *EMBO J* 19:3337-3348; dos Santos, et al. 2007 *Blood* 109:3972-3981). To elucidate whether these latter genes contribute to leukemogenesis in a more physiologically relevant model, $Ptcra^{-/-}$ and $Notch3^{-/-}$ gene-targeted mice were created, and thymic lobes from these animals were used in transplantation studies. $Ptcra^{-/-}$ and $Notch3^{-/-}$ mice were generated by inserting a β-galactosidase gene in frame into the first coding exon of each gene. Neonatal $Ptcra^{-/-}$ mice developed thymic hypoplasia (FIG. 3A) (Fehling, et al. 1995 *Nature* 375:795-798; Mancini, et al. 1999 *J Immunol* 163:6053-6059). Immunoprofiling of these mice revealed a thymocyte compartment largely devoid of $CD4^+CD8^+$ DP cells, with most thymocytes arrested in the DN3 stage (FIGS. 3B and 3C). RT-PCR analysis revealed strong expression of canonical DN3 genes in $Ptcra^{-/-}$ thymi, relative to wild type control, including Notch3, Hes1, Dtx1, Hes5 and Notch1. Similarly, strong downregulation of DP markers, including Cd4 and Cd8, was observed (FIG. 3D). This thymic phenotype in $Ptcra^{-/-}$ mice was partially reversed by adulthood (FIGS. 4A and 4B). No striking thymic phenotypes were observed for $Notch3^{-/-}$ mice (FIG. 5). Thus, the role of the pre-TCR (the key DN3 to DN4 transition factor) in the leukemogenesis of T-ALL was validated.

Figure 6:
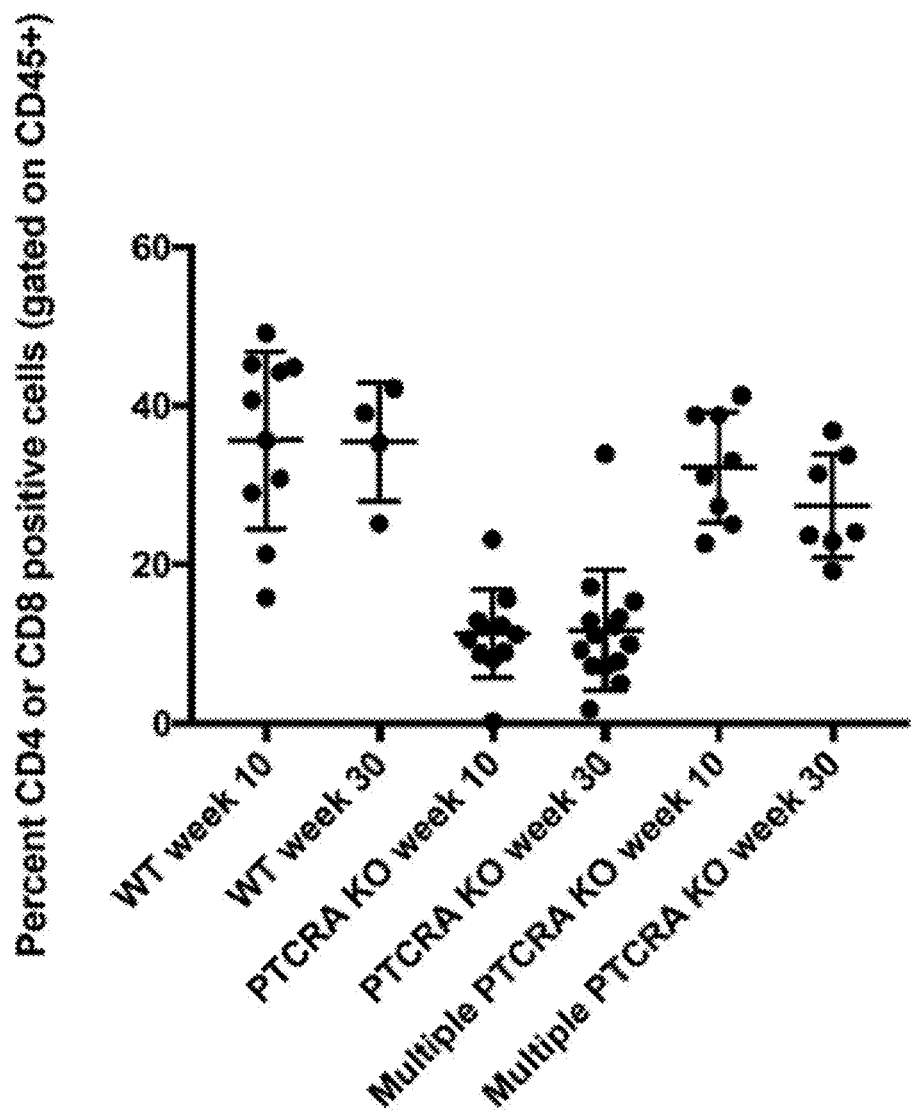
FIG. 6 demonstrates that Ptcra KO thymi maintained capacity for T-cell production following transplantation. Peripheral T-cell frequency was monitored by flow cytometry during the course of thymic transplantation studies. Values for single wild type (WT), Ptcra KO, and multiple (4-8) Ptcra KO donor thymi are plotted.
Figure 7A:
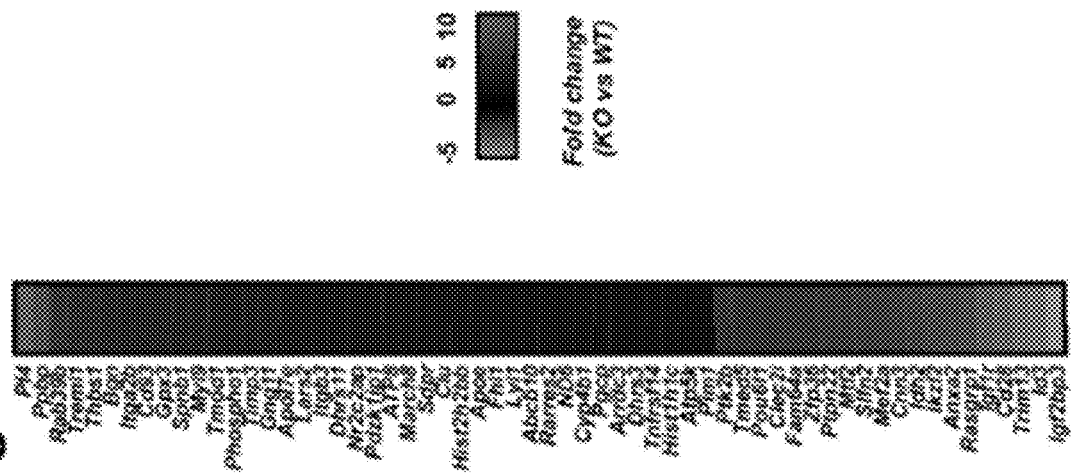
FIGS. 7A-7C demonstrate that genetic ablation of Ptcra results in impaired T-ALL development.

Example 3. Genetic Ablation of Ptcra Results in Markedly Impaired T-ALL Development To assess the effects of loss of pre-T cell receptor signaling on leukemogenesis, thymi from newborn $Ptcra^{-/-}$ mice were transplanted. To account for the reduced thymic cellularity in $Ptcra^{-/-}$ neonates, two lobes were used in each transplant. $Ptcra^{-/-}$ thymi grafted efficiently in $Rag2^{-/-}$ $IL2Ry^{-/-}$ hosts, as assessed by longitudinal monitoring of peripheral T cell levels (FIG. 6). Compared to wild type controls, Ptcra-deficient thymi exhibited a markedly reduced capacity to induce leukemogenesis. Overall disease penetrance was significantly decreased, and median time to neoplastic disease was not reached within 52-weeks (vs. 25 weeks for wild type controls, HR=0.249) (FIG. 7A). Increasing the number of $Ptcra^{-/-}$ thymic lobes that were used as donors in these transplants (up to 8 lobes) did not change the efficiency of leukemogenesis, indicating that differences in the cellularity between wild type and Ptcra$^{-/-}$ donor thymi was not driving these differences in T-ALL development (FIG. 7A).

Figure 7B:
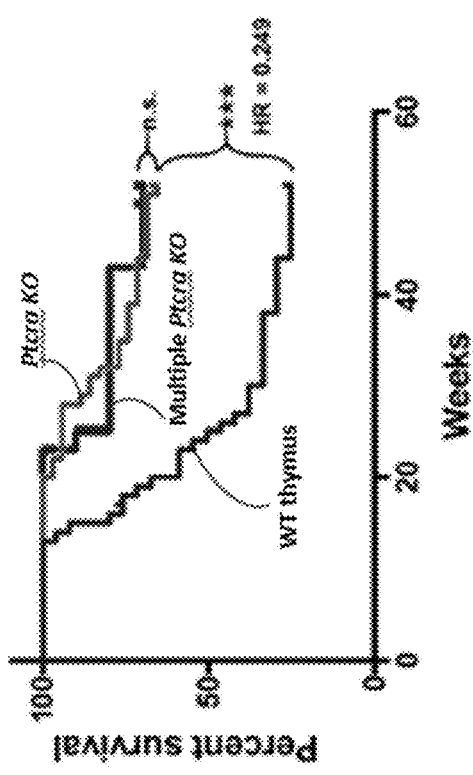

The Ptcra$^{-/-}$ leukemic disease that occasionally did develop was immunophenotypically comparable to wild type tumors and exhibited a similar, but slightly less pronounced nature of acute onset (FIG. 7B; data not shown). Molecular profiling of these tumors revealed a mutational spectrum largely consistent with wild type tumors, including recurrent mutations in the canonical T-ALL oncogene, Notch1 (Table 1, below).

TABLE 1

| Sample ID | No. of mutations | Notch1 5' truncation | Notch1 PEST mutation | Additional mutated genes of interest |
|---|---|---|---|---|
| Ptcra KO 1 | 12 | | + | Fat1, Ddx3x |
| Ptcra KO 2 | 16 | + | + | Ikzf1 |
| Ptcra KO 3 | 12 | + | | Fat1, Ptpn11 |
| Ptcra KO 4 | 40 | | + | |
| Ptcra KO 5 | 3 | + | | Rit1 |
| Ptcra KO 6 | 7 | | | |

Figure 7C:
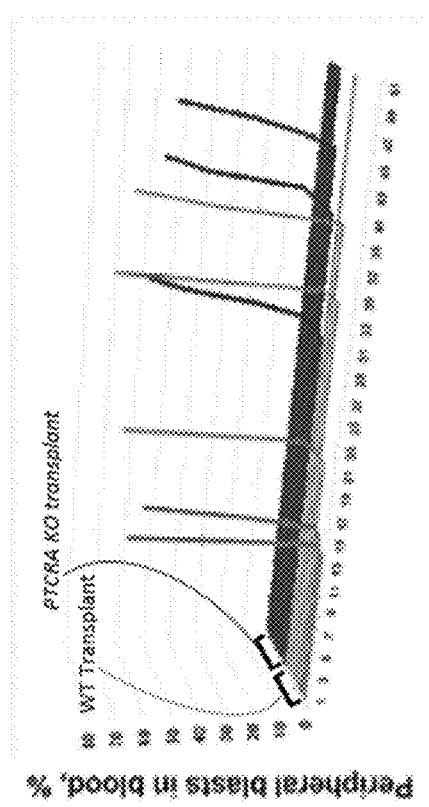

Additionally, a series of recurrent, but infrequently reported, mutations relevant to T-ALL was observed, including: Fat1, Ddx3x, Ptpn11 and Ikzf1 (Table 1) (Liu, et al. 2017 Nat Genet 49:1211-1218; Molteni, et al. 2010 Leukemia 24:232-235). Gene expression profiling of Ptcra-deficient tumors revealed 60 differentially expressed genes, relative to wild type T-ALL tumors. This gene expression signature was notable for strong down-regulation of genes implicated in the DN to DP transition and upregulation of multiple genes enriched in early T cell progenitor-like (ETP) ALL (Zhang, et al. 2012 Nature 481:157-163), including Ppbp, Cd93, Lyl1, Dhrs and Pim1, and early stages of thymocyte development, such as Ikzf2 and Id3, indicating a an earlier developmental phenotype for Ptcra-deficient tumors (FIG. 7C).

Figure 8A:
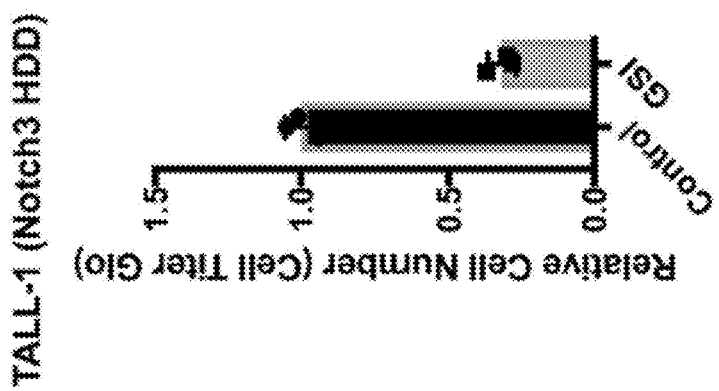
FIGS. 8A and 8B demonstrate NOTCH3 expression and potential function in human T-ALL.
Figure 8B:
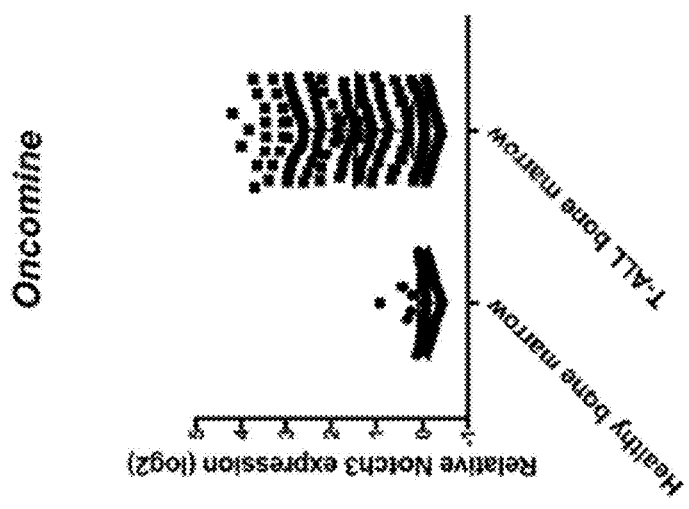
Figure 9:
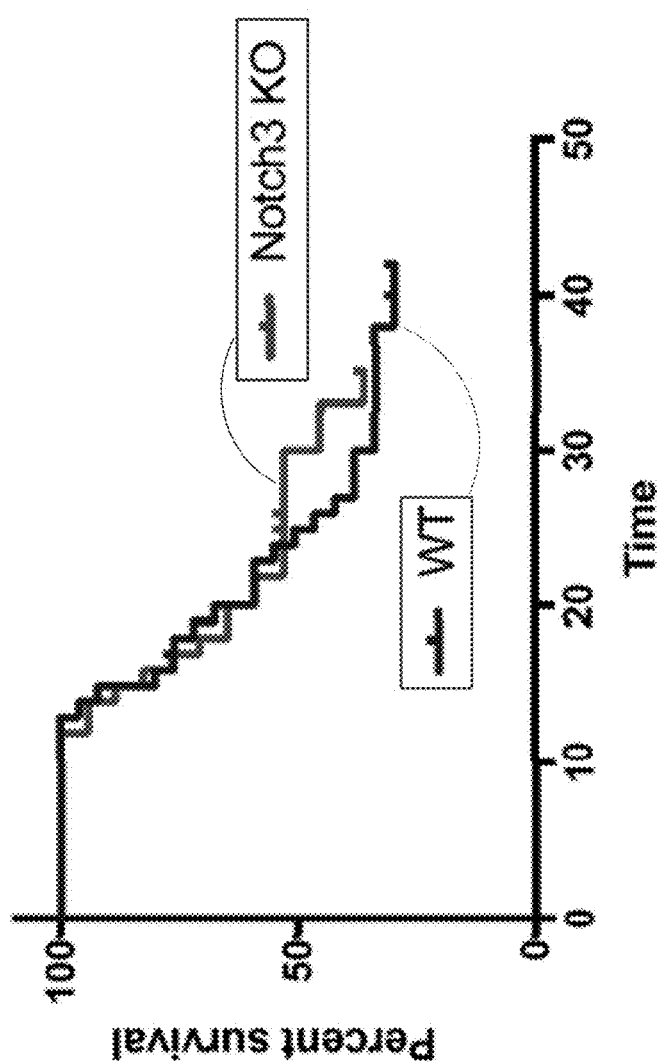
FIG. 9 demonstrates that genetic ablation of Notch3 does not impair T-ALL development in thymic transplant model. Notch3 KO thymi give rise to T-ALL with similar frequency as wild type (WT) controls in the thymic transplantation model.

NOTCH3 mutations have been reported in the literature for human T-ALL (Martins, et al. 2014 Nature 509:465-470), and NOTCH3 is overexpressed in a large fraction of human T-ALL cases (FIG. 8A). Additionally, treatment of a human T-ALL cell line harboring a gain-of-function NOTCH3 mutation but wild type for NOTCH1 with a gamma-secretase inhibitor was found to impair cell proliferation (FIG. 8B). However, in contrast to deletion of Ptcra, transplanting Notch3$^{-/-}$ thymi did not result in decreased leukemogenesis, and, in fact, gave rise to T-ALL with similar efficiency as wild type control thymi (FIG. 9). Any potential role for oncogenic Notch3 signaling might be masked by the propensity of the murine system to develop Notch1 gain-of-function mutations (Ashworth, et al. 2010 Blood 116:5455-5464). In Notch3$^{-/-}$ tumors, multiple ligand-independent Notch1 mutations were observed that are sufficient to drive leukemogenesis of T-ALL (data not shown).

Thus, Ptcra deficiency resulted in a markedly reduced capacity to induce leukemogenesis, significantly decreased overall disease penetrance, and median time to neoplastic disease not reached during the course of the study.

Example 4. PTCRA Expression in Human T-ALL

Indicative of a possible role for pre-TCR signaling in human T-ALL, PTCRA was expressed in most human T-ALL cell lines, but not in cell lines representing other classes of leukemia or any other non-leukemic cancer cell lines within the Cancer Cell Line Encyclopedia (CCLE) (FIG. 10A and data not shown) (Barretina, et al. 2012 Nature 483:603-607; Cancer Cell Line Encyclopedia 2015 Nature 528:84-87). The specific expression of PTCRA was further validated in human T-ALL in two independent patient cohorts. In the St. Jude Children's Research Hospital cohort, comprised of 2,224 pediatric and young adult patients with hematopoietic malignancies (1,333 B-ALL cases, 497 AML cases, 373 T-ALL cases and 24 mixed lineage leukemia cases) for which RNA-seq data was available, PTCRA was strongly and differentially expressed in T-ALL patient samples (FIG. 10B) relative to non-T cell derived leukemias (Zhou, et al. 2016 Nat Genet 48:4-6). Similarly, in the Haferlach cohort of 2,096 pediatric and adult patients with leukemias and myelodysplastic syndromes (576 B-ALL cases, 542 AML cases, 206 MDS cases, 174 T-ALL cases, 448 CLL cases, 76 CML cases and 74 non-leukemia and healthy bone marrow control cases), PTCRA was selectively expressed in T-ALL patient samples (FIG. 10C) (Haferlach, et al. 2010 J Clin Oncol 28:2529-2537). Stratifying the St. Jude Children's Research Hospital cohort according to T-ALL subtype (Liu, et al. 2017 Nat Genet 49:1211-1218) demonstrated that PTCRA is highly expressed across most molecular T-ALL subsets, representing the large majority of all human T-ALL cases (FIG. 11A) (Zhou, et al. 2016 Nat Genet 48:4-6).

Figures 11A, 11B:
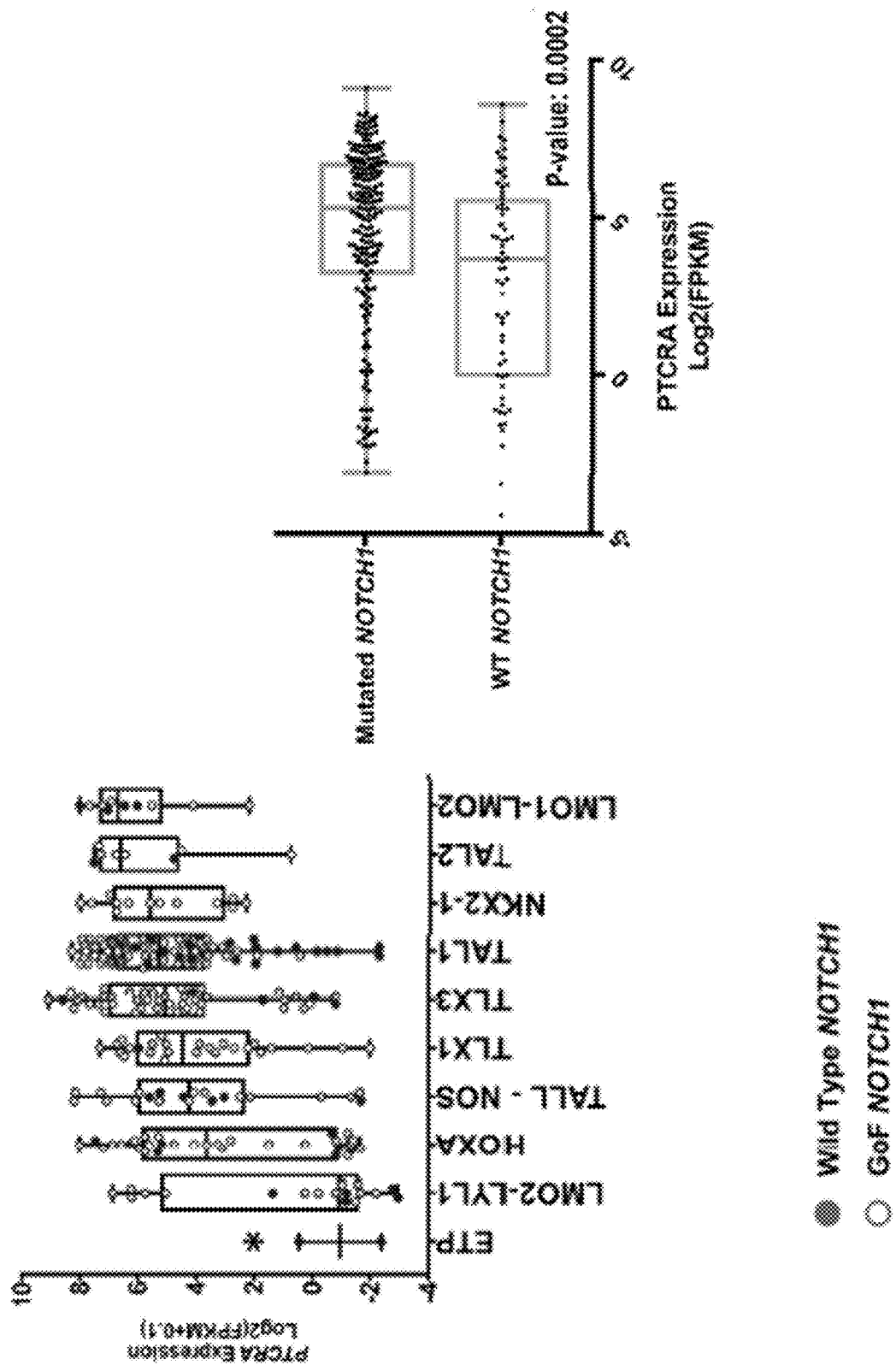
FIGS. 11A and 11B demonstrate that PTCRA is expressed across all major subtypes of T-ALL, except for the ETP-like subgroup, and that Notch1 mutations are associated with higher levels of PTCRA expression in human T-ALL. Expression of PTCRA was in T-ALL patients from St. Jude's Pediatric Cancer Patient cohort.
Figure 12:
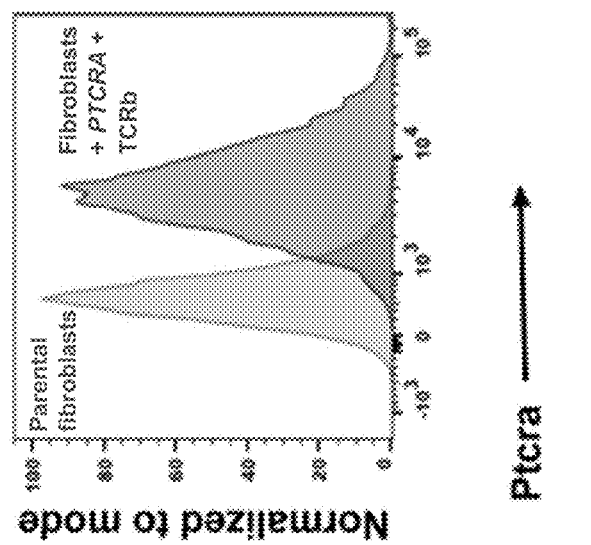
FIG. 12 demonstrates validation of mAb clone 2F5 binding to human PTCRA. Murine fibroblast cells were co-transfected with plasmids encoding human PTCRA and a rearranged murine Tcrb gene. PTCRA cell surface expression was assessed by flow cytometry using the 2F5 mAb targeting Ptcra, following the manufacturer's protocol.

In line with the characteristics of the murine T-ALL model, PTCRA is expressed at lower levels in ETP and ETP-like (LMO2/LYL1) human T-ALL samples (FIG. 11A). Without being bound to a particular theory, but consistent with the molecular biology of Notch signaling, PTCRA expression in T-ALL was positively associated with NOTCH1 gain-of-function (GoF) mutations; although PTCRA expression was retained in subsets of patients with wild type NOTCH1 status. (FIG. 11B). In a series of prospectively collected acute leukemia patient samples PTCRA cell surface expression was only detected cell in T-ALL samples, but not in B-ALL or AML samples. (FIG. 10D, FIG. 12, FIG. 13). Without being bound to a particular theory, but consistent with the developmental functions of the pre-TCR, mature T-cells from normal donors did not express PTCRA (FIG. 10E). Thus, human T-ALLs were shown to frequently express high levels of PTCRA.

Figure 14:
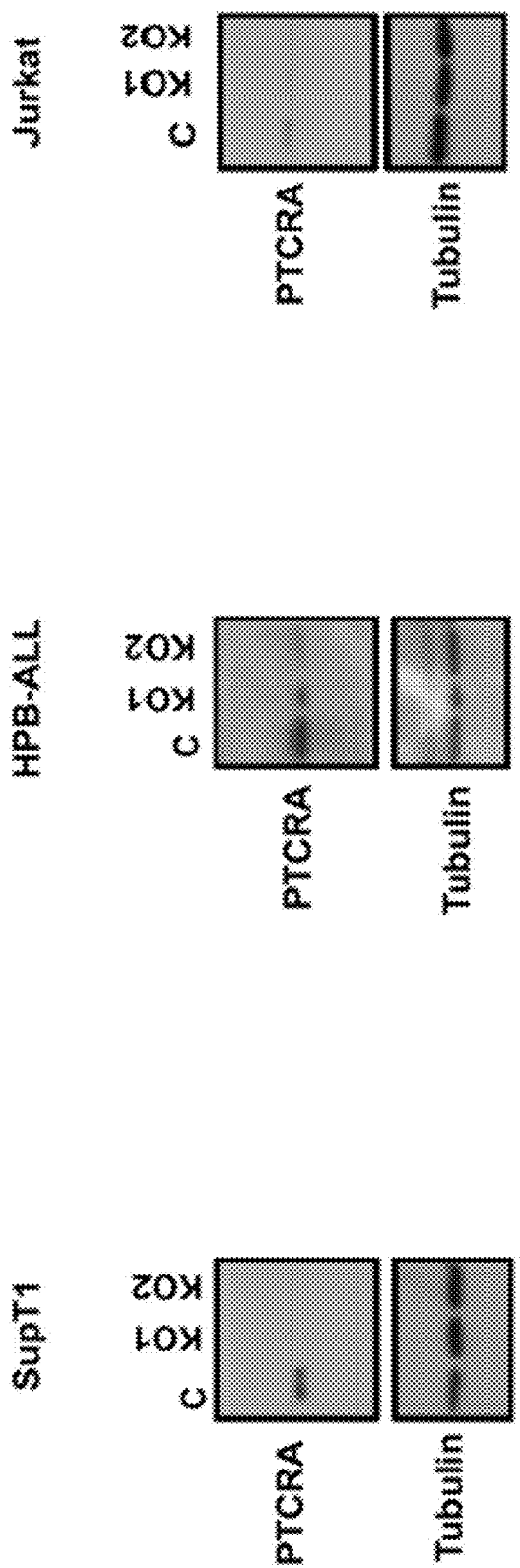
FIG. 14 provides a Western blot analysis confirming efficient ablation of PTCRA expression in human PTCRA KO T-ALL cell lines SupT1, HPB-ALL and Jurkat. PTCRA was targeted with two separate CRISPR/Cas9 guide RNA (KO1, KO2) and control (C) guide RNA. Tubulin expression was used as loading control.

Example 5. Deletion of PTCRA in T-ALL Cell Lines Via CRISPR/Cas9 Impairs Tumor Growth In Vitro and In Vivo To assess the function of the pre-TCR in human T-ALL, SupT1, HPB-ALL, and Jurkat cell lines stably expressing Cas9 were generated and transduced with either PTCRA-targeting or control gRNAs. Successful targeting of PTCRA and reduction of protein expression in these cell lines was confirmed by Western blot analysis (FIG. 14). Deletion of PTCRA in SupT1 and HPB-ALL cells, which expressed the highest levels of PTCRA (Supplementary Table 3), resulted in significant reduction of cell proliferation (FIG. 15A). In comparison, Jurkat cells, which express lower levels of PTCRA and are more developmentally mature than either SupT1 or HPB-ALL cells (Aarnoudse, et al. 2002 Int J Cancer 99:7-13), were insensitive to deletion of PTCRA by CRISPR/Cas9 (FIG. 15A, FIG. 13). When subcutaneously implanted in the flank of NSG mice, wild type SupT1 cells developed tumors, whereas SupT1PTCRA-KO cells did not (FIG. 15B).

The observation that PTCRA is required for proliferation in a subset of human T-ALL cell lines indicates that signaling through the pre-TCR is able to drive proliferation in these cells. Thymocyte pre-TCR signaling is mediated by SRC-family protein tyrosine kinases, with a pivotal role for lymphocyte-specific protein tyrosine kinase, LCK (Lin, et al. 2000 *J Exp Med* 191:703-716). Without being bound to a particular theory, but consistent with the idea that signaling, per se, through the pre-TCR is required for proliferation in PTCRA-dependent T-ALL cell lines, treating these cell lines with the SRC-family kinase inhibitor, PP1, induced a dose-dependent anti-proliferative response (FIG. 15C). Additionally, CRISPR/Cas9-mediated deletion of LCK in SupT1 cells strongly inhibited proliferation in vitro (FIG. 15D). Collectively, results from the thymic transplantation-based mouse model of T-ALL and human T-ALL cell lines reveal a critical role for pre-TCR signaling in driving and sustaining the leukemogenesis of T-ALL. Thus, a subset of human T-ALL were found sensitive to deletion of PTCRA.

Example 6. Internalization Kinetics of the Pre-TCR

In certain embodiments, the ADC target is cell surface-expressed and gets internalized with the payload upon binding. As a result, there is less risk of bystander effect.

Figure 18A:
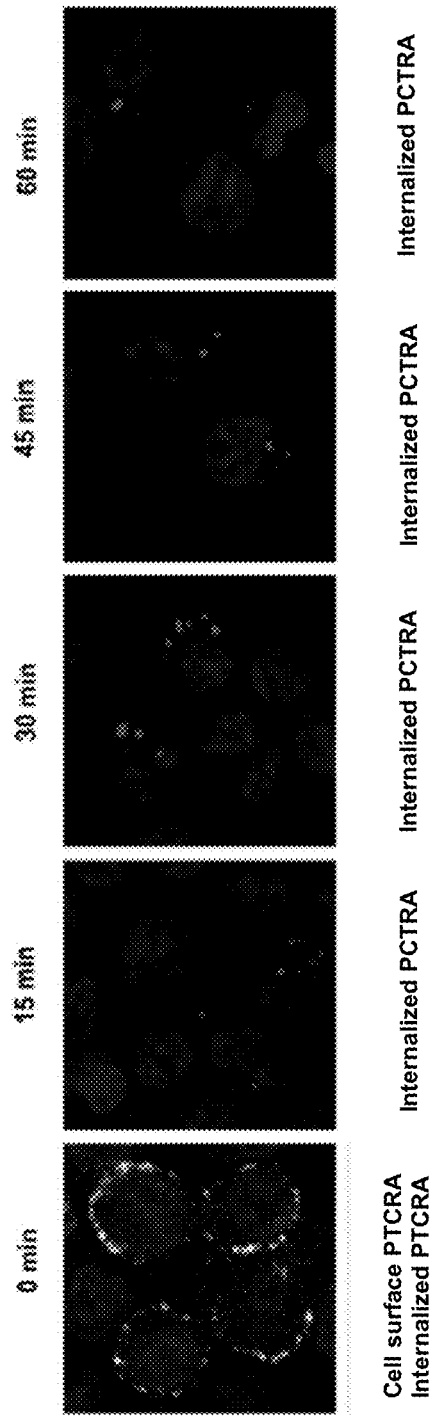
FIGS. 18A and 18B demonstrate the internalization kinetics of the pre-TCR.
Figure 18B:
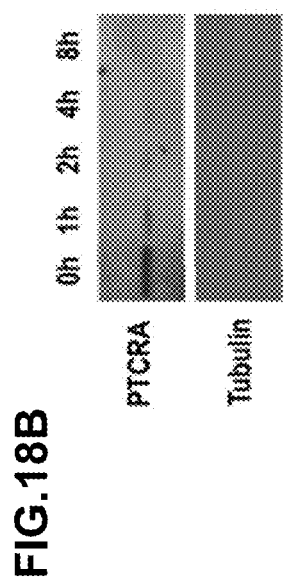

SupT1 cells, which endogenously express PTCRA, were stained with anti-PTCRA antibody at 4° C. for thirty minutes, whereupon the cells were temperature shifted to 37° C. and stained with a secondary antibody at the indicated time post-temperature shift. The cells were then fixed, and immunofluorescent confocal microscopy was used to visualize PTCRA localization. PTCRA was detected at the cell surface of SupT1 cells at 0 minutes, but rapidly and robustly internalizes over the time course being examined (FIG. 18A). SupT1 cells were treated with the translation inhibitor, cycloheximide, for 0 hrs, 1 hr, 2 hrs, 4 hrs, or 8 hrs, at which time they were harvested, lysed, and the extracts were used for immunoblotting. PTCRA was rapidly degraded over the 8-hr time course of the experiment (FIG. 18B). The effective internalization suggests that the ADC is viable.

Example 7. Targeting PTCRA with Cytotoxic Antibody-Drug Conjugates Promotes Specific Killing of T-ALL Cells In Vitro and In Vivo Given the selective expression of PTCRA in leukemic cells but not normal, mature T cells, and its rapid, constitutive internalization, it was reasoned that targeting the pre-TCR with a cytotoxic antibody-drug conjugate may represent a viable therapeutic strategy in T-ALL. To this end, primary PTCRA+ murine T-ALL (mTALL) cells, generated via thymic transplantation as described, were treated with either a PTCRA-targeting mouse mAb or an isotype control mAb, followed by treatment with anti-mouse IgG-Fc linked to the microtubule inhibitor monomethyl auristatin E (MMAE) via a non-cleavable linker. Robust killing of mTALL cells treated with PTCRA-targeting mAb was observed, but no killing in control-treated cells (FIG. 16A). Next, the PTCRA-targeting mAb was conjugated to linker payload MAYT2LP (structure provided herein), thereby linking the PTCRA-targeting mAb to the potent microtubule inhibitor (MAYT2) via a non-cleavable linker. To this end, the PTCRA-targeting mAb was conjugated to MAYT2INT. The resulting drug-antibody ratio (DAR) was ~3.5, and the compound was hereafter referred to as PTCRA-ADC. The PTCRA-ADC, but not a control-ADC, promoted dose-dependent killing of leukemic cells with an IC50 in the low nanomolar range (FIG. 16B, tabular form of values shown in FIG. 16F).

Figure 17:
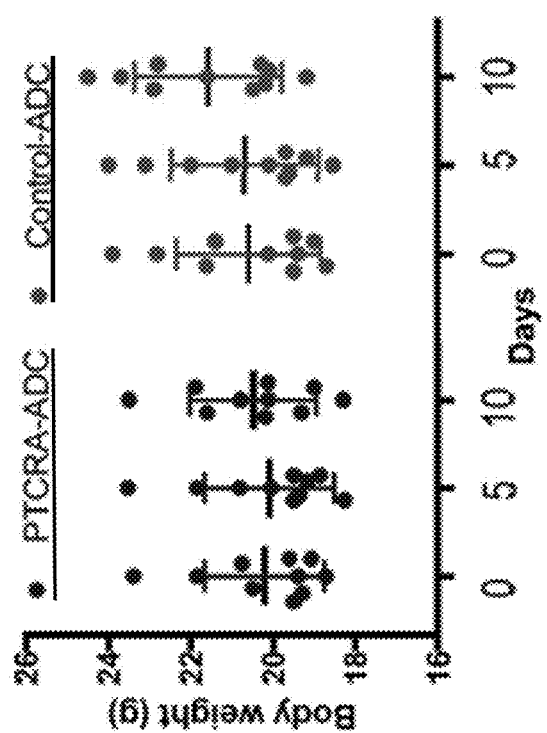
FIG. 17 depicts the body weight over time of mice treated with PTCRA-ADC.

Since the PTCRA mAb clone used herein also binds to human PTCRA (FIG. 12), the activity of PTCRA-ADC was tested on a panel of human leukemia cell lines. The PTCRA-ADC selectively induced killing of human SupT1 T-ALL cells but did not impact viability of B-ALL (NALM6) and AML (K562) cell lines (FIG. 16C, tabular form of values shown in FIG. 16G). AML and B-ALL cells have very low levels of PTCRA at the RNA level (median and mean approaching <1 for most datasets). Importantly, PTCRA-ADC treatment also had no effect on the viability of normal, peripheral T cells, consistent with its selective expression pattern. The potency of the PTCRA-ADC in vitro prompted the evaluation of in vivo activity in a highly aggressive, disseminated T-ALL model. NSG mice were i.v. injected with 100,000 PTCRA+ mTALL cells, randomized according to tumor burden on day 2 post-implantation, and treated with either PTCRA-ADC or control-ADC on days 2, 6 and 12. Tumor burden was assessed longitudinally throughout the study by quantifying the number of blast cells in the peripheral blood and by quantifying splenic mass at the end of study at day 14. T-ALL-bearing mice treated with the PTCRA-ADC exhibited statistically significantly reduced tumor burden, both in peripheral blood and spleen relative to control-ADC controls (FIG. 16D, tabular form of values shown in FIG. 16H, and FIG. 16E, tabular form of values shown in FIG. 16I). PTCRA-ADC treatment appeared well tolerated with no signs of distress or differences in body weight evident in the treatment group relative to control mice (FIG. 17). Collectively, these results indicate that targeting the pre-TCR in T-ALL with a cytotoxic ADC represents a promising approach to specifically eradicate tumor cells while sparing normal T cells and to support the further development of PTCRA-targeting agents for clinical translation.

The biology of T-ALL is strongly influenced by its developmental origins. For example, mutations in NOTCH1, a critical regulator of thymocyte development, are found in approximately 60% of patient tumors. Less is known, however, about the extent to which other determinants of thymocyte development participate in the leukemogenesis of T-ALL. Thus, to elucidate a role for thymocyte development factors beyond Notch1 in the pathogenesis of T-ALL, a thymic transplantation-based model was used that spontaneously gives rise to genetically distinct T-ALL cases and recapitulates many of the key genetic and histopathologic features of the human disease (Martins, et al. 2014 *Nature* 509:465-470). RNA sequencing of tumors derived from this model revealed a strong upregulation of factors associated with progression through the β-selection checkpoint, a key step in thymocyte development that selects against thymocytes that have unsuccessfully rearranged the TCRβ locus. Thymocytes that successfully complete the DN3 to DN4 transition by passing this checkpoint initiate a rapid bout of proliferation and survival signaling. The β-selection checkpoint is a key step in thymocyte development. It was hypothesized that upregulation of factors required for crossing the β-selection checkpoint may contribute to leukemogenesis in this model. The role of the key DN3 to DN4 transition factor, the pre-TCR, in the leukemogenesis of T-ALL was validated using Ptcra KO thymic transplants, and a marked reduction in the efficiency of leukemogenesis was observed in this system. Further, it was demonstrated that human T-ALLs frequently express high levels of PTCRA and a subset of human T-ALL cell lines are sensitive to deletion of PTCRA or chemical inhibition of the SRC-family kinases that mediate pre-TCR signaling.

These results support the paradigm that the developmental biology of T-cell precursors informs the leukemogenesis and clinical course of T-ALL. This is best characterized by the pivotal role of oncogenic NOTCH1 signaling in T-ALL.

Several reports have described a possible role for the pre-TCR in the pathogenesis of T-ALL, suggesting that it cooperates with other leukemogenic genomic alterations including TEL-JAK2 fusions (dos Santos, et al. 2007 *Blood* 109:3972-3981), activating NOTCH mutations (Bellavia, et al. 2002 *PNAS USA* 99:3788-3793), and Ikaros deficiency (Winandy, et al. 1999 *J Exp Med* 190:1039-1048). This is the first report to describe a critical role for pre-TCR signaling in the leukemogenesis of T-ALL beyond the context of specific, genetically engineered driver mutations and is the first report to demonstrate a requirement for pre-TCR signaling in human T-ALL cell lines.

The pre-TCR regulates the proliferative burst that accompanies the DN3 to DN4 transition and helps cells avoid death by β-selection (von Boehmer 2005 *Nat Rev Immunol* 5:571-577). The inability of Ptcra KO thymi to efficiently generate leukemias in the model described herein could be explained by signaling through the pre-TCR being required for the leukemogenesis of T-ALL, i.e., the signaling is actively contributing to the pathogenesis of T-ALL. First, Ptcra KO thymi do contain αβ-lineage thymocytes and are able to support the generation of mature T-cells, indicating that progression beyond the DN3 phase is possible in the absence of Ptcra. Further, increasing the number of Ptcra thymic lobes transplanted did not increase the efficiency of leukemogenesis, suggesting that DN4 or beyond thymocytes were not a limiting factor for transformation. Finally, the observation that knocking out PTCRA in established human T-ALL cell lines resulted in a cell proliferation defect strongly points to signaling through the pre-TCR as important in the context of T-ALL.

The fact that PTCRA is a thymocyte-restricted Notch1 target implies that targeting PTCRA may afford a more favorable therapeutic window relative to the inhibition of Notch1, which results in gastrointestinal toxicity due to Notch1 function in intestinal progenitor cells (Takebe, et al. 2014 *Pharmacol Ther* 141:140-149; Wei, et al. 2010 *Mol Cancer Ther* 9:1618-1628). Additionally, the elevated expression of PTCRA in leukemic T cells but the absence thereof in normal adult T cells, consistent with its development functions, allows for selective targeting of T-ALL without affecting the normal T cell compartment. Importantly, impairment of normal T cell immunity has been a major impediment to the development of next-generation therapies targeting T cell-derived malignancies (Martin, et al. 2006 *Clin Infect Dis* 43:16-24).

Not all genetically engineered mouse models of T-ALL exhibit a requirement for pre-TCR signaling, including Trp53 or ATM deficient mice (Liao, et al. 1998 *Mol Cell Biol* 18:3495-3901; Petiniot, et al. 2000 *PNAS USA*. In these cases, it appears that malignancy is initiated before thymocytes begin to express the pre-TCR at DN3. Without being bound to a particular theory, this is consistent with human literature, as well, where the pre-TCR is upregulated in more than half of T-ALL cases, particularly those of cortical descent. It was additionally observed that PTCRA is expressed at low levels in ETP-ALL. Data for differential expression of PTCRA across cohorts in the St Jude's Pediatric Cancer dataset (FIG. 10B, FIG. 11B) is particularly compelling, because the sequencing was performed on sorted leukemic cell populations, reducing confounding due to cellular heterogeneity within the tumor microenvironment.

Cumulatively, an important role for pre-TCR signaling in the pathogenesis of T-ALL is highlighted herein. Given the dearth of targeted therapies for the disease, the pre-TCR may be a viable therapeutic target in this indication.

Using a thymus transplantation-based, spontaneous mouse model of T-ALL, it was found that multiple β-selection checkpoint factors were upregulated in leukemic T cells, including Ptcra, a subunit of the pre-T cell receptor (pre-TCR) complex. Genetic ablation of Ptcra in the mouse model dramatically reduced the occurrence of T-ALL. In human T-ALL cell lines, CRISPR/Cas9 knockout of PTCRA reduced in vitro proliferative capacity and the ability to form tumors in vivo. Analysis of clinical T-ALL datasets and patient samples demonstrated that PTCRA is highly and specifically expressed in leukemic T cells but not in normal, mature T cells, supporting an appropriate therapeutic window for targeted (PTCRA-directed) therapy in T-ALL. Cumulatively, the Examples highlight an important role for pre-TCR signaling in driving and sustaining T-ALL.

Example 8. Synthesis of Additional Linker Payloads

Proton NMR spectra were acquired on a Varian Inova 300 or 500 MHz NMR instrument. Chromatographic purities were determined on an Agilent 1200 Series or 1100 Series LC/MS system with electrospray ionization source and triple-quad ion trap analyzer using a Merck Chromolith RP-18e analytical HPLC column (monolithic, 50×2 mm) and the following analytical HPLC method: injection volume 5 μL; flow rate 1 mL/min; 5→95% acetonitrile in water with 0.05% AcOH over 5 mins; Agilent diode array detector at λ=254, 220 or 195 nm; room temperature. All starting materials and solvents were purchased commercially and used without purification, unless otherwise noted.

Linker payload 10 was synthesized from Compound 1 as described below.

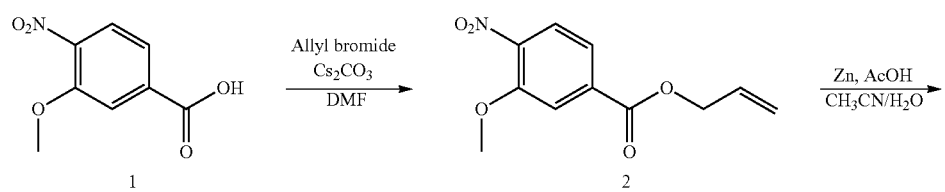

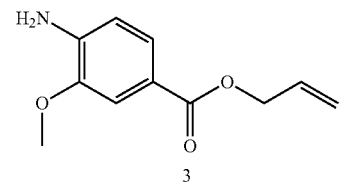
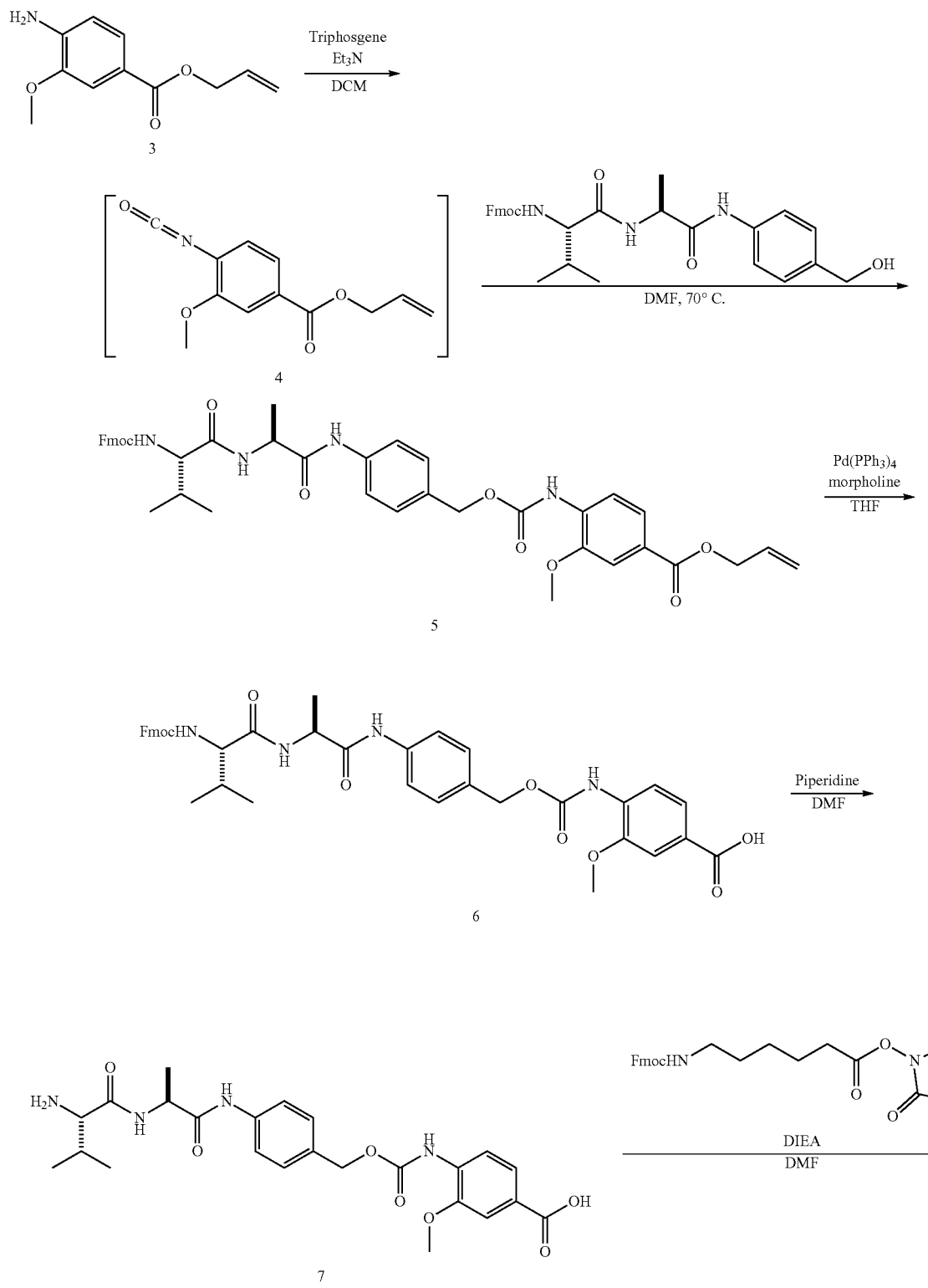

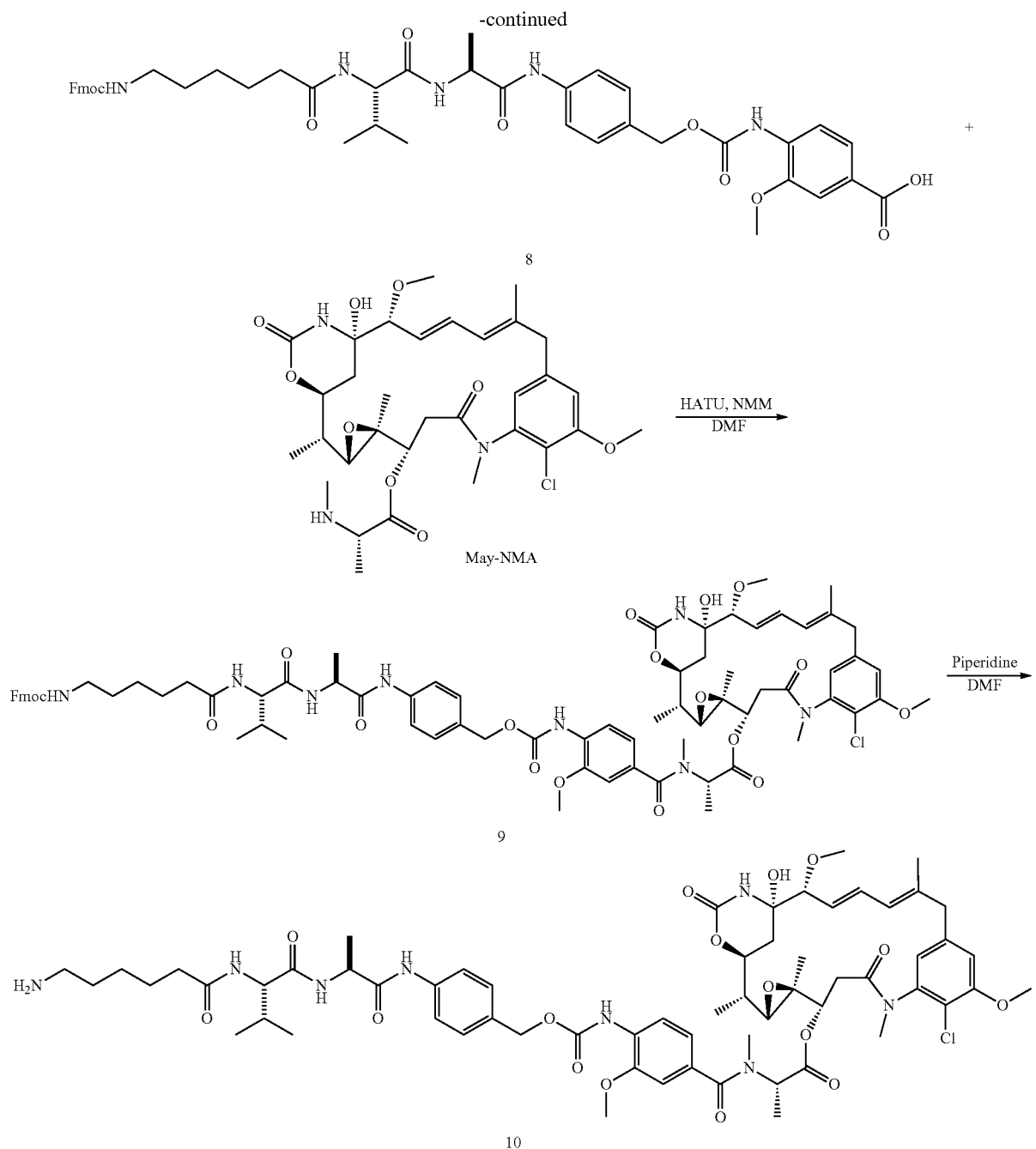

Maytansin-N-methyl-L-alanine-3-methoxylbenz-amide-4-amino-benzamidocarbamate-Ala-Val-Cap-NH2 (10)

Synthesis of Allyl 4-amino-3-methoxy benzoate (3)

Step 1: 3-Methoxy-4-nitrobenzoic acid 1 (500 mg, 2.53 mmol) was dissolved in 3.0 mL anhydrous DMF, at room temperature, under Argon atmosphere. $Cs_2CO_3$ (1.66 g, 5.10 mmol) and allyl bromide (330 μL, 3.80 mmol) were added sequentially. The resulting mixture was left to stir at room temperature for 3 hours. The reaction mixture was then partitioned between water (10 mL) and DCM (10 mL); the layers were then separated; the organic layer was dried over $Na_2SO_4$, filtered, and evaporated under vacuum. The residue was dissolved in 1 mL of DMF and loaded on a 24 g silica gel column. Eluent: EtOAc and hexane (0% to 100% EtOAc over 25 min). The fractions containing product were combined and evaporated under vacuum. The product was obtained as a white solid (500 mg, 83% yield). MS (ESI, pos.): calc'd (calculated) for $C_{11}H_{12}NO_5$, 238.1; found (M+H) 238.1.

Step 2: Compound 2 (142 mg, 0.60 mmol) was dissolved in 7 mL $CH_3CN/H_2O$ 4:3. AcOH (1.30 mL, 24.0 mmol) and Zn dust (783 mg, 12.0 mmol) were added sequentially. The resulting mixture was left to stir at room temperature for 2 hours, when the reaction was determined to be complete by LC/MS. The reaction mixture was filtered through celite and partially evaporated under vacuum. The reaction mixture was then partitioned between water (10 mL) and DCM (10 mL); the layers were then separated. The organic layer was washed with sat. (aq) NaHCO$_3$ (1×10 mL), then dried over Na$_2$SO$_4$, filtered, evaporated under vacuum. The crude product was obtained as a dark yellow oil (120 mg, 97% yield). It was used in the next step without purification. MS (ESI, pos.): calc'd for C$_{11}$H$_{14}$NO$_3$ 208.1 (M+H); found 208.1; MS (ESI, neg.) calc'd for C$_{11}$H$_{12}$NO$_3$ 206.1 (M−H); found 206.1.

Synthesis of Compound 5:

Compound 3 (250 mg, 1.21 mmol) was dissolved in 8.0 mL DCM, at room temperature, under an Argon atmosphere. The solution was cooled to 0° C. and Et$_3$N (504 μL, 3.62 mmol) and triphosgene (717 mg, 1.21 mmol) were added sequentially. The resulting mixture was left to stir at 0° C. for 30 min and at room temperature for 2 hours. The solvent was evaporated under vacuum. The residue was dried under vacuum for 1 hour. A solution of FmocValAlaPAB alcohol (622 mg, 1.21 mmol) in anhydrous DMF (1.0 mL) was added dropwise. The mixture was heated at 70° C. for 1 hour. The mixture was left to cool to room temperature. It was then loaded directly onto a 100 g C18 Aq Isco column. Eluent: CH$_3$CN and H$_2$O (0.05% AcOH in both) eluted with 10% to 90% CH$_3$CN over 30 min. The fractions containing product were combined, partially evaporated under vacuum, frozen, lyophilized. The product was obtained as a white solid (180 mg, 20% yield). MS (ESI, pos.): calc'd for C$_{42}$H$_{44}$N$_4$O$_9$Na 771.3 (M+Na); found 771.2.

Synthesis of Compound 6:

Compound 5 (114 mg, 0.15 mmol) was dissolved in 2 mL anhydrous THF, at room temperature, under an Argon atmosphere. Morpholine (27.0 μL, 0.30 mmol) and Pd(PPh$_3$)$_4$ (176 mg, 0.15 mmol) were added sequentially. The resulting mixture was left to stir at room temperature for 2 hours, when the reaction was determined to be complete by LC/MS. The solvent was evaporated under vacuum. The residue was dissolved in 1 mL DMF and loaded onto a 30 g C$_{18}$ Aq Isco column. Eluent: CH$_3$CN and H$_2$O (0.05% AcOH in both) 0% to 70% CH$_3$CN over 30 min. The fractions containing product were combined, partially evaporated under vacuum, frozen, lyophilized. The product was obtained as a white solid (5.0 mg, 33% yield). MS (ESI, pos.): calc'd for C$_{39}$H$_{40}$N$_4$O$_9$Na, 731.3; found (M+Na) 731.3. MS (ESI, neg.) calc'd C$_{39}$H$_{39}$N$_4$O$_9$ 707.3; found (M−H) 707.3.

Synthesis of Compound 7:

Compound 6 (50.0 mg, 0.07 mmol) was dissolved in 1.5 mL anhydrous DMF, at room temperature, under Argon atmosphere. Piperidine (27.0 μL, 0.28 mmol) was added. The resulting mixture was left to stir at room temperature for 1 hour, when the reaction was determined to be complete by LC/MS. The solution was loaded directly onto a 30 g C18 Aq Isco column. Eluent: CH$_3$CN and H$_2$O (0.05% AcOH in both) 0% to 40% CH$_3$CN over 25 min. The fractions containing product were combined, partially evaporated under vacuum, frozen, and lyophilized. The product was obtained as a white solid (25 mg, 73% yield). MS (ESI, pos.): calc'd for C$_{24}$H$_{31}$N$_4$O$_7$, 487.2; found (M+H), 487.2. MS (ESI, neg.) calc'd for C$_{24}$H$_{29}$N$_4$O$_7$, 485.2; found (M−H) 485.2.

Synthesis of Compound 8:

Compound 7 (22.0 mg, 0.04 mmol) was dissolved in 1.0 mL anhydrous DMF, at room temperature, under Argon atmosphere. FmocNHCapOSu (22.0 mg, 0.05 mmol) and DIPEA (15.0 μL, 0.09 mmol) were added. The resulting mixture was left to stir at room temperature overnight. The solution was loaded directly onto a 50 g C18 Aq Isco column. Eluent: CH$_3$CN and H$_2$O (0% to 70% CH$_3$CN over 25 min). The fractions containing product were combined, partially evaporated under vacuum, frozen, and lyophilized. The product was obtained as a white solid (27 mg, 73% yield). MS (ESI, pos.): calc'd for C$_{45}$H$_{51}$N$_5$O$_{10}$Na, 844.4; found (M+Na) 844.3. MS (ESI, neg.) calc'd for C$_{45}$H$_{50}$N$_5$O$_{10}$, 820.4; found (M−H) 820.3.

Synthesis of Compound 9:

Compound 8 (40.0 mg, 0.05 mmol) was dissolved in 1.5 mL anhydrous DMF, at room temperature, under Argon atmosphere. Maytan-NMA (38.0 mg, 0.06 mmol), HATU (0.08 mmol) and NMM (11.0 μL, 0.10 mmol) were added. The resulting mixture was left to stir at room temperature overnight. The solution was directly loaded onto a 30 g C18 Aq Isco column. Eluent: CH$_3$CN and H$_2$O (0.05% AcOH in both) 0% to 40% CH$_3$CN over 25 min. The fractions containing product were combined, partially evaporated under vacuum, frozen, and lyophilized. The product was obtained as a white solid (46 mg, 65% yield). MS (ESI, pos.): calc'd for C$_{77}$H$_{94}$ClN$_8$O$_{18}$, 1453.6; found (M+H) 1453.8.

Synthesis of Compound 10:

Compound 9 (40 mg, 0.03 mmol) was dissolved in 1.5 mL anhydrous DMF at room temperature, under Argon atmosphere. Piperidine (8.0 μL, 0.08 mmol) was added. The resulting mixture was left to stir at room temperature. After 20 minutes, the reaction was determined to be complete by LC/MS. The mixture was loaded onto a 30 g C18 Aq Isco column. Eluent: CH$_3$CN and H$_2$O (0.05% AcOH in both) 0% to 50% CH$_3$CN over 25 min. The fractions containing product were combined, partially evaporated under vacuum, frozen, and lyophilized. The product was obtained as a white solid (20.0 mg, 59% yield). MS (ESI, pos.): calc'd for C$_{62}$H$_{84}$ClN$_8$O$_{16}$, 1231.6; found (M+H) 1231.7. MS (ESI, neg.): calc'd for C$_{62}$H$_{82}$ClN$_8$O$_{16}$, 1229.6; found (M−H) 1229.5. 1H NMR (500 MHz): δ 9.93 (bs, 1H), 8.69-8.68 (m, 1H), 8.15 (d, J=7.0 Hz, 1H), 7.81 (d, J=8.5 Hz, 1H), 7.70-7.68 (m, 1H), 7.59-7.58 (m, 2H), 7.33 (d, J=9.0 Hz, 2H), 7.22-7.21 (m, 1H), 6.93-6.86 (m, 4H), 6.65-6.56 (m, 2H), 5.96 (bs, 1H), 5.65-5.60 (m, 1H), 5.46-5.42 (m, 1H), 5.05 (s, 2H), 4.60-4.58 (m, 1H), 4.38-4.36 (m, 1H), 4.17-4.14 (m, 1H), 4.12-4.07 (m, 1H), 3.94 (s, 3H), 3.56-3.50 (m, 3H), 3.44 (d, J=13.0 Hz, 1H), 3.24-3.26 (m, 6H), 2.89 (bs, 3H), 2.81-2.79 (m, 1H), 2.73 (bs, 3H), 2.63-2.62 (m, 2H), 2.36-2.35 (m, 1H), 2.16-2.11 (m, 3H), 1.98-1.94 (m, 1H), 1.72-1.71 (m, 1H), 1.61 (bs, 3H), 1.49-1.45 (m, 4H), 1.34-1.12 (m, 11H), 1.13 (d, J=6.0 Hz, 3H), 0.87-0.82 (m, 9H).

Linker payload 14 was synthesized from Compound 6 as described below.

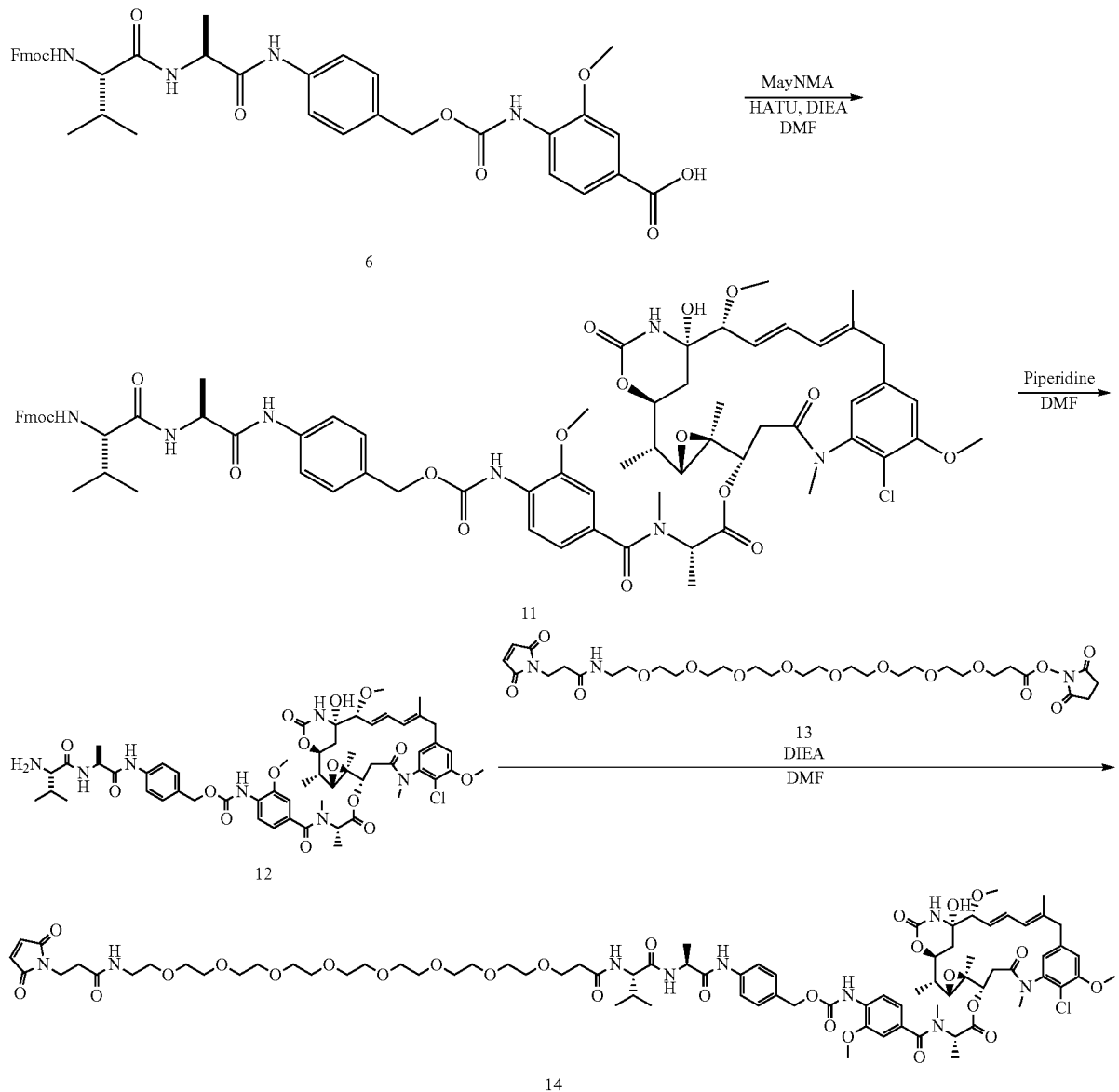

Maytansin-N-methyl-L-alanine-3-methoxybenz-amide-4-aminobenzamidocarbamate-Ala-Val-Peg8-Prop-Mal (14)

Synthesis of Compound 11:

To a solution of May-NMA, contaminated with DIEA, (190 mg, 0.292 mmol), in anhydrous DMF (1.6 mL), was added compound 6 (85.2 mg, 0.120 mmol), HATU (112 mg, 0.295 mmol) and NMM (65 µL, 0.591 mmol). The resulting reaction mixture was purged with Argon and allowed to stir at ambient temperature. After 20 h, additional compound 6 (27 mg, 0.0381 mmol) in DMF (1 mL) was added and the mixture was allowed to stir for an additional 8 h, when the full consumption of compound 6 was observed by LC/MS. The solution was then diluted with DMSO and loaded directly onto $C_{18}$ Aq Isco column (150 g). Eluent: $CH_3CN$ and H2O, each containing 0.05% of AcOH (5% to 95% $CH_3CN$). The fractions containing product were combined and lyophilized to afford compound 11 as a white solid (43.3 mg, 20% yield, based on compound 6). MS (ESI, pos.): calc'd for $C_{71}H_{82}ClN_7O_{17}Na$, 1362; found (M+Na) 1362.

Synthesis of Compound 12:

Compound 11 (40.2 mg, 0.0300 mmol) was dissolved in 20% diethylamine in DMF (v/v) (1.0 mL, 1.93 mmol DEA), then the resulting reaction mixture was allowed to stir at ambient temperature. After 20 min, the reaction was determined to be complete by LC/MS. The solution was then diluted with DMSO and loaded directly onto $C_{18}$ Aq Isco column (30 g). Eluent: $CH_3CN$ and H2O, each containing 0.05% of AcOH (0% to 100% $CH_3CN$). The fractions containing product were combined and lyophilized to afford compound 12 as a white solid (22.6 mg, 67% yield). MS (ESI, pos.): calc'd for $C_{56}H_{73}ClN_7O_{15}$, 1118; found (M+H) 1118; MS (ESI, neg.): calc'd for $C_{56}H_{71}ClN_7O_{15}$, 1116; found (M−H) 1116.

Synthesis of Compound 14:

To compound 12 (11.6 mg, 0.0104 mmol) was added MalPeg8N HS ester 13 (14.3 mg, 0.0207 mmol) in anhydrous DMF (0.1 mL) followed by additional DMF (0.1 mL) and DIEA (5.5 µL, 0.311 mmol). The resulting reaction mixture was purged with Argon and allowed to stir at ambient temperature. After 50 min, the reaction was determined to be complete by LC/MS. The solution was then diluted with DMSO and loaded directly onto $C_{18}$ Aq Isco column (15.5 g). Eluent: $CH_3CN$ and H2O, each containing 0.05% of AcOH (20% to 100% $CH_3CN$). The fractions containing product were combined and lyophilized to afford compound 14 as a white solid (6.0 mg, 34% yield). MS (ESI, pos.): calc'd for $C_{82}H_{114}ClN_9O_{27}Na$, 1714; found (M+H) 1714. 1H NMR (500 MHz; CDCl3): δ 8.72 (bs, 1H), 8.04 (dtd, J=5.3, 2.0, 0.9 Hz, 1H), 7.75 (dd, J=7.8, 0.6 Hz, 2H), 7.37-7.34 (m, 3H), 6.99-6.95 (m, 3H), 6.84 (s, 1H), 6.75-6.71 (m, 3H), 6.50-6.40 (m, 2H), 6.25 (s, 1H), 5.83-5.77 (m, 1H), 5.50-5.46 (m, 1H), 5.14 (s, 2H), 4.94-4.91 (m, 1H), 4.69-4.66 (m, 1H), 4.34-4.30 (m, 1H), 4.22 (t, J=6.0 Hz, 1H), 4.01 (s, 3H), 3.86 (t, J=7.2 Hz, 3H), 3.75 (s, 3H), 3.66-3.61 (m, 32H), 3.54-3.53 (m, 4H), 3.44-3.41 (m, 3H), 3.38 (s, 3H), 3.13-3.05 (m, 5H), 2.93 (s, 3H), 2.76-2.67 (m, 2H), 2.55-2.50 (m, 3H), 2.31-2.22 (m, 2H), 1.74-1.64 (m, 5H), 1.52-1.45 (m, 7H), 1.33-1.27 (m, 4H), 1.02 (dd, J=11.6, 6.8 Hz, 6H), 0.88 (s, 3H).

Example 9. Targeting PTCRA with Cytotoxic Antibody-Drug Conjugates Promotes Specific Killing of T-ALL Cells In Vitro and In Vivo Given the anti-leukemic effects of the PTCRA-ADC described in Example 7, it was explored whether additional linker payload formats would also have anti-leukemic activity. To this end, the PTCRA-targeting mAb was conjugated to additional linker payload MAYT3LP (structure provided herein), thereby linking the PTCRA-targeting mAb to the potent microtubule inhibitor (MAYT3) via a non-cleavable linker. Toward this end, the PTCRA-targeting mAb was reacted with MAYT3LPINT. The resulting drug-antibody ratio (DAR) was ~3.5, and the compound is hereafter referred to as PTCRA-MAYT3LP. Additionally, the PTCRA-targeting mAb was conjugated to additional linker payload MAYT4LP (structure provided herein), thereby linking the PTCRA-targeting mAb to the potent microtubule inhibitor (MAYT4) via a cleavable linker. To this end, the PTCRA-targeting mAb was reacted with compound 14 described in Example 8. The resulting drug-antibody ratio (DAR) was ~3.5, and the compound is hereafter referred to as PTCRA-MAYT4LP. The ADCs PTCRA-MAYT3LP and PTCRA-MAYT4LP, but not the appropriate control-ADCs, promoted dose-dependent killing of human PTCRA+ leukemic cells with an IC50 in the low nanomolar range (FIG. 19A, tabular form of values shown in FIG. 19G).

The activity of PTCRA-MAYT3LP and PTCRA-MAYT4LP was tested on a panel of human leukemia cell lines. The PTCRA-ADC selectively induced killing of human SupT1 T-ALL cells, but did not impact viability of B-ALL (NALM6) and AML (K562) cell lines (FIG. 19B, tabular form of values shown in FIG. 19H). AML and B-ALL cells have very low levels of PTCRA at the RNA level (median and mean approaching <1 for most datasets). Furthermore, PTCRA-MAYT3LP and PTCRA-MAYT4LP treatment also had no effect on the viability of normal, peripheral T cells, consistent with its selective expression pattern.

The in vitro efficacy of these molecules prompted the evaluation of their anti-leukemic activity in various in vivo models of T-ALL. To this end, NSG mice were injected subcutaneously (s.c.) with 5,000,000 PTCRA+ SupT1 cells and randomized to treatment with either a single dose of PTCRA-MAYT4LP or the Control-MAYT4LP, once the tumors became palpable. Tumor burden was quantified longitudinally throughout the study by measuring the tumor volume of the implanted tumor. T-ALL-bearing mice treated with the PTCRA-MAYT4LP exhibited statistically significantly reduced tumor burden relative to Control-2921 treated mice (FIG. 19C). In a separate experiment, C57BL/6 mice were intravenously (i.v.) injected with PTCRA+ mTALL cells and randomized according to tumor burden on day 1 post implantation and treated with either PTCRA-MAYT4LP or Control-2921 2qw. Tumor burden was assessed longitudinally throughout the study by quantifying the number of blast cells in the peripheral blood and by quantifying splenic mass at the end of study at day 21. T-ALL-bearing mice treated with the PTCRA-MAYT4LP exhibited statistically significantly reduced tumor burden, both in peripheral blood and spleen relative to Control-2921 controls (FIG. 19D and FIG. 19E). PTCRA-MAYT4LP treatment also was not associated with T-cell aplasia, highlighting the specificity of PTCRA-targeting molecules for leukemic T-cells versus non-malignant T-cells (FIG. 19F).

Collectively, these results confirm that targeting the pre-TCR in T-ALL with a cytotoxic ADC represents a promising approach to specifically eradicate tumor cells while sparing normal T cells and to support the further development of PTCRA-targeting agents for clinical translation.

The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the appended claims.

What is claimed is:

1. A method of inhibiting or reducing tumor growth in a tumor-bearing human subject, the method comprising administering to the subject an antibody-drug conjugate (ADC) comprising an antibody or antigen-binding fragment thereof that specifically binds human pre-T cell antigen receptor alpha (PTCRA), wherein the antibody or antigen-binding fragment thereof is conjugated to a therapeutic moiety, wherein the therapeutic moiety is a cytotoxic agent, wherein the cytotoxic agent is a maytansinoid, wherein the tumor expresses PTCRA.

2. The method of claim 1, wherein the tumor is a hematologic tumor.

3. The method of claim 1, wherein the tumor arises from the malignant transformation of T-cell progenitors.

4. A method for treating T-cell acute lymphoblastic leukemia (T-ALL) in a human subject, the method comprising administering to the subject an antibody-drug conjugate (ADC) comprising an antibody or antigen-binding fragment thereof that specifically binds human pre-T cell antigen receptor alpha (PTCRA), wherein the antibody or antigen-binding fragment thereof is conjugated to a therapeutic moiety, wherein the therapeutic moiety is a cytotoxic agent, wherein the cytotoxic agent is a maytansinoid, wherein T-ALL cells of the subject express PTCRA.

5. The method of claim 4, wherein the subject has T-ALL that is chemo-refractory and/or has relapsed.

6. The method of claim 4, wherein the ADC is administered at a dose of at least about 1 nM.

7. The method of claim 4, wherein the ADC is administered at a dose of at least about 10 nM.

8. The method of claim 4, wherein more than one dose of ADC is administered to the subject.

9. A method for killing cells that express human pre-T cell antigen receptor alpha (PTCRA), the method comprising contacting the PTCRA-expressing cells with an antibody-drug conjugate (ADC) comprising an antibody or antigen-binding fragment thereof that specifically binds human PTCRA, wherein the antibody or antigen-binding fragment thereof is conjugated to a therapeutic moiety, wherein the therapeutic moiety is a cytotoxic agent, wherein the cytotoxic agent is a maytansinoid.

10. The method of claim 9, wherein the cells are tumor cells.

11. The method of claim 4, wherein the ADC is comprised in a pharmaceutical composition.

12. The method of claim 11, wherein the pharmaceutical composition further comprises a pharmaceutically acceptable carrier.

13. The method of claim 9, wherein the maytansinoid is

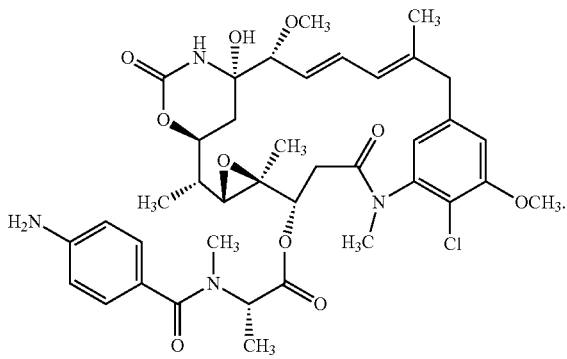 [SMILES: COc1cc2cc(c1Cl)N(C)C(=O)C[C@H](OC(=O)[C@H](C)N(C)C(=O)c1ccc(N)cc1)[C@]1(C)O[C@H]1[C@H](C)[C@@H]1C[C@@](O)(NC(=O)O1)[C@H](OC)/C=C/C=C(\C)C2]

14. The method of claim 4, wherein the antibody or antigen-binding fragment thereof is conjugated to the therapeutic moiety through a non-cleavable linker.

15. The method of claim 4, wherein the antibody or antigen-binding fragment thereof is conjugated to the therapeutic moiety through a linker, wherein the linker is bonded lysine residue of the antibody or antigen binding fragment thereof.

16. The method of claim 4, wherein the method results in the killing of T-cell acute lymphoblastic leukemia (T-ALL) cells.

17. The method of claim 4, wherein the method does not result in the killing normal peripheral T-cells.

18. The method of claim 9, wherein the maytansinoid is
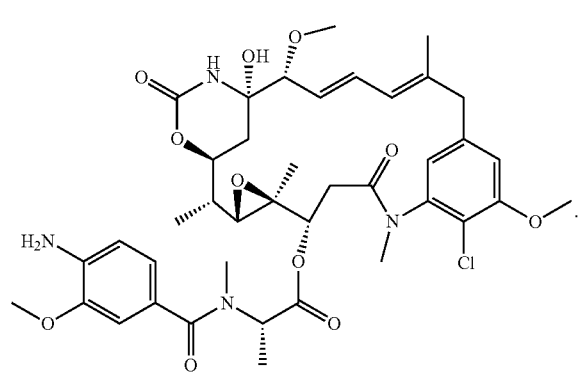
19. The method of claim 9, wherein the maytansinoid is
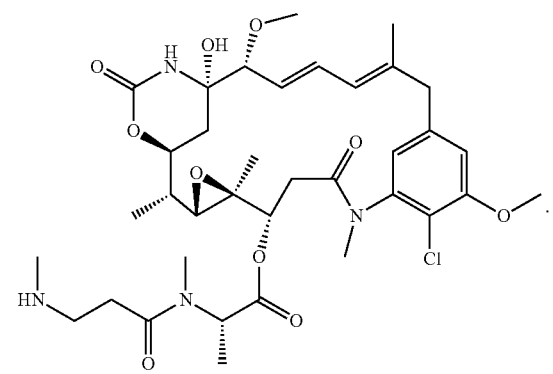
20. The method of claim 9, wherein the antibody or antigen-binding fragment thereof is conjugated to:
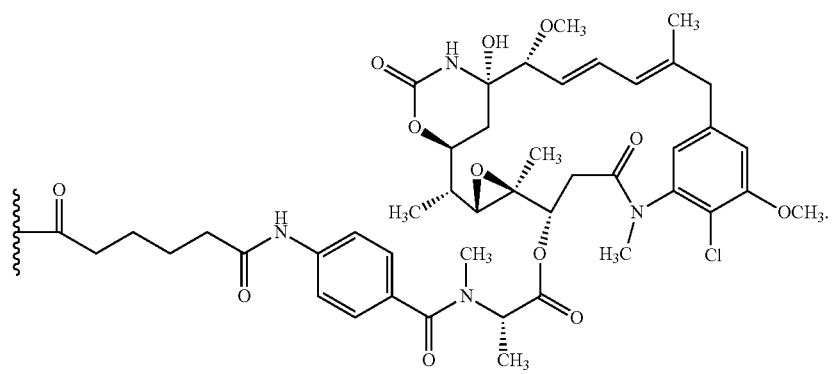 [SMILES: *C(=O)CCCCC(=O)Nc1ccc(C(=O)N(C)[C@@H](C)C(=O)O[C@H]2CC(=O)N(C)c3cc(cc(OC)c3Cl)C/C(C)=C/C=C/[C@@H](OC)[C@@]3(O)C[C@H](OC(=O)N3)[C@@H](C)[C@@H]3O[C@@]23C)cc1]
21. The method of claim 9, wherein the antibody or antigen-binding fragment thereof is conjugated to:
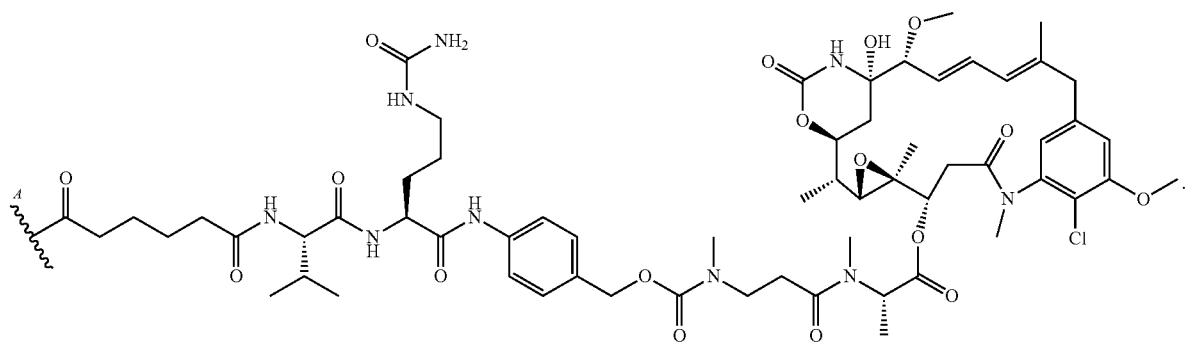

22. The method of claim 9, wherein the antibody or antigen-binding fragment thereof is conjugated to:
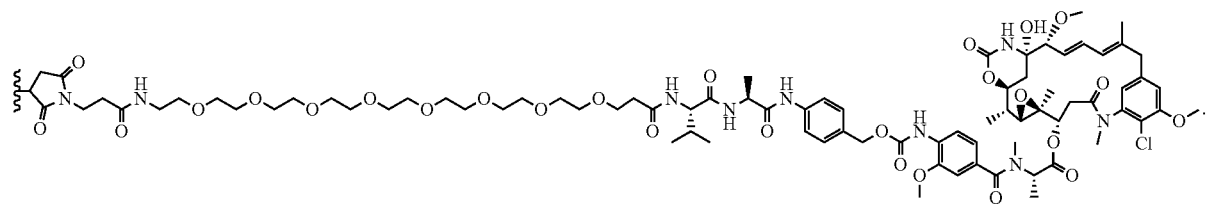 [SMILES: *C1CC(=O)N(CCC(=O)NCCOCCOCCOCCOCCOCCOCCOCCOCCC(=O)N[C@H](C(=O)N[C@@H](C)C(=O)Nc2ccc(COC(=O)Nc3ccc(C(=O)N(C)[C@@H](C)C(=O)O[C@H]4CC(=O)N(C)c5cc(cc(OC)c5Cl)C/C(C)=C/C=C/[C@@H](OC)[C@@]5(O)C[C@H](OC(=O)N5)[C@@H](C)[C@@H]5O[C@@]45C)cc3OC)cc2)C(C)C)C1=O]
* * * * *

SEQUENCE LISTING

```
<160> NUMBER OF SEQ ID NOS: 2

<210> SEQ ID NO 1
<211> LENGTH: 248
<212> TYPE: PRT
<213> ORGANISM: Homo sapiens

<400> SEQUENCE: 1

Met Leu Leu Val Asp Gly Lys Gln Gln Met Val Val Val Cys Leu Val
1               5                   10                  15

Leu Asp Val Ala Pro Pro Gly Leu Asp Ser Pro Ile Trp Phe Ser Ala
```

```
            20                  25                  30
Gly Asn Gly Ser Ala Leu Asp Ala Phe Thr Tyr Gly Pro Ser Pro Ala
            35                  40                  45

Thr Asp Gly Thr Trp Thr Asn Leu Ala His Leu Ser Leu Pro Ser Glu
 50                  55                  60

Glu Leu Ala Ser Trp Glu Pro Leu Val Cys His Thr Gly Pro Gly Ala
 65                  70                  75                  80

Glu Gly His Ser Arg Ser Thr Gln Pro Met His Leu Ser Gly Glu Ala
                 85                  90                  95

Ser Thr Ala Arg Thr Cys Pro Gln Glu Pro Leu Arg Gly Thr Pro Gly
            100                 105                 110

Gly Ala Leu Trp Leu Gly Val Leu Arg Leu Leu Phe Lys Leu Leu
            115                 120                 125

Leu Phe Asp Leu Leu Thr Cys Ser Cys Leu Cys Asp Pro Ala Gly
            130                 135                 140

Pro Leu Pro Ser Pro Ala Thr Thr Thr Arg Leu Arg Ala Leu Gly Ser
145                 150                 155                 160

His Arg Leu His Pro Ala Thr Glu Thr Gly Gly Arg Glu Ala Thr Ser
                165                 170                 175

Ser Pro Arg Pro Gln Pro Arg Asp Arg Arg Trp Gly Asp Thr Pro Pro
            180                 185                 190

Gly Arg Lys Pro Gly Ser Pro Val Trp Gly Glu Gly Ser Tyr Leu Ser
            195                 200                 205

Ser Tyr Pro Thr Cys Pro Ala Gln Ala Trp Cys Ser Arg Ser Ala Leu
            210                 215                 220

Arg Ala Pro Ser Ser Ser Leu Gly Ala Phe Phe Ala Gly Asp Leu Pro
225                 230                 235                 240

Pro Pro Leu Gln Ala Gly Ala Ala
                245

<210> SEQ ID NO 2
<211> LENGTH: 281
<212> TYPE: PRT
<213> ORGANISM: Homo sapiens

<400> SEQUENCE: 2

Met Ala Gly Thr Trp Leu Leu Leu Leu Ala Leu Gly Cys Pro Ala
 1               5                  10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
            130                 135                 140
```

-continued

```
Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
                260                 265                 270

Pro Pro Pro Leu Gln Ala Gly Ala Ala
            275                 280
```